(12) United States Patent
Grice et al.

(10) Patent No.: US 10,336,709 B2
(45) Date of Patent: Jul. 2, 2019

(54) LP-PLA2 INHIBITORS

(71) Applicant: ABIDE THERAPEUTICS, INC., San Diego, CA (US)

(72) Inventors: Cheryl A. Grice, Encinitas, CA (US); Micah Niphakis, San Diego, CA (US); Todd K. Jones, Solana Beach, CA (US)

(73) Assignee: ABIDE THERAPEUTICS, INC, San Diego, CA (US)

( * ) Notice: Subject to any disclaimer, the term of this patent is extended or adjusted under 35 U.S.C. 154(b) by 0 days.

(21) Appl. No.: 15/764,231

(22) PCT Filed: Sep. 29, 2016

(86) PCT No.: PCT/US2016/054541
§ 371 (c)(1),
(2) Date: Mar. 28, 2018

(87) PCT Pub. No.: WO2017/059135
PCT Pub. Date: Apr. 6, 2017

(65) Prior Publication Data
US 2018/0282288 A1    Oct. 4, 2018

Related U.S. Application Data

(60) Provisional application No. 62/236,716, filed on Oct. 2, 2015.

(51) Int. Cl.
C07D 233/80    (2006.01)
C07D 233/86    (2006.01)

(52) U.S. Cl.
CPC ......... *C07D 233/80* (2013.01); *C07D 233/86* (2013.01)

(58) Field of Classification Search
None
See application file for complete search history.

(56) References Cited

U.S. PATENT DOCUMENTS

| | | | |
|---|---|---|---|
| 4,003,912 A | 1/1977 | Franz | |
| 4,701,459 A | 10/1987 | Meanwell et al. | |
| 9,567,302 B2 | 2/2017 | Cisar et al. | |
| 2010/0210665 A1 | 8/2010 | Sawyers et al. | |
| 2011/0046105 A1 | 2/2011 | Jaehne et al. | |

FOREIGN PATENT DOCUMENTS

| | | |
|---|---|---|
| JP | 2004177416 A | 6/2004 |
| WO | WO-2009071638 A2 | 6/2009 |
| WO | WO-2009100155 A1 | 8/2009 |
| WO | WO-2009117444 A1 | 9/2009 |
| WO | WO-2010045401 A1 | 4/2010 |
| WO | WO-2010056309 A2 | 5/2010 |
| WO | WO-2013142307 A1 | 9/2013 |
| WO | WO-2017059135 A1 | 4/2017 |

OTHER PUBLICATIONS

Batz et al. Pharmakologisch active Polymere. Die Makromolekulare Chemie. 172:27-47 (1973) (w/English Abstract), (Eng. abstract only).
Berge et al. Pharmaceutical Salts. Journal of Pharmaceutical Sciences 66(1):1-19 (Jan. 1977).
Blizzard et al. Side chain SAR of bicyclic 2-lactamase inhibitors (BLIs). 1. Discovery of a class C BLI for combination with imipinem. Bioorg Med Chem Lett 20(3):918-921 (2010).
Chang et al. Proteome-wide reactivity profiling identifies diverse carbamate chemotypes tuned for serine hydrolase inhibition. ACS Chem Biol 8:1590-1599 (2013).
Chen et al. Monoacylglycerol lipase is a therapeutic target for Alzheimer's disease. Cell Rep. 2(5):1329-1339 (2012).
Hora. Stabilization of Bacillus subtilis α-amylase by amino group acylation. Biochimica et Biophysica Acta (BBA)—Protein Structure 310(1):264-267 (1973).
Iriepa et al. Synthesis, Structural and conformational study of some ureas derived from 3-methyl-2,4-diphenyl-3-azabicyclo[3.3.1]nonan-9beta-amine. Journal of Molecular Structure 482-483:431-436 (1999).
Jaouadi et al. Novel Preparation of N-Protected Amino Acid Active Esters Using 1.2.2.2-Tetrachloroethyl Carbonates. J Org Chem 52(12):2364-2367 (1987).
Long et al. Selective blockade of 2-arachidonoylglycerol hydrolysis produces cannabinoid behavioral effects. Nat Chem Biol. 5(1):37-44 (2009).
Nimura et al. Activated Carbamate Reagent as Derivatizing Agent for Amino Compounds in High-Performance Liquid Chromatography. Anal Chem 58(12): 2372-2375 (1986).
Nomura et al. Activation of the endocannabinoid system by organophosphorus nerve agents. Nat Chem Biol. 4(6):373-378 (2008).
Nomura et al. Endocannabinoid hydrolysis generates brain prostaglandins that promote neuroinflammation. Science 334(6057):809-813 (2011).
Nomura et al. Monoacylglycerol lipase regulates 2-arachidonoylglycerol action and arachidonic acid levels. Bioorg Med Chem Lett. 18(22):5875-5878 (2008).
PCT/US2013/031907 International Preliminary Report on Patentability dated Sep. 23, 2014.
PCT/US2013/031907 International Search Report dated Jun. 25, 2013.
PCT/US2016/054541 International Search Report and Written Opinion dated Dec. 9, 2016.
PCT/US2017/061867 International Search Report and Written Opinion dated Mar. 23, 2018.
Piro et al. A dysregulated endocannabinoid-eicosanoid network supports pathogenesis in a mouse model of Alzheimer's disease. Cell Rep. 1(6):617-623 (2012).

(Continued)

*Primary Examiner* — Po-Chih Chen
(74) *Attorney, Agent, or Firm* — Wilson Sonsini Goodrich & Rosati

(57) ABSTRACT

Provided herein are lipoprotein-associated phospholipase A2 (Lp-PLA2) inhibitors, pharmaceutical compositions thereof, and methods of their use for the treatment of disease.

20 Claims, No Drawings

(56) References Cited

OTHER PUBLICATIONS

Qiao et al. 5'-O-[( N-Acyl)sulfamoyl]adenosines as Antitubercular Agents that Inhibit MbtA: An Adenylation Enzyme Required for Siderophore Biosynthesis of the Mycobactins. J Med Chem 50(24):6080-6094 (2007).
Schmidt et al. Chroman and tetrahydroquinoline ureas as potent TRPV1 antagonists. Bioorg Med Chem Lett 21(5):1338-1341 (2011).
U.S. Appl. No. 14/383,076 Office Action dated Apr. 4, 2016.
U.S. Appl. No. 14/383,076 Office Action dated Jul. 15, 2016.
U.S. Appl. No. 14/383,076 Office Action dated Nov. 19, 2015.
Vasilevich et al. Conversion of O-succinimidyl carbamates to N-(O-carbamoyl)-succinmonoamides and ureas: effects of N-substituents and reaction conditions on the reaction pathway. Tetrahedron Letters 43(37):6649-6652 (2002).
Vasilevich et al. Selective conversion of O-succinimidyl carbamates to N-(O-carbamoyl)-succinmonoamides and Ureas. Tetrahedron Letters 43(18):3443-3445 (2002).

LP-PLA2 INHIBITORS

CROSS-REFERENCE

This application is filed pursuant to 35 U.S.C. § 371 as a United States National Phase Application of International Application No. PCT/US2016/054541, filed Sep. 29, 2016, which claims the benefit of U.S. Provisional Application No. 62/236,716, filed on Oct. 2, 2015, each of which are herein incorporated by reference in their entirety.

BACKGROUND

Lipoprotein-associated phospholipase A2 (Lp-PLA2) is a constitutively active, secreted serine hydrolase enzyme encoded by the PLA2G7 gene that degrades a wide range of phospholipids through phospholipase A2 activity. This enzyme employs a nucleophilic serine residue to remove the sn2 acyl groups on phospholipids to release a free fatty acid and a lysophospholipid. Substrates of Lp-PLA2 include 1-alkyl-2-acetyl-sn-glycero-3-phosphocholines, also referred to as platelet-activating factor (PAF), and 1-acyl-2-acetyl-sn-glycero-3-phosphocholines, both of which initiate inflammatory signaling pathways. Lp-PLA2 is also capable of cleaving oxidized and truncated fatty acid acyl groups from phosphatidylcholine lipids found in oxidized LDL particles. This action produces pro-inflammatory lysophosphatidylcholines (LPC) and oxidized fatty acids. Because many of the substrates of Lp-PLA2 activate the platelet-activating factor receptor (PAF-R), a G-protein coupled receptor that mediates a wide range of physiological processes and diseases, including inflammation, asthma, autoimmunity, and tumor growth, Lp-PLA2 is thought to regulate these processes through its biochemical control of endogenous pools of PAF-R ligands. Therefore, Lp-PLA2 inhibition is a viable mechanism to target a number of diseases.

SUMMARY OF THE INVENTION

This disclosure provides, for example, compounds and compositions which are modulators of Lp-PLA2, and their use as medicinal agents, processes for their preparation, and pharmaceutical compositions that include disclosed compounds as at least one active ingredient. The disclosure also provides for the use of disclosed compounds as medicaments and/or in the manufacture of medicaments for the inhibition of Lp-PLA2 activity in warm-blooded animals such as humans.

The serine hydrolase α-β-hydrolase domain 6 (ABHD6) is another lipid mediator. This disclosure provides, for example, compounds and compositions which are modulators of ABHD6, and their use as medicinal agents, processes for their preparation, and pharmaceutical compositions that include disclosed compounds as at least one active ingredient. The disclosure also provides for the use of disclosed compounds as medicaments and/or in the manufacture of medicaments for the inhibition of ABHD6 activity in warm-blooded animals such as humans.

In one embodiment is a compound of Formula (I), or a pharmaceutically acceptable salt or solvate thereof:

Formula (I)

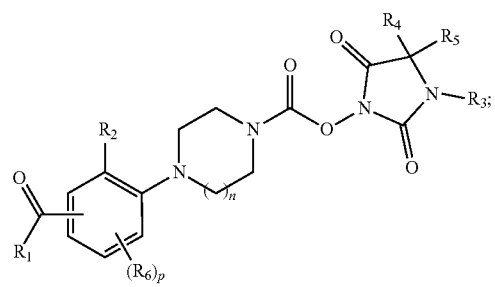

wherein:

$R_1$ is selected from the group consisting of $-N(R_{10})R_{11}$, $-OH$, $C_1$-$C_6$alkyl, and $C_1$-$C_6$alkoxy;

$R_2$ is selected from the group consisting of hydrogen, halogen, $-N(R_{12})R_{13}$, $-CF_3$, $C_1$-$C_6$alkyl, and $C_1$-$C_6$alkoxy;

$R_3$ is hydrogen or $C_1$-$C_3$alkyl;

$R_4$ and $R_5$ are each independently selected from the group consisting of hydrogen, $C_1$-$C_6$alkyl optionally substituted by one, two, or three groups independently selected from halogen, cyano, and hydroxyl, and $-(C_1$-$C_6$alkylene)-(phenyl) optionally substituted by one, two, or three groups independently selected from halogen, cyano, $-CF_3$, $-OH$, $C_1$-$C_6$alkyl, and $C_1$-$C_6$alkoxy;

each $R_6$ is independently selected from the group consisting of halogen, $-N(R_{12})R_{13}$, $-CF_3$, $C_1$-$C_6$alkyl, and $C_1$-$C_6$alkoxy;

$R_{10}$ and $R_{11}$ are each independently selected from the group consisting of hydrogen, and $C_1$-$C_3$alkyl; or $R_{10}$ and $R_{11}$ together with the nitrogen atom to which they are attached, form a 4-6 membered heterocyclic ring optionally substituted by $C_1$-$C_6$alkyl or $-CO_2H$;

each $R_{12}$ and $R_{13}$ are each independently selected from the group consisting of hydrogen, and $C_1$-$C_3$alkyl;

n is 1 or 2; and p is 0, 1, or 2.

In some embodiments is a compound of Formula (I), or a pharmaceutically acceptable salt or solvate thereof, wherein $R_2$ is hydrogen or halogen. In some embodiments is a compound of Formula (I), or a pharmaceutically acceptable salt or solvate thereof, wherein $R_1$ is selected from the group consisting of $-N(R_{10})R_{11}$, $C_1$-$C_6$alkyl, and $C_1$-$C_6$alkoxy. In some embodiments is a compound of Formula (I), or a pharmaceutically acceptable salt or solvate thereof, wherein $R_1$ is $-OH$. In some embodiments is a compound of Formula (I), or a pharmaceutically acceptable salt or solvate thereof, wherein $R_1$ is $-N(R_{10})R_{11}$. In some embodiments is a compound of Formula (I), or a pharmaceutically acceptable salt or solvate thereof, wherein $R_{10}$ and $R_{11}$ are each hydrogen. In some embodiments is a compound of Formula (I), or a pharmaceutically acceptable salt or solvate thereof, wherein $R_{10}$ and $R_{11}$ are each $C_1$-$C_3$alkyl. In some embodiments is a compound of Formula (I), or a pharmaceutically acceptable salt or solvate thereof, wherein $R_{10}$ and $R_{11}$ are each $-CH_3$. In some embodiments is a compound of Formula (I), or a pharmaceutically acceptable salt or solvate thereof, wherein $R_{10}$ and $R_{11}$ together with the nitrogen atom to which they are attached, form a 4-6 membered heterocyclic ring optionally substituted by $C_1$-$C_6$alkyl or $-CO_2H$. In some embodiments is a compound of Formula (I), or a pharmaceutically acceptable salt or solvate thereof, wherein $R_{10}$ and $R_{11}$ together with the nitrogen atom to which they are attached, form an unsubstituted pyrrolidine ring. In some embodiments is a compound of Formula (I), or a pharmaceutically acceptable salt or solvate thereof, wherein $R_{10}$ and $R_{11}$ together with the nitrogen atom to which they are attached, form an unsubstituted piperidine ring. In some embodiments is a compound of Formula (I), or a pharmaceutically acceptable salt or solvate thereof, wherein $R_{10}$ and $R_{11}$ together with the nitrogen atom to which they are attached, form a piperidine ring substituted by —$CO_2H$. In some embodiments is a compound of Formula (I), or a pharmaceutically acceptable salt or solvate thereof, wherein $R_{10}$ and $R_{11}$ together with the nitrogen atom to which they are attached, form a piperazine ring optionally substituted by $C_1$-$C_6$alkyl. In some embodiments is a compound of Formula (I), or a pharmaceutically acceptable salt or solvate thereof, wherein $R_4$ is hydrogen. In some embodiments is a compound of Formula (I), or a pharmaceutically acceptable salt or solvate thereof, wherein $R_5$ is $C_{1-6}$alkyl optionally substituted by one, two, or three groups independently selected from halogen, cyano, phenyl, and hydroxyl. In some embodiments is a compound of Formula (I), or a pharmaceutically acceptable salt or solvate thereof, wherein $R_5$ is unsubstituted $C_{1-6}$alkyl. In some embodiments is a compound of Formula (I), or a pharmaceutically acceptable salt or solvate thereof, wherein $R_5$ is —$CH(CH_3)_2$. In some embodiments is a compound of Formula (I), or a pharmaceutically acceptable salt or solvate thereof, wherein $R_5$ is unsubstituted —$CH_2$-phenyl. In some embodiments is a compound of Formula (I), or a pharmaceutically acceptable salt or solvate thereof, wherein $R_4$ is hydrogen. In some embodiments is a compound of Formula (I), or a pharmaceutically acceptable salt or solvate thereof, wherein $R_5$ is —($C_1$-$C_2$alkylene)-(phenyl) substituted by one, two, or three groups independently selected from halogen, cyano, —$CF_3$, —OH, $C_1$-$C_6$alkyl, and $C_1$-$C_6$alkoxy. In some embodiments is a compound of Formula (I), or a pharmaceutically acceptable salt or solvate thereof, wherein $R_3$ is hydrogen. In some embodiments is a compound of Formula (I), or a pharmaceutically acceptable salt or solvate thereof, wherein $R_3$ is —$CH_3$. In some embodiments is a compound of Formula (I), or a pharmaceutically acceptable salt or solvate thereof, wherein n is 1. In some embodiments is a compound of Formula (I), or a pharmaceutically acceptable salt or solvate thereof, wherein n is 2. In some embodiments is a compound of Formula (I), or a pharmaceutically acceptable salt or solvate thereof, wherein p is 1. In some embodiments is a compound of Formula (I), or a pharmaceutically acceptable salt or solvate thereof, wherein p is 0. In some embodiments is a compound of Formula (I), or a pharmaceutically acceptable salt or solvate thereof, wherein $R_2$ is hydrogen. In some embodiments is a compound of Formula (I), or a pharmaceutically acceptable salt or solvate thereof, wherein $R_2$ is halogen. In some embodiments is a compound of Formula (I), or a pharmaceutically acceptable salt or solvate thereof, wherein $R_2$ is —Cl.

In another embodiment is a compound of Formula (II), or a pharmaceutically acceptable salt or solvate thereof:

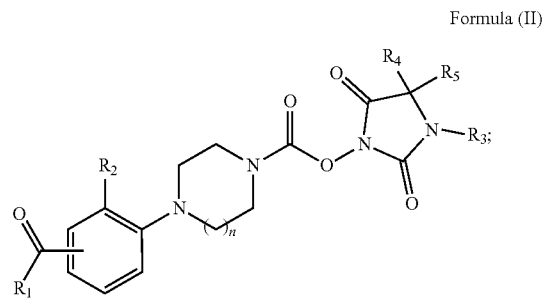

Formula (II)

wherein:
$R_1$ is selected from the group consisting of —$N(R_{10})R_{11}$, —OH, $C_1$-$C_6$alkyl, and $C_1$-$C_6$alkoxy;
$R_2$ is hydrogen or halogen;
$R_3$ is hydrogen or $C_1$-$C_3$alkyl;
$R_4$ and $R_5$ are each independently selected from the group consisting of hydrogen, $C_1$-$C_6$alkyl optionally substituted by one, two, or three groups independently selected from halogen, cyano, and hydroxyl, and —($C_1$-$C_6$alkylene)-(phenyl) optionally substituted by one, two, or three groups independently selected from halogen, cyano, —$CF_3$, —OH, $C_1$-$C_6$alkyl, and $C_1$-$C_6$alkoxy;
$R_{10}$ and $R_{11}$ are each independently selected from the group consisting of hydrogen, and $C_1$-$C_3$alkyl; or $R_{10}$ and $R_{11}$ together with the nitrogen atom to which they are attached, form a 4-6 membered heterocyclic ring optionally substituted by $C_1$-$C_6$alkyl or —$CO_2H$; and
n is 1 or 2.

In some embodiments is a compound of Formula (II), or a pharmaceutically acceptable salt or solvate thereof, wherein $R_1$ is —$N(R_{10})R_{11}$. In some embodiments is a compound of Formula (II), or a pharmaceutically acceptable salt or solvate thereof, wherein $R_{10}$ and $R_{11}$ are each hydrogen. In some embodiments is a compound of Formula (II), or a pharmaceutically acceptable salt or solvate thereof, wherein $R_{10}$ and $R_{11}$ are each $C_1$-$C_3$alkyl. In some embodiments is a compound of Formula (II), or a pharmaceutically acceptable salt or solvate thereof, wherein $R_{10}$ and $R_{11}$ are each —$CH_3$. In some embodiments is a compound of Formula (II), or a pharmaceutically acceptable salt or solvate thereof, wherein $R_{10}$ and $R_{11}$ together with the nitrogen atom to which they are attached, form a 4-6 membered heterocyclic ring optionally substituted by $C_1$-$C_6$alkyl or —$CO_2H$. In some embodiments is a compound of Formula (II), or a pharmaceutically acceptable salt or solvate thereof, wherein $R_{10}$ and $R_{11}$ together with the nitrogen atom to which they are attached, form an unsubstituted pyrrolidine ring. In some embodiments is a compound of Formula (II), or a pharmaceutically acceptable salt or solvate thereof, wherein $R_{10}$ and $R_{11}$ together with the nitrogen atom to which they are attached, form an unsubstituted piperidine ring. In some embodiments is a compound of Formula (II), or a pharmaceutically acceptable salt or solvate thereof, wherein $R_{10}$ and $R_{11}$ together with the nitrogen atom to which they are attached, form a piperidine ring substituted by —$CO_2H$. In some embodiments is a compound of Formula (II), or a pharmaceutically acceptable salt or solvate thereof, wherein $R_{10}$ and $R_{11}$ together with the nitrogen atom to which they are attached, form a piperazine ring optionally substituted by $C_1$-$C_6$alkyl. In some embodiments is a compound of Formula (II), or a pharmaceutically acceptable salt or solvate thereof, wherein $R_4$ is hydrogen. In some embodiments is a compound of Formula (II), or a pharmaceutically acceptable salt or solvate thereof, wherein $R_5$ is $C_{1-6}$alkyl optionally substituted by one, two, or three groups selected from halogen, cyano, phenyl, and hydroxyl. In some embodiments is a compound of Formula (II), or a pharmaceutically acceptable salt or solvate thereof, wherein $R_5$ is unsubstituted $C_{1-6}$alkyl. In some embodiments is a compound of Formula (II), or a pharmaceutically acceptable salt or solvate thereof, wherein $R_5$ is —CH(CH$_3$)$_2$. In some embodiments is a compound of Formula (II), or a pharmaceutically acceptable salt or solvate thereof, wherein $R_5$ is unsubstituted —CH$_2$-phenyl. In some embodiments is a compound of Formula (II), or a pharmaceutically acceptable salt or solvate thereof, wherein $R_4$ is hydrogen. In some embodiments is a compound of Formula (II), or a pharmaceutically acceptable salt or solvate thereof, wherein $R_5$ is —(C$_1$-C$_2$alkylene)-(phenyl) substituted by one, two, or three groups independently selected from halogen, cyano, —CF$_3$, —OH, C$_1$-C$_6$alkyl, and C$_1$-C$_6$alkoxy. In some embodiments is a compound of Formula (II), or a pharmaceutically acceptable salt or solvate thereof, wherein $R_3$ is hydrogen. In some embodiments is a compound of Formula (II), or a pharmaceutically acceptable salt or solvate thereof, wherein $R_3$ is —CH$_3$. In some embodiments is a compound of Formula (II), or a pharmaceutically acceptable salt or solvate thereof, wherein n is 1. In some embodiments is a compound of Formula (II), or a pharmaceutically acceptable salt or solvate thereof, wherein n is 2. In some embodiments is a compound of Formula (II), or a pharmaceutically acceptable salt or solvate thereof, wherein $R_2$ is hydrogen. In some embodiments is a compound of Formula (II), or a pharmaceutically acceptable salt or solvate thereof, wherein $R_2$ is halogen. In some embodiments is a compound of Formula (II), or a pharmaceutically acceptable salt or solvate thereof, wherein $R_2$ is —Cl.

In another embodiment, provided herein is a pharmaceutical composition comprising a compound of Formula (I), or a pharmaceutically acceptable salt or solvate thereof, and a pharmaceutically acceptable diluent, excipient or binder. In one embodiment, the pharmaceutical composition comprising the compound of Formula (I), or a pharmaceutically acceptable salt or solvate thereof, is formulated for a route of administration selected from oral administration, parenteral administration, buccal administration, nasal administration, topical administration, and rectal administration.

In another embodiment, provided herein is a pharmaceutical composition comprising a compound of Formula (II), or a pharmaceutically acceptable salt or solvate thereof, and a pharmaceutically acceptable diluent, excipient or binder. In one embodiment, the pharmaceutical composition comprising the compound of Formula (II), or a pharmaceutically acceptable salt or solvate thereof, is formulated for a route of administration selected from oral administration, parenteral administration, buccal administration, nasal administration, topical administration, and rectal administration.

Disclosed herein is a compound of Formula (I), or a pharmaceutically acceptable salt or solvate thereof, for use as a medicament. Further disclosed herein is a compound of Formula (I), or a pharmaceutically acceptable salt or solvate thereof, for use in a method of treating ischemia, traumatic brain injury, multiple sclerosis, diabetes, Alzheimer's disease, Parkinson's disease, amyotrophic lateral sclerosis (ALS), or cancer. Also disclosed herein is a compound of Formula (II), or a pharmaceutically acceptable salt or solvate thereof, for use as a medicament. Further disclosed herein is a compound of Formula (II), or a pharmaceutically acceptable salt or solvate thereof, for use in a method of treating ischemia, traumatic brain injury, multiple sclerosis, diabetes, Alzheimer's disease, Parkinson's disease, amyotrophic lateral sclerosis (ALS), or cancer.

Further disclosed herein is a pharmaceutical composition comprising a compound of Formula (I), or a pharmaceutically acceptable salt or solvate thereof, for use in a method of treating ischemia, traumatic brain injury, multiple sclerosis, diabetes, Alzheimer's disease, Parkinson's disease, amyotrophic lateral sclerosis (ALS), or cancer. Also disclosed herein is a pharmaceutical composition comprising a compound of Formula (II), or a pharmaceutically acceptable salt or solvate thereof, for use in a method of treating ischemia, traumatic brain injury, multiple sclerosis, diabetes, Alzheimer's disease, Parkinson's disease, amyotrophic lateral sclerosis (ALS), or cancer.

In another embodiment is a method of treating a disease, disorder or condition in a mammal that would benefit from Lp-PLA2 inhibition comprising administering to the mammal a therapeutically effective amount of a compound of Formula (I), or a pharmaceutically acceptable salt or solvate thereof.

In another embodiment is a method of treating a disease, disorder or condition in a mammal that would benefit from Lp-PLA2 inhibition comprising administering to the mammal a therapeutically effective amount of a compound of Formula (II), or a pharmaceutically acceptable salt or solvate thereof.

In another embodiment is a method of treating a disease, disorder or condition in a mammal that would benefit from Lp-PLA2 inhibition comprising administering to the mammal a therapeutically effective amount of a compound of Formula (I), or a pharmaceutically acceptable salt or solvate thereof, wherein the disease, disorder or condition in a mammal is selected from ischemia, traumatic brain injury, multiple sclerosis, diabetes, Alzheimer's disease, Parkinson's disease, amyotrophic lateral sclerosis (ALS), and cancer.

In another embodiment is a method of treating a disease, disorder or condition in a mammal that would benefit from Lp-PLA2 inhibition comprising administering to the mammal a therapeutically effective amount of a compound of Formula (II), or a pharmaceutically acceptable salt or solvate thereof; wherein the disease, disorder or condition in a mammal is selected from ischemia, traumatic brain injury, multiple sclerosis, diabetes, Alzheimer's disease, Parkinson's disease, amyotrophic lateral sclerosis (ALS), and cancer.

DETAILED DESCRIPTION OF THE INVENTION

The ability of Lp-PLA2 to both produce and degrade pro-inflammatory lipids suggests that inhibitors of this enzyme can allow context-dependent modulation of inflammatory tone. Because Lp-PLA2 is highly expressed in numerous immune cell types including monocytes, macrophages, T cells, mast cells and microglia, Lp-PLA2 inhibitors can also find utility in treating conditions where these cell populations are aberrantly regulated. Given the preference of Lp-PLA2 for oxidized phospholipids, inhibition of the Lp-PLA2 enzyme can be useful for treatment of diseases where oxidative stress and phospholipid oxidation is integral to disease progression. For conditions where this has been observed, such as ischemia, traumatic brain injury, multiple sclerosis, and diabetes, Lp-PLA2 inhibitors can mitigate inflammatory injury through the suppression of pro-inflammatory (e.g. LPC) lipid production. The high expression of PLA2G7 in the brain also suggests that Lp-PLA2 inhibition can be protective in neurodegenerative diseases, including Alzheimer's disease, Parkinson's disease, and amyotrophic lateral sclerosis (ALS), which are thought to be driven or exacerbated by oxidative damage to neurons, glia or surrounding tissue. Lp-PLA2 levels have also been found to be elevated in prostate cancer and, furthermore, genetic blockade of this enzyme sensitizes cancer cells to oxidative stress and promotes apoptosis. Thus, Lp-PLA2 inhibitors can also prove beneficial in the treatment of cancer.

Definitions

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, "consist of" or "consist essentially of" the described features.

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In certain embodiments, an alkenyl comprises two to six carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In certain embodiments, an alkynyl comprises two to six carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —$OR^a$, —$SR^a$, —$OC(O)R^a$, —$N(R^a)_2$, —$C(O)R^a$, —$C(O)OR^a$, —$C(O)N(R^a)_2$, —$N(R^a)C(O)OR^f$, —$OC(O)$—$NR^aR^f$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2) and —$S(O)_tN(R^a)_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each $R^f$ is independently alkyl, fluoroalkyl, carbocyclyl, carbocyclylalkyl, aryl, aralkyl, heterocyclyl, heterocyclylalkyl, heteroaryl or heteroarylalkyl.

"Aminoalkyl" refers to a radical of the formula —$R^c$—$N(R^a)_2$, where each $R^c$ is independently an alkylene chain as defined above, for example, methylene, ethylene, and the like; and each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)$ $R^a$, —$R^b$—$C(O)OR^a$, —$R^b$—$C(O)N(R^a)_2$, —$R^b$—O—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aryloxy" refers to a radical bonded through an oxygen atom of the formula —O-aryl, where aryl is as defined above.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated, (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O) $R^a$, —$R^b$—C(O)$OR^a$, —$R^b$—C(O)N$(R^a)_2$, —$R^b$—O—$R^c$—C(O)N$(R^a)_2$, —$R^b$—N$(R^a)$C(O)$OR^a$, —$R^b$—N$(R^a)$C(O)$R^a$, —$R^b$—N$(R^a)$S(O)$_tR^a$ (where t is 1 or 2), —$R^b$—S(O)$_tOR^a$ (where t is 1 or 2), —$R^b$—S(O)$_tR^a$ (where t is 1 or 2) and —$R^b$—S(O)$_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above. "(Cycloalkyl)alkyl" refers to a carbocyclylalkyl radical wherein the carbocyclyl radical is fully saturated.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Haloalkyl" refers to an alkyl radical, as defined above, that is substituted by one or more halogen radicals, as defined above, for example, trifluoromethyl, chloroethyl, and the like. The alkyl part of the haloalkyl radical is optionally substituted as defined above for an alkyl group.

"Heterocyclyl", i.e. heterocyclic ring, refers to a stable 5- to 18-membered non-aromatic ring radical that comprises one to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which includes fused or bridged ring systems. The heteroatoms in the heterocyclyl radical are optionally oxidized. One or more nitrogen atoms, if present, are optionally quaternized. The heterocyclyl radical is partially or fully saturated. In some embodiments, the heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)N$(R^a)_2$, —$R^b$—O—$R^c$—C(O)N$(R^a)_2$, —$R^b$—N$(R^a)$C(O)$OR^a$, —$R^b$—N$(R^a)$C(O)$R^a$, —$R^b$—N$(R^a)$S(O)$_tR^a$ (where t is 1 or 2), —$R^b$—S(O)$_tOR^a$ (where t is 1 or 2), —$R^b$—S(O)$_tR^a$ (where t is 1 or 2) and —$R^b$—S(O)$_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Unless stated otherwise specifically in the specification, the term "heteroaryl" is meant to include heteroaryl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$-N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$-N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O— heteroaryl, where heteroaryl is as defined above.

"Heteroarylalkyl" refers to a radical of the formula —R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

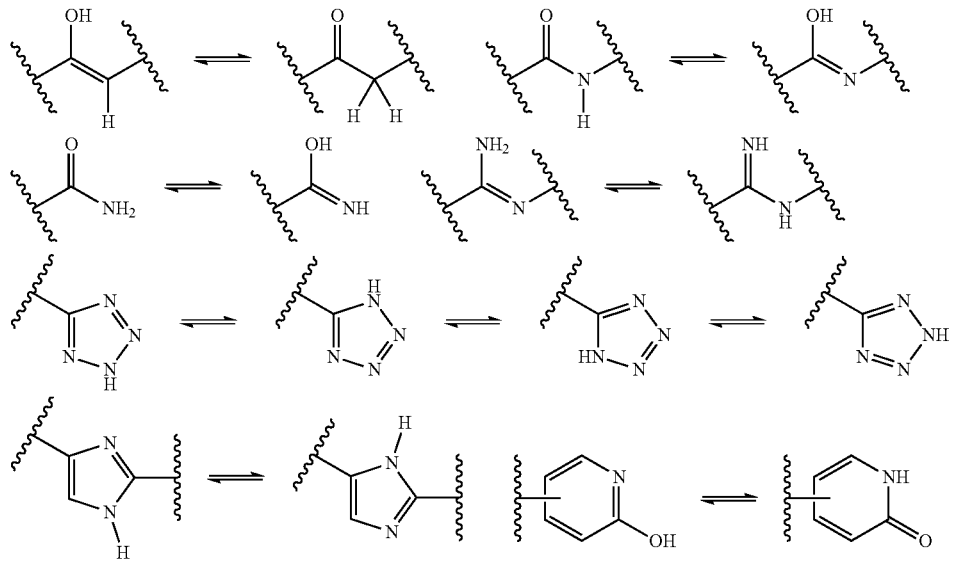

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution. "Optionally substituted" and "substituted or unsubstituted" and "unsubstituted or substituted" are used interchangeably herein.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and, aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

An "effective amount" or "therapeutically effective amount" refers to an amount of a compound administered to a mammalian subject, either as a single dose or as part of a series of doses, which is effective to produce a desired therapeutic effect.

As used herein, "treatment" or "treating" or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has been made.

Compounds

Compounds described herein are Lp-PLA2 inhibitors. Compounds described herein are also ABHD6 modulators. These compounds, and compositions comprising these compounds, are useful for the treatment of ischemia, traumatic brain injury, multiple sclerosis, diabetes, Alzheimer's disease, Parkinson's disease, amyotrophic lateral sclerosis (ALS), and cancer.

In one embodiment is a compound of Formula (I), or a pharmaceutically acceptable salt or solvate thereof:

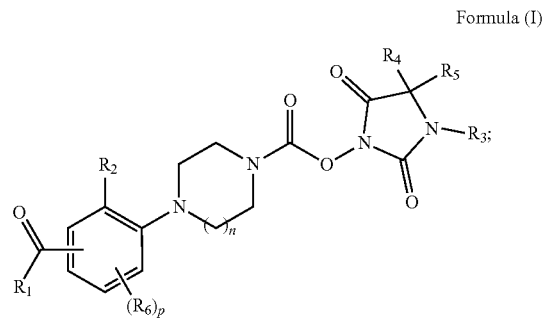

Formula (I)

wherein:

$R_1$ is selected from the group consisting of —$N(R_{10})R_{11}$, —OH, $C_1$-$C_6$alkyl, and $C_1$-$C_6$alkoxy;

$R_2$ is selected from the group consisting of hydrogen, halogen, —$N(R_{12})R_{13}$, —$CF_3$, $C_1$-$C_6$alkyl, and $C_1$-$C_6$alkoxy;

$R_3$ is hydrogen or $C_1$-$C_3$alkyl;

$R_4$ and $R_5$ are each independently selected from the group consisting of hydrogen, $C_1$-$C_6$alkyl optionally substituted by one, two, or three groups independently selected from halogen, cyano, and hydroxyl, and —($C_1$-$C_6$alkylene)-(phenyl) optionally substituted by one, two, or three groups independently selected from halogen, cyano, —$CF_3$, —OH, $C_1$-$C_6$alkyl, and $C_1$-$C_6$alkoxy;

each $R_6$ is independently selected from the group consisting of halogen, —$N(R_{12})R_{13}$, —$CF_3$, $C_1$-$C_6$alkyl, and $C_1$-$C_6$alkoxy;

$R_{10}$ and $R_{11}$ are each independently selected from the group consisting of hydrogen, and $C_1$-$C_3$alkyl; or $R_{10}$ and $R_{11}$ together with the nitrogen atom to which they are attached, form a 4-6 membered heterocyclic ring optionally substituted by $C_1$-$C_6$alkyl or —$CO_2H$;

$R_{12}$ and $R_{13}$ are each independently selected from the group consisting of hydrogen, and $C_1$-$C_3$alkyl;

n is 1 or 2; and p is 0, 1, or 2.

In some embodiments is a compound of Formula (I), wherein $R_1$ is —$N(R_{10})R_{11}$. In some embodiments is a compound of Formula (I), wherein $R_1$ is —$N(R_{10})R_{11}$, and $R_{10}$ and $R_{11}$ are each independently selected from the group consisting of hydrogen and $C_1$-$C_3$alkyl. In some embodiments is a compound of Formula (I), wherein $R_1$ is —$N(R_{10})R_{11}$, and $R_{10}$ and $R_{11}$ are each hydrogen. In some embodiments is a compound of Formula (I), wherein $R_1$ is —$N(R_{10})R_{11}$, $R_{10}$ is $C_1$-$C_3$alkyl, and $R_{11}$ is hydrogen. In some embodiments is a compound of Formula (I), wherein $R_1$ is —$N(R_{10})R_{11}$, and $R_{10}$ and $R_{11}$ are each $C_1$-$C_3$alkyl.

In some embodiments is a compound of Formula (I), wherein $R_1$ is —$N(R_{10})R_{11}$, and $R_{10}$ and $R_{11}$ together with the nitrogen atom to which they are attached, form a 4-6 membered heterocyclic ring optionally substituted by $C_1$-$C_6$alkyl or —$CO_2H$. In some embodiments is a compound of Formula (I), wherein $R_1$ is —$N(R_{10})R_{11}$, and $R_{10}$ and $R_{11}$ together with the nitrogen atom to which they are attached, form a pyrrolidine ring optionally substituted by $C_1$-$C_6$alkyl or —$CO_2H$. In some embodiments is a compound of Formula (I), wherein $R_1$ is —$N(R_{10})R_{11}$, and $R_{10}$ and $R_{11}$ together with the nitrogen atom to which they are attached, form an unsubstituted pyrrolidine ring. In some embodiments is a compound of Formula (I), wherein $R_1$ is —$N(R_{10})R_{11}$, and $R_{10}$ and $R_{11}$ together with the nitrogen atom to which they are attached, form a pyrrolidine ring substituted by $C_1$-$C_6$alkyl. In some embodiments is a compound of Formula (I), wherein $R_1$ is —$N(R_{10})R_{11}$, and $R_{10}$ and $R_{11}$ together with the nitrogen atom to which they are attached, form a pyrrolidine ring substituted by —$CO_2H$. In some embodiments is a compound of Formula (I), wherein $R_1$ is —$N(R_{10})R_{11}$, and $R_{10}$ and $R_{11}$ together with the nitrogen atom to which they are attached, form a piperidine ring optionally substituted by $C_1$-$C_6$alkyl or —$CO_2H$. In some embodiments is a compound of Formula (I), wherein $R_1$ is —$N(R_{10})R_{11}$, and $R_{10}$ and $R_{11}$ together with the nitrogen atom to which they are attached, form an unsubstituted piperidine ring. In some embodiments is a compound of Formula (I), wherein $R_1$ is —$N(R_{10})R_{11}$, and $R_{10}$ and $R_{11}$ together with the nitrogen atom to which they are attached, form a piperidine ring substituted by $C_1$-$C_6$alkyl. In some embodiments is a compound of Formula (I), wherein $R_1$ is —$N(R_{10})R_{11}$, and $R_{10}$ and $R_{11}$ together with the nitrogen atom to which they are attached, form a piperidine ring substituted by —$CO_2H$. In some embodiments is a compound of Formula (I), wherein $R_1$ is —$N(R_{10})R_{11}$, and $R_{10}$ and $R_{11}$ together with the nitrogen atom to which they are attached, form a piperazine ring optionally substituted by $C_1$-$C_6$alkyl. In some embodiments is a compound of Formula (I), wherein $R_1$ is —$N(R_{10})R_{11}$, and $R_{10}$ and $R_{11}$ together with the nitrogen atom to which they are attached, form an unsubstituted piperazine ring. In some embodiments is a compound of Formula (I), wherein $R_1$ is —$N(R_{10})R_{11}$, and $R_{10}$ and $R_{11}$ together with the nitrogen atom to which they are attached, form a piperazine ring substituted by $C_1$-$C_6$alkyl. In some embodiments is a compound of Formula (I), wherein $R_1$ is —$N(R_{10})R_{11}$, and $R_{10}$ and $R_{11}$ together with the nitrogen atom to which they are attached, form an unsubstituted morpholine ring.

In some embodiments is a compound of Formula (I), wherein $R_2$ is selected from the group consisting of hydrogen, halogen, —$N(R_{12})R_{13}$, —$CF_3$, $C_1$-$C_6$alkyl, and $C_1$-$C_6$alkoxy. In some embodiments is a compound of Formula (I), wherein $R_2$ is hydrogen. In some embodiments is a compound of Formula (I), wherein $R_2$ is halogen. In some embodiments is a compound of Formula (I), wherein $R_2$ is F. In some embodiments is a compound of Formula (I), wherein $R_2$ is Cl. In some embodiments is a compound of Formula (I), wherein $R_2$ is Br. In some embodiments is a compound of Formula (I), wherein $R_2$ is —$CF_3$. In some embodiments is a compound of Formula (I), wherein $R_2$ is $C_1$-$C_6$alkyl. In some embodiments is a compound of Formula (I), wherein $R_2$ is $C_1$-$C_6$alkoxy.

In some embodiments is a compound of Formula (I), wherein p is 0. In some embodiments is a compound of Formula (I), wherein p is 1. In some embodiments is a compound of Formula (I), wherein p is 1 and $R_6$ is selected from the group consisting of halogen, —$N(R_{12})R_{13}$, —$CF_3$, $C_1$-$C_6$alkyl, and $C_1$-$C_6$alkoxy. In some embodiments is a compound of Formula (I), wherein p is 1 and $R_6$ is halogen. In some embodiments is a compound of Formula (I), wherein p is 1 and $R_6$ is —$CF_3$. In some embodiments is a compound of Formula (I), wherein p is 1 and $R_6$ is $C_1$-$C_6$alkyl. In some embodiments is a compound of Formula (I), wherein p is 1 and $R_6$ is $C_1$-$C_6$alkoxy. In some embodiments is a compound of Formula (I), wherein p is 2. In some embodiments is a compound of Formula (I), wherein p is 2 and $R_6$ is independently selected from the group consisting of halogen, —$N(R_{12})R_{13}$, —$CF_3$, $C_1$-$C_6$alkyl, and $C_1$-$C_6$alkoxy. In some embodiments is a compound of Formula (I), wherein n is 1. In some embodiments is a compound of Formula (I), wherein n is 2.

In some embodiments is a compound of Formula (I), wherein $R_4$ and $R_5$ are each independently selected from the group consisting of hydrogen, $C_1$-$C_6$alkyl optionally substituted by one, two, or three groups independently selected from halogen, cyano, and hydroxyl, and —($C_1$-$C_6$alkylene)-(phenyl) optionally substituted by one, two, or three groups independently selected from halogen, cyano, —$CF_3$, —OH, $C_1$-$C_6$alkyl, and $C_1$-$C_6$alkoxy. In some embodiments is a compound of Formula (I), wherein $R_4$ is hydrogen and $R_5$ is selected from the group consisting of hydrogen, $C_1$-$C_6$alkyl optionally substituted by one, two, or three groups independently selected from halogen, cyano, and hydroxyl, and —($C_1$-$C_6$alkylene)-(phenyl) optionally substituted by one, two, or three groups independently selected from halogen, cyano, —$CF_3$, —OH, $C_1$-$C_6$alkyl, and $C_1$-$C_6$alkoxy. In some embodiments is a compound of Formula (I), wherein $R_4$ is hydrogen and $R_5$ is hydrogen. In some embodiments is a compound of Formula (I), wherein $R_4$ is hydrogen and $R_5$ is $C_1$-$C_6$alkyl optionally substituted by one, two, or three groups independently selected from halogen, cyano, and hydroxyl. In some embodiments is a compound of Formula (I), wherein $R_4$ is hydrogen and $R_5$ is unsubstituted $C_1$-$C_6$alkyl. In some embodiments is a compound of Formula (I), wherein $R_4$ is hydrogen and $R_5$ is —($C_1$-$C_6$alkylene)-(phenyl) optionally substituted by one, two, or three groups independently selected from halogen, cyano, —$CF_3$, —OH, $C_1$-$C_6$alkyl, and $C_1$-$C_6$alkoxy. In some embodiments is a compound of Formula (I), wherein $R_4$ is hydrogen and $R_5$ is unsubstituted —($C_1$-$C_6$alkylene)-(phenyl). In some embodiments is a compound of Formula (I), wherein $R_4$ is hydrogen and $R_5$ is unsubstituted —($CH_2$)-(phenyl). In some embodiments is a compound of Formula (I), wherein $R_4$ is hydrogen and $R_5$ is —($C_1$-$C_6$alkylene)-(phenyl) substituted by one, two, or three groups independently selected from halogen, cyano, —CF$_3$, —OH, C$_1$-C$_6$alkyl, and C$_1$-C$_6$alkoxy. In some embodiments is a compound of Formula (I), wherein R$_4$ is hydrogen and R$_5$ is —(C$_1$-C$_6$alkylene)-(phenyl) substituted by one halogen. In some embodiments is a compound of Formula (I), wherein R$_4$ is hydrogen and R$_5$ is —(C$_1$-C$_6$alkylene)-(phenyl) substituted by one —CF$_3$. In some embodiments is a compound of Formula (I), wherein R$_4$ is hydrogen and R$_5$ is —(C$_1$-C$_6$alkylene)-(phenyl) substituted by one C$_1$-C$_6$alkyl. In some embodiments is a compound of Formula (I), wherein R$_4$ is hydrogen and R$_5$ is —(C$_1$-C$_6$alkylene)-(phenyl) substituted by one C$_1$-C$_6$alkoxy.

In some embodiments is a compound of Formula (I), wherein R$_3$ is hydrogen or C$_1$-C$_3$alkyl. In some embodiments is a compound of Formula (I), wherein R$_3$ is hydrogen. In some embodiments is a compound of Formula (I), wherein R$_3$ is C$_1$-C$_3$alkyl. In some embodiments is a compound of Formula (I), wherein R$_3$ is —CH$_3$.

In another embodiment is a compound of Formula (II), or a pharmaceutically acceptable salt or solvate thereof:

Formula (II)

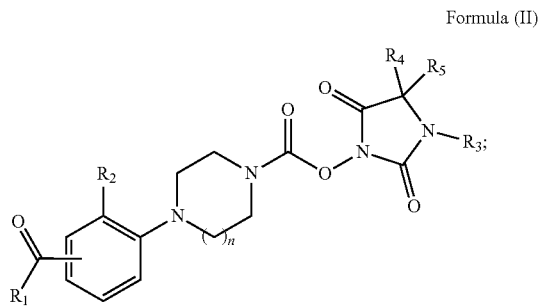

wherein:
R$_1$ is selected from the group consisting of —N(R$_{10}$)R$_{11}$, —OH, C$_1$-C$_6$alkyl, and C$_1$-C$_6$alkoxy;
R$_2$ is hydrogen or halogen;
R$_3$ is hydrogen or C$_1$-C$_3$alkyl;
R$_4$ and R$_5$ are each independently selected from the group consisting of hydrogen, C$_1$-C$_6$alkyl optionally substituted by one, two, or three groups independently selected from halogen, cyano, and hydroxyl, and —(C$_1$-C$_6$alkylene)-(phenyl) optionally substituted by one, two, or three groups independently selected from halogen, cyano, —CF$_3$, —OH, C$_1$-C$_6$alkyl, and C$_1$-C$_6$alkoxy;
R$_{10}$ and R$_{11}$ are each independently selected from the group consisting of hydrogen, and C$_1$-C$_3$alkyl; or R$_{10}$ and R$_{11}$ together with the nitrogen atom to which they are attached, form a 4-6 membered heterocyclic ring optionally substituted by C$_1$-C$_6$alkyl or —CO$_2$H; and
n is 1 or 2.

In some embodiments is a compound of Formula (II), wherein R$_1$ is —N(R$_{10}$)R$_{11}$. In some embodiments is a compound of Formula (II), wherein R$_1$ is —N(R$_{10}$)R$_{11}$, and R$_{10}$ and R$_{11}$ are each independently selected from the group consisting of hydrogen and C$_1$-C$_3$alkyl. In some embodiments is a compound of Formula (II), wherein R$_1$ is —N(R$_{10}$)R$_{11}$, and R$_{10}$ and R$_{11}$ are each hydrogen. In some embodiments is a compound of Formula (II), wherein R$_1$ is —N(R$_{10}$)R$_{11}$, R$_{10}$ is C$_1$-C$_3$alkyl, and R$_{11}$ is hydrogen. In some embodiments is a compound of Formula (II), wherein R$_1$ is —N(R$_{10}$)R$_{11}$, R$_{10}$ is —CH$_3$, and R$_{11}$ is hydrogen. In some embodiments is a compound of Formula (II), wherein R$_1$ is —N(R$_{10}$)R$_{11}$, and R$_{10}$ and R$_{11}$ are each C$_1$-C$_3$alkyl. In some embodiments is a compound of Formula (II), wherein R$_1$ is —N(R$_{10}$)R$_{11}$, and R$_{10}$ and R$_{11}$ are each —CH$_3$.

In some embodiments is a compound of Formula (II), wherein R$_1$ is —N(R$_{10}$)R$_{11}$, and R$_{10}$ and R$_{11}$ together with the nitrogen atom to which they are attached, form a 4-6 membered heterocyclic ring optionally substituted by C$_1$-C$_6$alkyl or —CO$_2$H. In some embodiments is a compound of Formula (II), wherein R$_1$ is —N(R$_{10}$)R$_{11}$, and R$_{10}$ and R$_{11}$ together with the nitrogen atom to which they are attached, form a pyrrolidine ring optionally substituted by C$_1$-C$_6$alkyl or —CO$_2$H. In some embodiments is a compound of Formula (II), wherein R$_1$ is —N(R$_{10}$)R$_{11}$, and R$_{10}$ and R$_{11}$ together with the nitrogen atom to which they are attached, form an unsubstituted pyrrolidine ring. In some embodiments is a compound of Formula (II), wherein R$_1$ is —N(R$_{10}$)R$_{11}$, and R$_{10}$ and R$_{11}$ together with the nitrogen atom to which they are attached, form a pyrrolidine ring substituted by C$_1$-C$_6$alkyl. In some embodiments is a compound of Formula (II), wherein R$_1$ is —N(R$_{10}$)R$_{11}$, and R$_{10}$ and R$_{11}$ together with the nitrogen atom to which they are attached, form a pyrrolidine ring substituted by —CO$_2$H. In some embodiments is a compound of Formula (II), wherein R$_1$ is —N(R$_{10}$)R$_{11}$, and R$_{10}$ and R$_{11}$ together with the nitrogen atom to which they are attached, form a piperidine ring optionally substituted by C$_1$-C$_6$alkyl or —CO$_2$H. In some embodiments is a compound of Formula (II), wherein R$_1$ is —N(R$_{10}$)R$_{11}$, and R$_{10}$ and R$_{11}$ together with the nitrogen atom to which they are attached, form an unsubstituted piperidine ring. In some embodiments is a compound of Formula (II), wherein R$_1$ is —N(R$_{10}$)R$_{11}$, and R$_{10}$ and R$_{11}$ together with the nitrogen atom to which they are attached, form a piperidine ring substituted by C$_1$-C$_6$alkyl. In some embodiments is a compound of Formula (II), wherein R$_1$ is —N(R$_{10}$)R$_{11}$, and R$_{10}$ and R$_{11}$ together with the nitrogen atom to which they are attached, form a piperidine ring substituted by —CO$_2$H. In some embodiments is a compound of Formula (II), wherein R$_1$ is —N(R$_{10}$)R$_{11}$, and R$_{10}$ and R$_{11}$ together with the nitrogen atom to which they are attached, form a piperazine ring optionally substituted by C$_1$-C$_6$alkyl. In some embodiments is a compound of Formula (II), wherein R$_1$ is —N(R$_{10}$)R$_{11}$, and R$_{10}$ and R$_{11}$ together with the nitrogen atom to which they are attached, form an unsubstituted piperazine ring. In some embodiments is a compound of Formula (II), wherein R$_1$ is —N(R$_{10}$)R$_{11}$, and R$_{10}$ and R$_{11}$ together with the nitrogen atom to which they are attached, form a piperazine ring substituted by C$_1$-C$_6$alkyl. In some embodiments is a compound of Formula (II), wherein R$_1$ is —N(R$_{10}$)R$_{11}$, and R$_{10}$ and R$_{11}$ together with the nitrogen atom to which they are attached, form an unsubstituted morpholine ring.

In some embodiments is a compound of Formula (II), wherein R$_2$ is hydrogen. In some embodiments is a compound of Formula (II), wherein R$_2$ is halogen. In some embodiments is a compound of Formula (II), wherein R$_2$ is F. In some embodiments is a compound of Formula (II), wherein R$_2$ is Cl. In some embodiments is a compound of Formula (II), wherein R$_2$ is Br.

In some embodiments is a compound of Formula (II), wherein n is 1. In some embodiments is a compound of Formula (II), wherein n is 2.

In some embodiments is a compound of Formula (II), wherein R$_4$ and R$_5$ are each independently selected from the group consisting of hydrogen, C$_1$-C$_6$alkyl optionally substituted by one, two, or three groups independently selected from halogen, cyano, and hydroxyl, and —(C$_1$-C$_6$alkylene)-(phenyl) optionally substituted by one, two, or three groups independently selected from halogen, cyano, —CF$_3$, —OH, $C_1$-$C_6$alkyl, and $C_1$-$C_6$alkoxy. In some embodiments is a compound of Formula (II), wherein $R_4$ is hydrogen and $R_5$ is selected from the group consisting of hydrogen, $C_1$-$C_6$alkyl optionally substituted by one, two, or three groups independently selected from halogen, cyano, and hydroxyl, and —($C_1$-$C_6$alkylene)-(phenyl) optionally substituted by one, two, or three groups independently selected from halogen, cyano, —$CF_3$, —OH, $C_1$-$C_6$alkyl, and $C_1$-$C_6$alkoxy. In some embodiments is a compound of Formula (II), wherein $R_4$ is hydrogen and $R_5$ is hydrogen. In some embodiments is a compound of Formula (II), wherein $R_4$ is hydrogen and $R_5$ is $C_1$-$C_6$alkyl optionally substituted by one, two, or three groups independently selected from halogen, cyano, and hydroxyl. In some embodiments is a compound of Formula (II), wherein $R_4$ is hydrogen and $R_5$ is unsubstituted $C_1$-$C_6$alkyl. In some embodiments is a compound of Formula (II), wherein $R_4$ is hydrogen and $R_5$ is —($C_1$-$C_6$alkylene)-(phenyl) optionally substituted by one, two, or three groups independently selected from halogen, cyano, —$CF_3$, —OH, $C_1$-$C_6$alkyl, and $C_1$-$C_6$alkoxy. In some embodiments is a compound of Formula (II), wherein $R_4$ is hydrogen and $R_5$ is unsubstituted —($C_1$-$C_6$alkylene)-(phenyl). In some embodiments is a compound of Formula (II), wherein $R_4$ is hydrogen and $R_5$ is unsubstituted —($CH_2$)-(phenyl). In some embodiments is a compound of Formula (II), wherein $R_4$ is hydrogen and $R_5$ is —($C_1$-$C_6$alkylene)-(phenyl) substituted by one, two, or three groups independently selected from halogen, cyano, —$CF_3$, —OH, $C_1$-$C_6$alkyl, and $C_1$-$C_6$alkoxy. In some embodiments is a compound of Formula (II), wherein $R_4$ is hydrogen and $R_5$ is —($C_1$-$C_6$alkylene)-(phenyl) substituted by one halogen. In some embodiments is a compound of Formula (II), wherein $R_4$ is hydrogen and $R_5$ is —($C_1$-$C_6$alkylene)-(phenyl) substituted by one —$CF_3$. In some embodiments is a compound of Formula (II), wherein $R_4$ is hydrogen and $R_5$ is —($C_1$-$C_6$alkylene)-(phenyl) substituted by one $C_1$-$C_6$alkyl. In some embodiments is a compound of Formula (II), wherein $R_4$ is hydrogen and $R_5$ is —($C_1$-$C_6$alkylene)-(phenyl) substituted by one $C_1$-$C_6$alkoxy.

In some embodiments is a compound of Formula (II), wherein $R_3$ is hydrogen or $C_1$-$C_3$alkyl. In some embodiments is a compound of Formula (II), wherein $R_3$ is hydrogen. In some embodiments is a compound of Formula (II), wherein $R_3$ is $C_1$-$C_3$alkyl. In some embodiments is a compound of Formula (II), wherein $R_3$ is $CH_3$.

In another embodiment is a compound of Formula (IIa), or a pharmaceutically acceptable salt or solvate thereof:

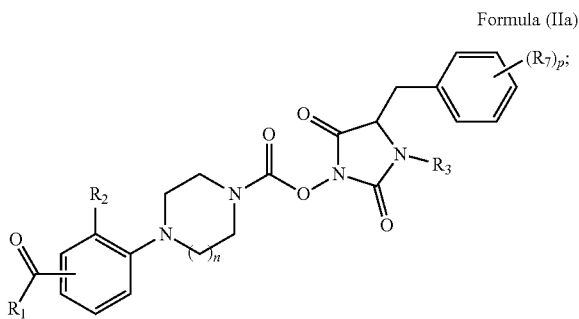

Formula (IIa)

wherein:
$R_1$ is selected from the group consisting of —N($R_{10}$)$R_{11}$, —OH, $C_1$-$C_6$alkyl, and $C_1$-$C_6$alkoxy;
$R_2$ is hydrogen or halogen;

$R_3$ is hydrogen or $C_1$-$C_3$alkyl;
each $R_7$ is independently selected from the group consisting of halogen, cyano, —$CF_3$, —OH, $C_1$-$C_6$alkyl, and $C_1$-$C_6$alkoxy;
$R_{10}$ and $R_{11}$ are each independently selected from the group consisting of hydrogen, and $C_1$-$C_3$alkyl; or $R_{10}$ and $R_{11}$ together with the nitrogen atom to which they are attached, form a 4-6 membered heterocyclic ring optionally substituted by $C_1$-$C_6$alkyl or —$CO_2H$;
n is 1; and
p is 0, 1, 2, or 3.

In some embodiments is a compound of Formula (IIa), wherein $R_1$ is —N($R_{10}$)$R_{11}$. In some embodiments is a compound of Formula (IIa), wherein $R_1$ is —N($R_{10}$)$R_{11}$, and $R_{10}$ and $R_{11}$ are each independently selected from the group consisting of hydrogen and $C_1$-$C_3$alkyl. In some embodiments is a compound of Formula (IIa), wherein $R_1$ is —N($R_{10}$)$R_{11}$, and $R_{10}$ and $R_{11}$ are each hydrogen. In some embodiments is a compound of Formula (IIa), wherein $R_1$ is —N($R_{10}$)$R_{11}$, $R_{10}$ is $C_1$-$C_3$alkyl, and $R_{11}$ is hydrogen. In some embodiments is a compound of Formula (IIa), wherein $R_1$ is —N($R_{10}$)$R_{11}$, $R_{10}$ is —$CH_3$, and $R_{11}$ is hydrogen. In some embodiments is a compound of Formula (IIa), wherein $R_1$ is —N($R_{10}$)$R_{11}$, and $R_{10}$ and $R_{11}$ are each $C_1$-$C_3$alkyl. In some embodiments is a compound of Formula (IIa), wherein $R_1$ is —N($R_{10}$)$R_{11}$, and $R_{10}$ and $R_{11}$ are each —$CH_3$.

In some embodiments is a compound of Formula (IIa), wherein $R_1$ is —N($R_{10}$)$R_{11}$, and $R_{10}$ and $R_{11}$ together with the nitrogen atom to which they are attached, form a 4-6 membered heterocyclic ring optionally substituted by $C_1$-$C_6$alkyl or —$CO_2H$. In some embodiments is a compound of Formula (IIa), wherein $R_1$ is —N($R_{10}$)$R_{11}$, and $R_{10}$ and $R_{11}$ together with the nitrogen atom to which they are attached, form a pyrrolidine ring optionally substituted by $C_1$-$C_6$alkyl or —$CO_2H$. In some embodiments is a compound of Formula (IIa), wherein $R_1$ is —N($R_{10}$)$R_{11}$, and $R_{10}$ and $R_{11}$ together with the nitrogen atom to which they are attached, form an unsubstituted pyrrolidine ring. In some embodiments is a compound of Formula (IIa), wherein $R_1$ is —N($R_{10}$)$R_{11}$, and $R_{10}$ and $R_{11}$ together with the nitrogen atom to which they are attached, form a pyrrolidine ring substituted by $C_1$-$C_6$alkyl. In some embodiments is a compound of Formula (IIa), wherein $R_1$ is —N($R_{10}$)$R_{11}$, and $R_{10}$ and $R_{11}$ together with the nitrogen atom to which they are attached, form a pyrrolidine ring substituted by —$CO_2H$. In some embodiments is a compound of Formula (IIa), wherein $R_1$ is —N($R_{10}$)$R_{11}$, and $R_{10}$ and $R_{11}$ together with the nitrogen atom to which they are attached, form a piperidine ring optionally substituted by $C_1$-$C_6$alkyl or —$CO_2H$. In some embodiments is a compound of Formula (IIa), wherein $R_1$ is —N($R_{10}$)$R_{11}$, and $R_{10}$ and $R_{11}$ together with the nitrogen atom to which they are attached, form an unsubstituted piperidine ring. In some embodiments is a compound of Formula (IIa), wherein $R_1$ is —N($R_{10}$)$R_{11}$, and $R_{10}$ and $R_{11}$ together with the nitrogen atom to which they are attached, form a piperidine ring substituted by $C_1$-$C_6$alkyl. In some embodiments is a compound of Formula (IIa), wherein $R_1$ is —N($R_{10}$)$R_{11}$, and $R_{10}$ and $R_{11}$ together with the nitrogen atom to which they are attached, form a piperidine ring substituted by —$CO_2H$. In some embodiments is a compound of Formula (IIa), wherein $R_1$ is —N($R_{10}$)$R_{11}$, and $R_{10}$ and $R_{11}$ together with the nitrogen atom to which they are attached, form a piperazine ring optionally substituted by $C_1$-$C_6$alkyl. In some embodiments is a compound of Formula (IIa), wherein $R_1$ is —N($R_{10}$)$R_{11}$, and $R_{10}$ and $R_{11}$ together with the nitrogen atom to which they are attached, form an unsubstituted piperazine ring. In some embodiments is a compound of Formula (IIa), wherein $R_1$ is —$N(R_{10})R_{11}$, and $R_{10}$ and $R_{11}$ together with the nitrogen atom to which they are attached, form a piperazine ring substituted by $C_1$-$C_6$alkyl. In some embodiments is a compound of Formula (IIa), wherein $R_1$ is —$N(R_{10})R_{11}$, and $R_{10}$ and $R_{11}$ together with the nitrogen atom to which they are attached, form an unsubstituted morpholine ring.

In some embodiments is a compound of Formula (IIa), wherein $R_2$ is hydrogen. In some embodiments is a compound of Formula (IIa), wherein $R_2$ is halogen. In some embodiments is a compound of Formula (IIa), wherein $R_2$ is F. In some embodiments is a compound of Formula (IIa), wherein $R_2$ is Cl. In some embodiments is a compound of Formula (IIa), wherein $R_2$ is Br.

In some embodiments is a compound of Formula (IIa), wherein p is 0. In some embodiments is a compound of Formula (IIa), wherein p is 1. In some embodiments is a compound of Formula (IIa), wherein p is 1 and $R_7$ is selected from the group consisting of halogen, cyano, —$CF_3$, —OH, $C_1$-$C_6$alkyl, and $C_1$-$C_6$alkoxy. In some embodiments is a compound of Formula (IIa), wherein p is 1 and $R_7$ is halogen. In some embodiments is a compound of Formula (IIa), wherein p is 1 and $R_7$ is —$CF_3$. In some embodiments is a compound of Formula (IIa), wherein p is 1 and $R_7$ is $C_1$-$C_6$alkyl. In some embodiments is a compound of Formula (IIa), wherein p is 1 and $R_7$ is $C_1$-$C_6$alkoxy. In some embodiments is a compound of Formula (IIa), wherein p is 2. In some embodiments is a compound of Formula (IIa), wherein p is 2 and each $R_7$ is independently selected from the group consisting of halogen, cyano, —$CF_3$, —OH, $C_1$-$C_6$alkyl, and $C_1$-$C_6$alkoxy.

In some embodiments is a compound of Formula (IIa), wherein $R_3$ is hydrogen or $C_1$-$C_3$alkyl. In some embodiments is a compound of Formula (IIa), wherein $R_3$ is hydrogen. In some embodiments is a compound of Formula (IIa), wherein $R_3$ is $C_1$-$C_3$alkyl. In some embodiments is a compound of Formula (IIa), wherein $R_3$ is $CH_3$.

In another embodiment is a compound of Formula (IIb), or a pharmaceutically acceptable salt or solvate thereof:

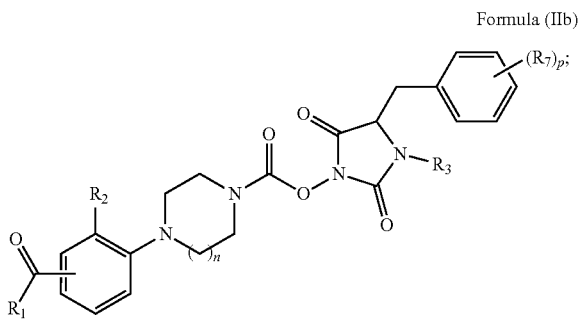

Formula (IIb)

wherein:
$R_1$ is selected from the group consisting of —$N(R_{10})R_{11}$, —OH, $C_1$-$C_6$alkyl, and $C_1$-$C_6$alkoxy;
$R_2$ is hydrogen or halogen;
$R_3$ is hydrogen or $C_1$-$C_3$alkyl;
each $R_7$ is independently selected from the group consisting of halogen, cyano, —$CF_3$, —OH, $C_1$-$C_6$alkyl, and $C_1$-$C_6$alkoxy;
$R_{10}$ and $R_{11}$ are each independently selected from the group consisting of hydrogen, and $C_1$-$C_3$alkyl; or $R_{10}$ and $R_{11}$ together with the nitrogen atom to which they are attached, form a 4-6 membered heterocyclic ring optionally substituted by $C_1$-$C_6$alkyl or —$CO_2H$;
n is 2; and
p is 0, 1, 2, or 3.

In some embodiments is a compound of Formula (IIb), wherein $R_1$ is —$N(R_{10})R_{11}$. In some embodiments is a compound of Formula (IIb), wherein $R_1$ is —$N(R_{10})R_{11}$, and $R_{10}$ and $R_{11}$ are each independently selected from the group consisting of hydrogen and $C_1$-$C_3$alkyl. In some embodiments is a compound of Formula (IIb), wherein $R_1$ is —$N(R_{10})R_{11}$, and $R_{10}$ and $R_{11}$ are each hydrogen. In some embodiments is a compound of Formula (IIb), wherein $R_1$ is —$N(R_{10})R_{11}$, $R_{10}$ is $C_1$-$C_3$alkyl, and $R_{11}$ is hydrogen. In some embodiments is a compound of Formula (IIb), wherein $R_1$ is —$N(R_{10})R_{11}$, $R_{10}$ is —$CH_3$, and $R_{11}$ is hydrogen. In some embodiments is a compound of Formula (IIb), wherein $R_1$ is —$N(R_{10})R_{11}$, and $R_{10}$ and $R_{11}$ are each $C_1$-$C_3$alkyl. In some embodiments is a compound of Formula (IIb), wherein $R_1$ is —$N(R_{10})R_{11}$, and $R_{10}$ and $R_{11}$ are each —$CH_3$.

In some embodiments is a compound of Formula (IIb), wherein $R_1$ is —$N(R_{10})R_{11}$, and $R_{10}$ and $R_{11}$ together with the nitrogen atom to which they are attached, form a 4-6 membered heterocyclic ring optionally substituted by $C_1$-$C_6$alkyl or —$CO_2H$. In some embodiments is a compound of Formula (IIb), wherein $R_1$ is —$N(R_{10})R_{11}$, and $R_{10}$ and $R_{11}$ together with the nitrogen atom to which they are attached, form a pyrrolidine ring optionally substituted by $C_1$-$C_6$alkyl or —$CO_2H$. In some embodiments is a compound of Formula (IIb), wherein $R_1$ is —$N(R_{10})R_{11}$, and $R_{10}$ and $R_{11}$ together with the nitrogen atom to which they are attached, form an unsubstituted pyrrolidine ring. In some embodiments is a compound of Formula (IIb), wherein $R_1$ is —$N(R_{10})R_{11}$, and $R_{10}$ and $R_{11}$ together with the nitrogen atom to which they are attached, form a pyrrolidine ring substituted by $C_1$-$C_6$alkyl. In some embodiments is a compound of Formula (IIb), wherein $R_1$ is —$N(R_{10})R_{11}$, and $R_{10}$ and $R_{11}$ together with the nitrogen atom to which they are attached, form a pyrrolidine ring substituted by —$CO_2H$. In some embodiments is a compound of Formula (IIb), wherein $R_1$ is —$N(R_{10})R_{11}$, and $R_{10}$ and $R_{11}$ together with the nitrogen atom to which they are attached, form a piperidine ring optionally substituted by $C_1$-$C_6$alkyl or —$CO_2H$. In some embodiments is a compound of Formula (IIb), wherein $R_1$ is —$N(R_{10})R_{11}$, and $R_{10}$ and $R_{11}$ together with the nitrogen atom to which they are attached, form an unsubstituted piperidine ring. In some embodiments is a compound of Formula (IIb), wherein $R_1$ is —$N(R_{10})R_{11}$, and $R_{10}$ and $R_{11}$ together with the nitrogen atom to which they are attached, form a piperidine ring substituted by $C_1$-$C_6$alkyl. In some embodiments is a compound of Formula (IIb), wherein $R_1$ is —$N(R_{10})R_{11}$, and $R_{10}$ and $R_{11}$ together with the nitrogen atom to which they are attached, form a piperidine ring substituted by —$CO_2H$. In some embodiments is a compound of Formula (IIb), wherein $R_1$ is —$N(R_{10})R_{11}$, and $R_{10}$ and $R_{11}$ together with the nitrogen atom to which they are attached, form a piperazine ring optionally substituted by $C_1$-$C_6$alkyl. In some embodiments is a compound of Formula (IIb), wherein $R_1$ is —$N(R_{10})R_{11}$, and $R_{10}$ and $R_{11}$ together with the nitrogen atom to which they are attached, form an unsubstituted piperazine ring. In some embodiments is a compound of Formula (IIb), wherein $R_1$ is —$N(R_{10})R_{11}$, and $R_{10}$ and $R_{11}$ together with the nitrogen atom to which they are attached, form a piperazine ring substituted by $C_1$-$C_6$alkyl. In some embodiments is a compound of Formula (IIb), wherein $R_1$ is —$N(R_{10})R_{11}$, and $R_{10}$ and $R_{11}$ together with the nitrogen atom to which they are attached, form an unsubstituted morpholine ring.

In some embodiments is a compound of Formula (IIb), wherein $R_2$ is hydrogen. In some embodiments is a compound of Formula (IIb), wherein $R_2$ is halogen. In some embodiments is a compound of Formula (IIb), wherein $R_2$ is F. In some embodiments is a compound of Formula (IIb), wherein $R_2$ is Cl. In some embodiments is a compound of Formula (IIb), wherein $R_2$ is Br.

In some embodiments is a compound of Formula (IIb), wherein p is 0. In some embodiments is a compound of Formula (IIb), wherein p is 1. In some embodiments is a compound of Formula (IIb), wherein p is 1 and $R_7$ is selected from the group consisting of halogen, cyano, —$CF_3$, —OH, $C_1$-$C_6$alkyl, and $C_1$-$C_6$alkoxy. In some embodiments is a compound of Formula (IIb), wherein p is 1 and $R_7$ is halogen. In some embodiments is a compound of Formula (IIb), wherein p is 1 and $R_7$ is —$CF_3$. In some embodiments is a compound of Formula (IIb), wherein p is 1 and $R_7$ is $C_1$-$C_6$alkyl. In some embodiments is a compound of Formula (IIb), wherein p is 1 and $R_7$ is $C_1$-$C_6$alkoxy. In some embodiments is a compound of Formula (IIb), wherein p is 2. In some embodiments is a compound of Formula (IIb), wherein p is 2 and each $R_7$ is independently selected from the group consisting of halogen, cyano, —$CF_3$, —OH, $C_1$-$C_6$alkyl, and $C_1$-$C_6$alkoxy.

In some embodiments is a compound of Formula (IIb), wherein $R_3$ is hydrogen or $C_1$-$C_3$alkyl. In some embodiments is a compound of Formula (IIb), wherein $R_3$ is hydrogen. In some embodiments is a compound of Formula (IIb), wherein $R_3$ is $C_1$-$C_3$alkyl. In some embodiments is a compound of Formula (IIb), wherein $R_3$ is $CH_3$.

In another embodiment is a compound of Formula (IIc), or a pharmaceutically acceptable salt or solvate thereof:

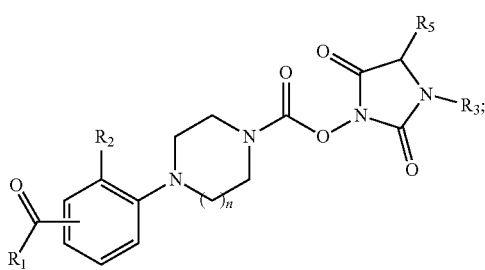

Formula (IIc)

wherein:
$R_1$ is selected from the group consisting of —N($R_{10}$)$R_{11}$, —OH, $C_1$-$C_6$alkyl, and $C_1$-$C_6$alkoxy;
$R_2$ is hydrogen or halogen;
$R_3$ is hydrogen or $C_1$-$C_3$alkyl;
$R_5$ is $C_1$-$C_6$alkyl optionally substituted by one, two, or three groups independently selected from halogen, cyano, and hydroxyl;
$R_{10}$ and $R_{11}$ are each independently selected from the group consisting of hydrogen, and $C_1$-$C_3$alkyl; or $R_{10}$ and $R_{11}$ together with the nitrogen atom to which they are attached, form a 4-6 membered heterocyclic ring optionally substituted by $C_1$-$C_6$alkyl or —$CO_2$H; and
n is 1.

In some embodiments is a compound of Formula (IIc), wherein $R_1$ is —N($R_{10}$)$R_{11}$. In some embodiments is a compound of Formula (IIc), wherein $R_1$ is —N($R_{10}$)$R_{11}$, and $R_{10}$ and $R_{11}$ are each independently selected from the group consisting of hydrogen and $C_1$-$C_3$alkyl. In some embodiments is a compound of Formula (IIc), wherein $R_1$ is —N($R_{10}$)$R_{11}$, and $R_{10}$ and $R_{11}$ are each hydrogen. In some embodiments is a compound of Formula (IIc), wherein $R_1$ is —N($R_{10}$)$R_{11}$, $R_{10}$ is $C_1$-$C_3$alkyl, and $R_{11}$ is hydrogen. In some embodiments is a compound of Formula (IIc), wherein $R_1$ is —N($R_{10}$)$R_{11}$, $R_{10}$ is —$CH_3$, and $R_{11}$ is hydrogen. In some embodiments is a compound of Formula (IIc), wherein $R_1$ is —N($R_{10}$)$R_{11}$, and $R_{10}$ and $R_{11}$ are each $C_1$-$C_3$alkyl. In some embodiments is a compound of Formula (IIc), wherein $R_1$ is —N($R_{10}$)$R_{11}$, and $R_{10}$ and $R_{11}$ are each —$CH_3$.

In some embodiments is a compound of Formula (IIc), wherein $R_1$ is —N($R_{10}$)$R_{11}$, and $R_{10}$ and $R_{11}$ together with the nitrogen atom to which they are attached, form a 4-6 membered heterocyclic ring optionally substituted by $C_1$-$C_6$alkyl or —$CO_2$H. In some embodiments is a compound of Formula (IIc), wherein $R_1$ is —N($R_{10}$)$R_{11}$, and $R_{10}$ and $R_{11}$ together with the nitrogen atom to which they are attached, form a pyrrolidine ring optionally substituted by $C_1$-$C_6$alkyl or —$CO_2$H. In some embodiments is a compound of Formula (IIc), wherein $R_1$ is —N($R_{10}$)$R_{11}$, and $R_{10}$ and $R_{11}$ together with the nitrogen atom to which they are attached, form an unsubstituted pyrrolidine ring. In some embodiments is a compound of Formula (IIc), wherein $R_1$ is —N($R_{10}$)$R_{11}$, and $R_{10}$ and $R_{11}$ together with the nitrogen atom to which they are attached, form a pyrrolidine ring substituted by $C_1$-$C_6$alkyl. In some embodiments is a compound of Formula (IIc), wherein $R_1$ is —N($R_{10}$)$R_{11}$, and $R_{10}$ and $R_{11}$ together with the nitrogen atom to which they are attached, form a pyrrolidine ring substituted by —$CO_2$H. In some embodiments is a compound of Formula (IIc), wherein $R_1$ is —N($R_{10}$)$R_{11}$, and $R_{10}$ and $R_{11}$ together with the nitrogen atom to which they are attached, form a piperidine ring optionally substituted by $C_1$-$C_6$alkyl or —$CO_2$H. In some embodiments is a compound of Formula (IIc), wherein $R_1$ is —N($R_{10}$)$R_{11}$, and $R_{10}$ and $R_{11}$ together with the nitrogen atom to which they are attached, form an unsubstituted piperidine ring. In some embodiments is a compound of Formula (IIc), wherein $R_1$ is —N($R_{10}$)$R_{11}$, and $R_{10}$ and $R_{11}$ together with the nitrogen atom to which they are attached, form a piperidine ring substituted by $C_1$-$C_6$alkyl. In some embodiments is a compound of Formula (IIc), wherein $R_1$ is —N($R_{10}$)$R_{11}$, and $R_{10}$ and $R_{11}$ together with the nitrogen atom to which they are attached, form a piperidine ring substituted by —$CO_2$H. In some embodiments is a compound of Formula (IIc), wherein $R_1$ is —N($R_{10}$)$R_{11}$, and $R_{10}$ and $R_{11}$ together with the nitrogen atom to which they are attached, form a piperazine ring optionally substituted by $C_1$-$C_6$alkyl. In some embodiments is a compound of Formula (IIc), wherein $R_1$ is —N($R_{10}$)$R_{11}$, and $R_{10}$ and $R_{11}$ together with the nitrogen atom to which they are attached, form an unsubstituted piperazine ring. In some embodiments is a compound of Formula (IIc), wherein $R_1$ is —N($R_{10}$)$R_{11}$, and $R_{10}$ and $R_{11}$ together with the nitrogen atom to which they are attached, form a piperazine ring substituted by $C_1$-$C_6$alkyl. In some embodiments is a compound of Formula (IIc), wherein $R_1$ is —N($R_{10}$)$R_{11}$, and $R_{10}$ and $R_{11}$ together with the nitrogen atom to which they are attached, form an unsubstituted morpholine ring.

In some embodiments is a compound of Formula (IIc), wherein $R_2$ is hydrogen. In some embodiments is a compound of Formula (IIc), wherein $R_2$ is halogen. In some embodiments is a compound of Formula (IIc), wherein $R_2$ is F. In some embodiments is a compound of Formula (IIc), wherein $R_2$ is Cl. In some embodiments is a compound of Formula (IIc), wherein $R_2$ is Br.

In some embodiments is a compound of Formula (IIc), wherein $R_5$ is $C_1$-$C_6$alkyl optionally substituted by one, two, or three groups independently selected from halogen, cyano, and hydroxyl. In some embodiments is a compound of Formula (IIc), wherein $R_5$ is unsubstituted $C_1$-$C_6$alkyl. In some embodiments is a compound of Formula (IIc), wherein $R_5$ is —$CH_3$. In some embodiments is a compound of Formula (IIc), wherein $R_5$ is —$CH_2CH_3$. In some embodiments is a compound of Formula (IIc), wherein $R_5$ is —$CH(CH_3)_2$. In some embodiments is a compound of Formula (IIc), wherein $R_5$ is —$CH_2CH(CH_3)_2$.

In some embodiments is a compound of Formula (IIc), wherein $R_3$ is hydrogen or $C_1$-$C_3$alkyl. In some embodiments is a compound of Formula (IIc), wherein $R_3$ is hydrogen. In some embodiments is a compound of Formula (IIc), wherein $R_3$ is $C_1$-$C_3$alkyl. In some embodiments is a compound of Formula (IIc), wherein $R_3$ is —$CH_3$.

In another embodiment is a compound of Formula (IId), or a pharmaceutically acceptable salt or solvate thereof:

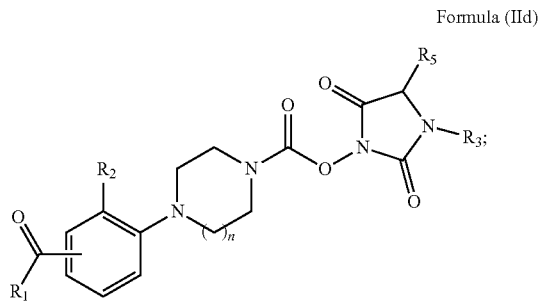

Formula (IId)

wherein:
$R_1$ is selected from the group consisting of —$N(R_{10})R_{11}$, —OH, $C_1$-$C_6$alkyl, and $C_1$-$C_6$alkoxy;
$R_2$ is hydrogen or halogen;
$R_3$ is hydrogen or $C_1$-$C_3$alkyl;
$R_5$ is $C_1$-$C_6$alkyl optionally substituted by one, two, or three groups independently selected from halogen, cyano, and hydroxyl;
$R_{10}$ and $R_{11}$ are each independently selected from the group consisting of hydrogen, and $C_1$-$C_3$alkyl; or $R_{10}$ and $R_{11}$ together with the nitrogen atom to which they are attached, form a 4-6 membered heterocyclic ring optionally substituted by $C_1$-$C_6$alkyl or —$CO_2H$; and
n is 2.

In some embodiments is a compound of Formula (IId), wherein $R_1$ is —$N(R_{10})R_{11}$. In some embodiments is a compound of Formula (IId), wherein $R_1$ is —$N(R_{10})R_{11}$, and $R_{10}$ and $R_{11}$ are each independently selected from the group consisting of hydrogen and $C_1$-$C_3$alkyl. In some embodiments is a compound of Formula (IId), wherein $R_1$ is —$N(R_{10})R_{11}$, and $R_{10}$ and $R_{11}$ are each hydrogen. In some embodiments is a compound of Formula (IId), wherein $R_1$ is —$N(R_{10})R_{11}$, $R_{10}$ is $C_1$-$C_3$alkyl, and $R_{11}$ is hydrogen. In some embodiments is a compound of Formula (IId), wherein $R_1$ is —$N(R_{10})R_{11}$, $R_{10}$ is —$CH_3$, and $R_{11}$ is hydrogen. In some embodiments is a compound of Formula (IId), wherein $R_1$ is —$N(R_{10})R_{11}$, and $R_{10}$ and $R_{11}$ are each $C_1$-$C_3$alkyl. In some embodiments is a compound of Formula (IId), wherein $R_1$ is —$N(R_{10})R_{11}$, and $R_{10}$ and $R_{11}$ are each —$CH_3$.

In some embodiments is a compound of Formula (IId), wherein $R_1$ is —$N(R_{10})R_{11}$, and $R_{10}$ and $R_{11}$ together with the nitrogen atom to which they are attached, form a 4-6 membered heterocyclic ring optionally substituted by $C_1$-$C_6$alkyl or —$CO_2H$. In some embodiments is a compound of Formula (IId), wherein $R_1$ is —$N(R_{10})R_{11}$, and $R_{10}$ and $R_{11}$ together with the nitrogen atom to which they are attached, form a pyrrolidine ring optionally substituted by $C_1$-$C_6$alkyl or —$CO_2H$. In some embodiments is a compound of Formula (IId), wherein $R_1$ is —$N(R_{10})R_{11}$, and $R_{10}$ and $R_{11}$ together with the nitrogen atom to which they are attached, form an unsubstituted pyrrolidine ring. In some embodiments is a compound of Formula (IId), wherein $R_1$ is —$N(R_{10})R_{11}$, and $R_{10}$ and $R_{11}$ together with the nitrogen atom to which they are attached, form a pyrrolidine ring substituted by $C_1$-$C_6$alkyl. In some embodiments is a compound of Formula (IId), wherein $R_1$ is —$N(R_{10})R_{11}$, and $R_{10}$ and $R_{11}$ together with the nitrogen atom to which they are attached, form a pyrrolidine ring substituted by —$CO_2H$. In some embodiments is a compound of Formula (IId), wherein $R_1$ is —$N(R_{10})R_{11}$, and $R_{10}$ and $R_{11}$ together with the nitrogen atom to which they are attached, form a piperidine ring optionally substituted by $C_1$-$C_6$alkyl or —$CO_2H$. In some embodiments is a compound of Formula (IId), wherein $R_1$ is —$N(R_{10})R_{11}$, and $R_{10}$ and $R_{11}$ together with the nitrogen atom to which they are attached, form an unsubstituted piperidine ring. In some embodiments is a compound of Formula (IId), wherein $R_1$ is —$N(R_{10})R_{11}$, and $R_{10}$ and $R_{11}$ together with the nitrogen atom to which they are attached, form a piperidine ring substituted by $C_1$-$C_6$alkyl. In some embodiments is a compound of Formula (IId), wherein $R_1$ is —$N(R_{10})R_{11}$, and $R_{10}$ and $R_{11}$ together with the nitrogen atom to which they are attached, form a piperidine ring substituted by —$CO_2H$. In some embodiments is a compound of Formula (IId), wherein $R_1$ is —$N(R_{10})R_{11}$, and $R_{10}$ and $R_{11}$ together with the nitrogen atom to which they are attached, form a piperazine ring optionally substituted by $C_1$-$C_6$alkyl. In some embodiments is a compound of Formula (IId), wherein $R_1$ is —$N(R_{10})R_{11}$, and $R_{10}$ and $R_{11}$ together with the nitrogen atom to which they are attached, form an unsubstituted piperazine ring. In some embodiments is a compound of Formula (IId), wherein $R_1$ is —$N(R_{10})R_{11}$, and $R_{10}$ and $R_{11}$ together with the nitrogen atom to which they are attached, form a piperazine ring substituted by $C_1$-$C_6$alkyl. In some embodiments is a compound of Formula (IId), wherein $R_1$ is —$N(R_{10})R_{11}$, and $R_{10}$ and $R_{11}$ together with the nitrogen atom to which they are attached, form an unsubstituted morpholine ring.

In some embodiments is a compound of Formula (IId), wherein $R_2$ is hydrogen. In some embodiments is a compound of Formula (IId), wherein $R_2$ is halogen. In some embodiments is a compound of Formula (IId), wherein $R_2$ is F. In some embodiments is a compound of Formula (IId), wherein $R_2$ is Cl. In some embodiments is a compound of Formula (IId), wherein $R_2$ is Br.

In some embodiments is a compound of Formula (IId), wherein $R_5$ is $C_1$-$C_6$alkyl optionally substituted by one, two, or three groups independently selected from halogen, cyano, and hydroxyl. In some embodiments is a compound of Formula (IId), wherein $R_5$ is unsubstituted $C_1$-$C_6$alkyl. In some embodiments is a compound of Formula (IId), wherein $R_5$ is —$CH_3$. In some embodiments is a compound of Formula (IId), wherein $R_5$ is —$CH_2CH_3$. In some embodiments is a compound of Formula (IId), wherein $R_5$ is —$CH(CH_3)_2$. In some embodiments is a compound of Formula (IId), wherein $R_5$ is —$CH_2CH(CH_3)_2$.

In some embodiments is a compound of Formula (IId), wherein $R_3$ is hydrogen or $C_1$-$C_3$alkyl. In some embodiments is a compound of Formula (IId), wherein $R_3$ is hydrogen. In some embodiments is a compound of Formula (IId), wherein $R_3$ is $C_1$-$C_3$alkyl. In some embodiments is a compound of Formula (IId), wherein $R_3$ is —$CH_3$.

Further embodiments provided herein include combinations of one or more of the particular embodiments set forth above.

In some embodiments, the compound disclosed herein has the structure provided in Table 1.

TABLE 1

| Chemical Synthesis Example | Structure | Name |
|---|---|---|
| 1 | 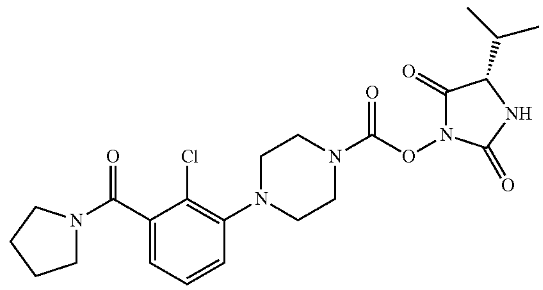 [SMILES: CC(C)[C@@H]1NC(=O)N(OC(=O)N2CCN(c3cccc(C(=O)N4CCCC4)c3Cl)CC2)C1=O] | (S)-4-isopropyl-2,5-dioxoimidazolidin-1-yl 4-(2-chloro-3-(pyrrolidine-1-carbonyl)phenyl)piperazine-1-carboxylate |
| 2 | 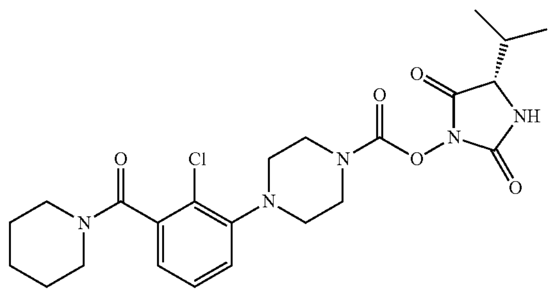 [SMILES: CC(C)[C@@H]1NC(=O)N(OC(=O)N2CCN(c3cccc(C(=O)N4CCCCC4)c3Cl)CC2)C1=O] | (S)-4-isopropyl-2,5-dioxoimidazolidin-1-yl 4-(2-chloro-3-(piperidine-1-carbonyl)phenyl)piperazine-1-carboxylate |
| 3 | 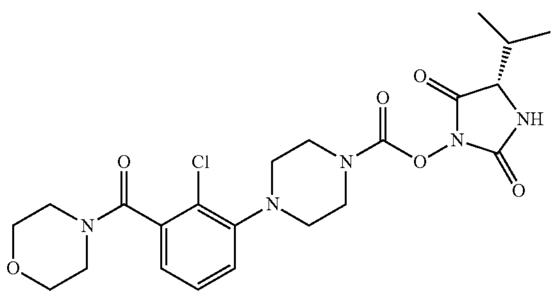 [SMILES: CC(C)[C@@H]1NC(=O)N(OC(=O)N2CCN(c3cccc(C(=O)N4CCOCC4)c3Cl)CC2)C1=O] | (S)-4-isopropyl-2,5-dioxoimidazolidin-1-yl 4-(2-chloro-3-(morpholine-4-carbonyl)phenyl)piperazine-1-carboxylate |
| 4 | 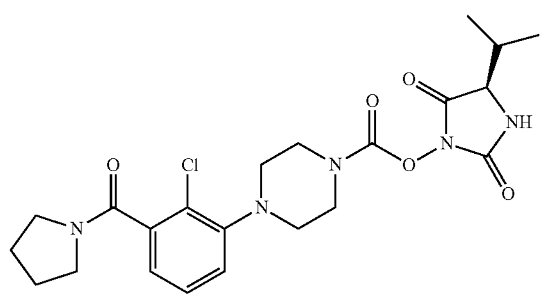 [SMILES: CC(C)[C@H]1NC(=O)N(OC(=O)N2CCN(c3cccc(C(=O)N4CCCC4)c3Cl)CC2)C1=O] | (R)-4-isopropyl-2,5-dioxoimidazolidin-1-yl 4-(2-chloro-3-(pyrrolidine-1-carbonyl)phenyl)piperazine-1-carboxylate |
| 5 | 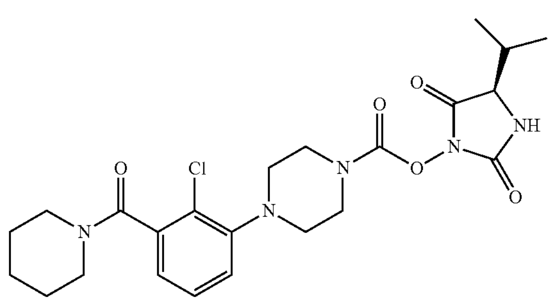 [SMILES: CC(C)[C@H]1NC(=O)N(OC(=O)N2CCN(c3cccc(C(=O)N4CCCCC4)c3Cl)CC2)C1=O] | (R)-4-isopropyl-2,5-dioxoimidazolidin-1-yl 4-(2-chloro-3-(piperidine-1-carbonyl)phenyl)piperazine-1-carboxylate |

TABLE 1-continued

| Chemical Synthesis Example | Structure | Name |
|---|---|---|
| 6 | 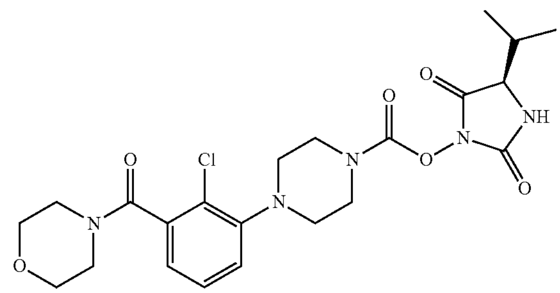 [SMILES: CC(C)[C@H]1NC(=O)N(OC(=O)N2CCN(c3cccc(C(=O)N4CCOCC4)c3Cl)CC2)C1=O] | (R)-4-isopropyl-2,5-dioxoimidazolidin-1-yl 4-(2-chloro-3-(morpholine-4-carbonyl)phenyl)piperazine-1-carboxylate |
| 7 | 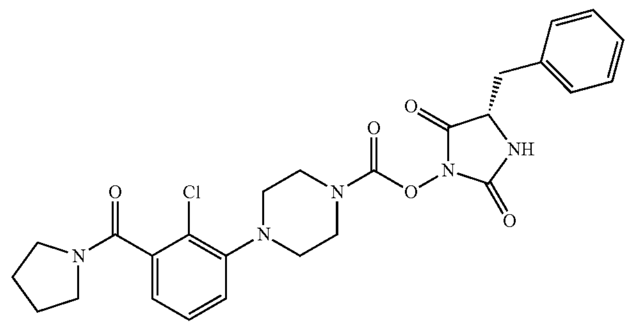 [SMILES: O=C(ON1C(=O)N[C@@H](Cc2ccccc2)C1=O)N1CCN(c2cccc(C(=O)N3CCCC3)c2Cl)CC1] | (S)-4-benzyl-2,5-dioxoimidazolidin-1-yl 4-(2-chloro-3-(pyrrolidine-1-carbonyl)phenyl)piperazine-1-carboxylate |
| 8 | 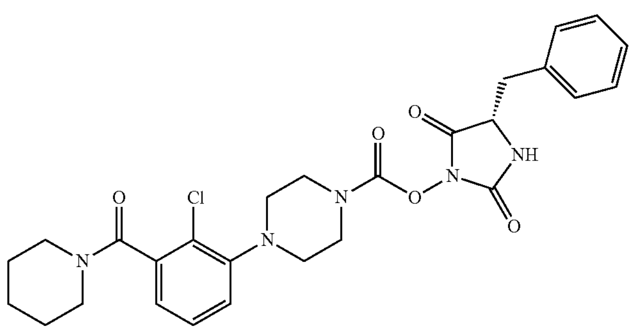 [SMILES: O=C(ON1C(=O)N[C@@H](Cc2ccccc2)C1=O)N1CCN(c2cccc(C(=O)N3CCCCC3)c2Cl)CC1] | (S)-4-benzyl-2,5-dioxoimidazolidin-1-yl 4-(2-chloro-3-(piperidine-1-carbonyl)phenyl)piperazine-1-carboxylate |
| 9 | 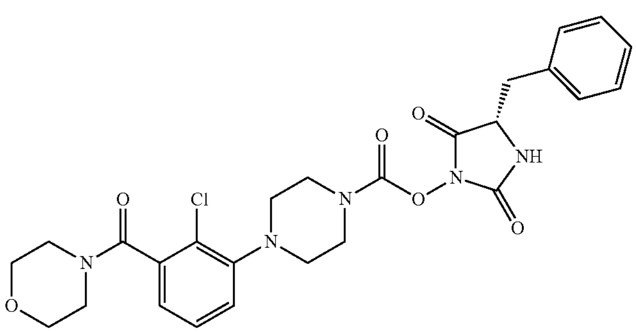 [SMILES: O=C(ON1C(=O)N[C@@H](Cc2ccccc2)C1=O)N1CCN(c2cccc(C(=O)N3CCOCC3)c2Cl)CC1] | (S)-4-benzyl-2,5-dioxoimidazolidin-1-yl 4-(2-chloro-3-(morpholine-4-carbonyl)phenyl)piperazine-1-carboxylate |

TABLE 1-continued

| Chemical Synthesis Example | Structure | Name |
|---|---|---|
| 10 | 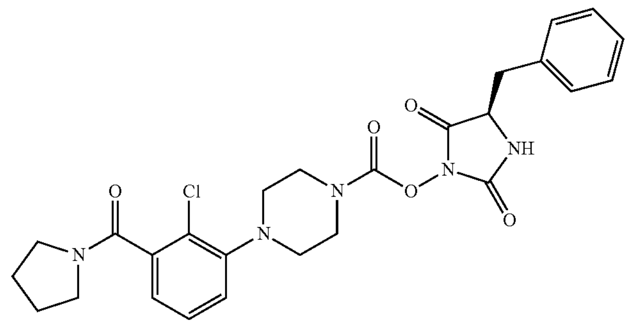 [SMILES: O=C(ON1C(=O)N[C@H](Cc2ccccc2)C1=O)N1CCN(c2cccc(C(=O)N3CCCC3)c2Cl)CC1] | (R)-4-benzyl-2,5-dioxoimidazolidin-1-yl 4-(2-chloro-3-(pyrrolidine-1-carbonyl)phenyl)piperazine-1-carboxylate |
| 11 | 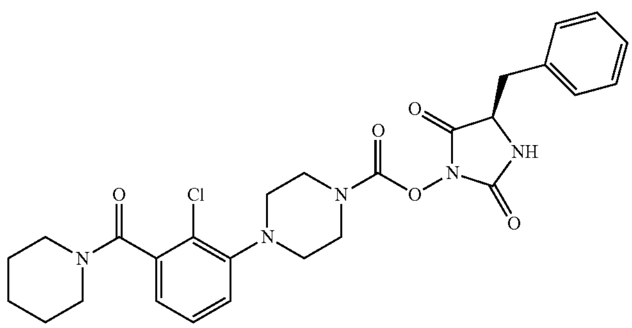 [SMILES: O=C(ON1C(=O)N[C@H](Cc2ccccc2)C1=O)N1CCN(c2cccc(C(=O)N3CCCCC3)c2Cl)CC1] | (R)-4-benzyl-2,5-dioxoimidazolidin-1-yl 4-(2-chloro-3-(piperidine-1-carbonyl)phenyl)piperazine-1-carboxylate |
| 12 | 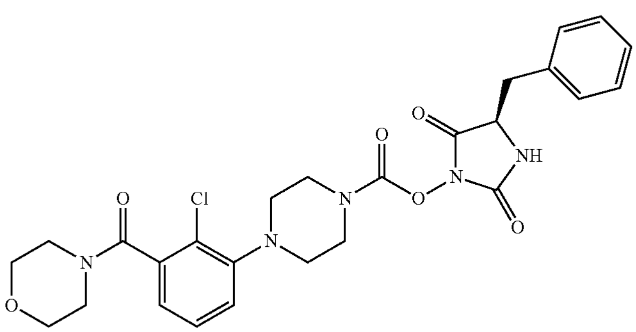 [SMILES: O=C(ON1C(=O)N[C@H](Cc2ccccc2)C1=O)N1CCN(c2cccc(C(=O)N3CCOCC3)c2Cl)CC1] | (R)-4-benzyl-2,5-dioxoimidazolidin-1-yl 4-(2-chloro-3-(morpholine-4-carbonyl)phenyl)piperazine-1-carboxylate |
| 13 | 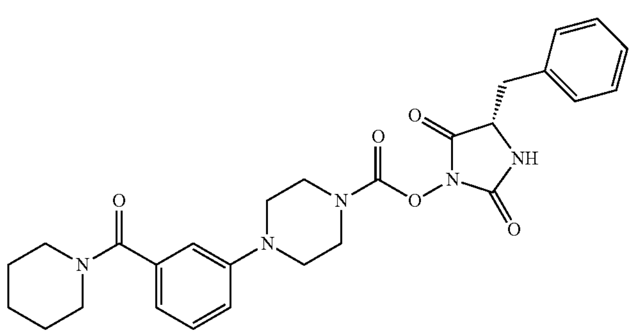 [SMILES: O=C(ON1C(=O)N[C@@H](Cc2ccccc2)C1=O)N1CCN(c2cccc(C(=O)N3CCCCC3)c2)CC1] | (S)-4-benzyl-2,5-dioxoimidazolidin-1-yl 4-(3-(piperidine-1-carbonyl)phenyl)piperazine-1-carboxylate |

TABLE 1-continued

| Chemical Synthesis Example | Structure | Name |
|---|---|---|
| 14 | 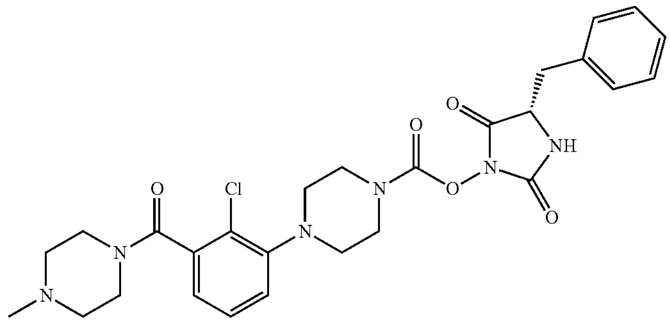 [SMILES: CN1CCN(C(=O)c2cccc(N3CCN(C(=O)ON4C(=O)N[C@@H](Cc5ccccc5)C4=O)CC3)c2Cl)CC1] | (S)-4-benzyl-2,5-dioxoimidazolidin-1-yl 4-(2-chloro-3-(4-methylpiperazine-1-carbonyl)phenyl)piperazine-1-carboxylate |
| 15 | 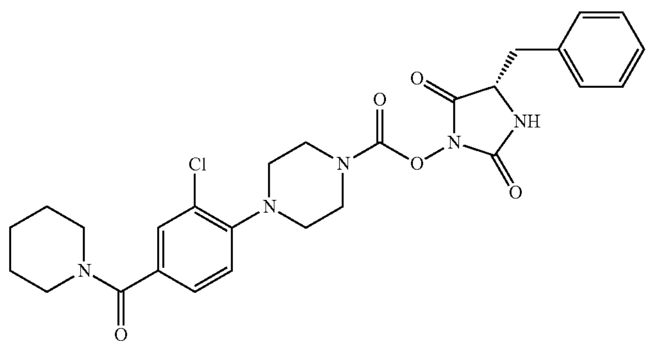 [SMILES: O=C(ON1C(=O)N[C@@H](Cc2ccccc2)C1=O)N1CCN(c2ccc(C(=O)N3CCCCC3)cc2Cl)CC1] | (S)-4-benzyl-2,5-dioxoimidazolidin-1-yl 4-(2-chloro-4-(piperidine-1-carbonyl)phenyl)piperazine-1-carboxylate |
| 16 | 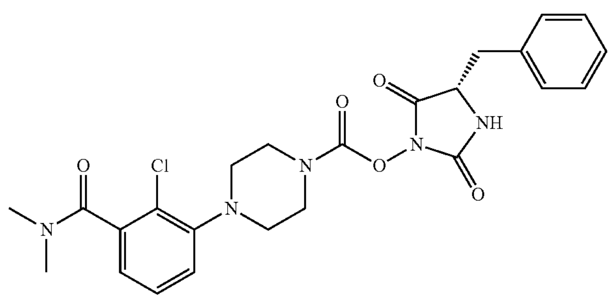 [SMILES: CN(C)C(=O)c1cccc(N2CCN(C(=O)ON3C(=O)N[C@@H](Cc4ccccc4)C3=O)CC2)c1Cl] | (S)-4-benzyl-2,5-dioxoimidazolidin-1-yl 4-(2-chloro-3-(dimethylcarbamoyl)phenyl)piperazine-1-carboxylate |
| 17 | 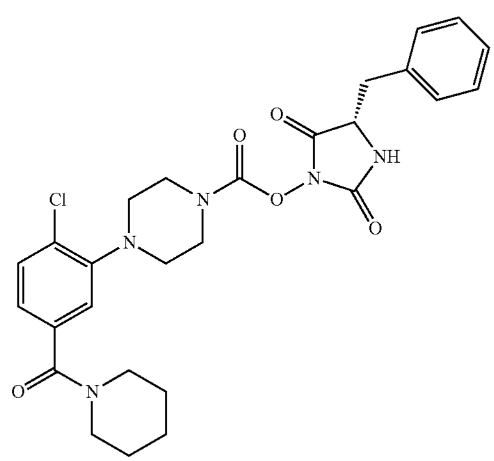 [SMILES: O=C(ON1C(=O)N[C@@H](Cc2ccccc2)C1=O)N1CCN(c2cc(C(=O)N3CCCCC3)ccc2Cl)CC1] | (S)-4-benzyl-2,5-dioxoimidazolidin-1-yl 4-(2-chloro-5-(piperidine-1-carbonyl)phenyl)piperazine-1-carboxylate |

TABLE 1-continued

| Chemical Synthesis Example | Structure | Name |
|---|---|---|
| 18 | 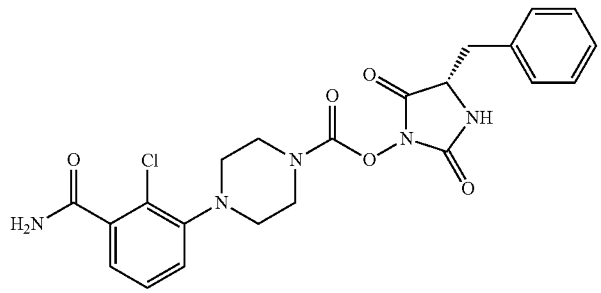 [SMILES: NC(=O)c1cccc(N2CCN(C(=O)ON3C(=O)N[C@@H](Cc4ccccc4)C3=O)CC2)c1Cl] | (S)-4-benzyl-2,5-dioxoimidazolidin-1-yl 4-(3-carbamoyl-2-chlorophenyl)piperazine-1-carboxylate |
| 19 | 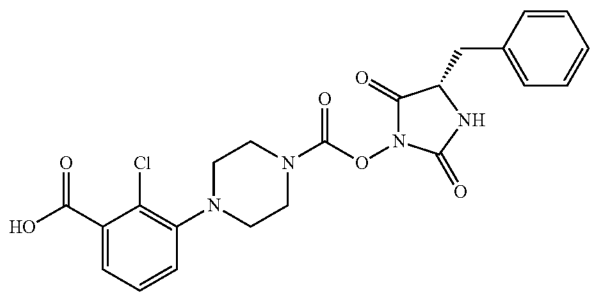 [SMILES: O=C(O)c1cccc(N2CCN(C(=O)ON3C(=O)N[C@@H](Cc4ccccc4)C3=O)CC2)c1Cl] | (S)-3-(4-((4-benzyl-2,5-dioxoimidazolidin-1-yloxy)carbonyl)piperazin-1-yl)-2-chlorobenzoic acid |
| 20 | 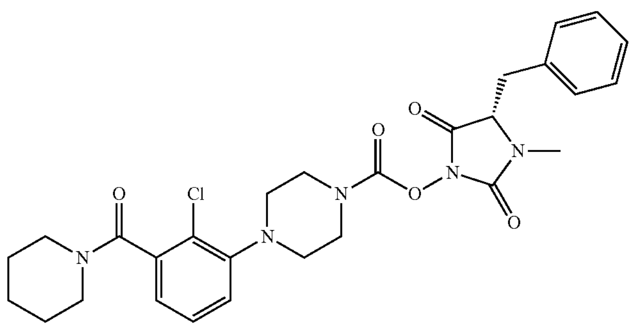 [SMILES: CN1C(=O)N(OC(=O)N2CCN(c3cccc(C(=O)N4CCCCC4)c3Cl)CC2)C(=O)[C@@H]1Cc1ccccc1] | (S)-4-benzyl-3-methyl-2,5-dioxoimidazolidin-1-yl 4-(2-chloro-3-(piperidine-1-carbonyl)phenyl)piperazine-1-carboxylate |
| 21 | 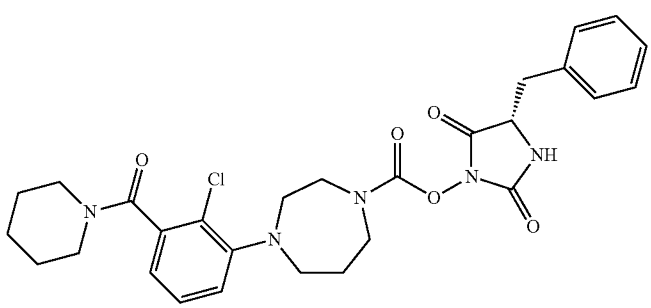 [SMILES: O=C(ON1C(=O)N[C@@H](Cc2ccccc2)C1=O)N1CCCN(c2cccc(C(=O)N3CCCCC3)c2Cl)CC1] | (S)-4-benzyl-2,5-dioxoimidazolidin-1-yl 4-(2-chloro-3-(piperidine-1-carbonyl)phenyl)-1,4-diazepane-1-carboxylate |
| 22 | 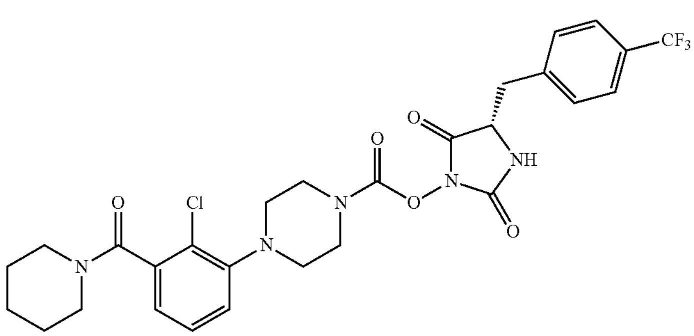 [SMILES: O=C(ON1C(=O)N[C@@H](Cc2ccc(C(F)(F)F)cc2)C1=O)N1CCN(c2cccc(C(=O)N3CCCCC3)c2Cl)CC1] | (S)-2,5-dioxo-4-(4-(trifluoromethyl)benzyl)imidazolidin-1-yl 4-(2-chloro-3-(piperidine-1-carbonyl)phenyl)piperazine-1-carboxylate |

TABLE 1-continued

| Chemical Synthesis Example | Structure | Name |
|---|---|---|
| 23 | 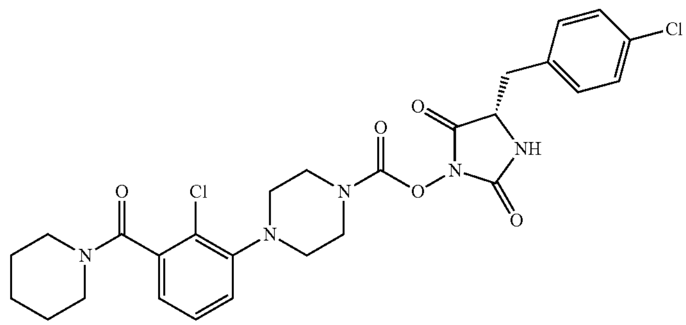 [SMILES: O=C(ON1C(=O)N[C@@H](Cc2ccc(Cl)cc2)C1=O)N1CCN(c2cccc(C(=O)N3CCCCC3)c2Cl)CC1] | (S)-4-(4-chlorobenzyl)-2,5-dioxoimidazolidin-1-yl 4-(2-chloro-3-(piperidine-1-carbonyl)phenyl)piperazine-1-carboxylate |
| 24 | 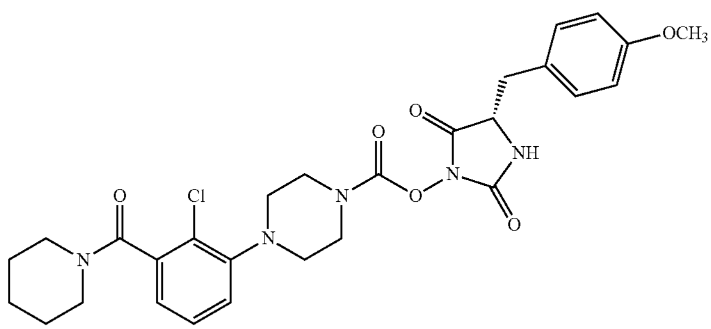 [SMILES: COc1ccc(C[C@@H]2NC(=O)N(OC(=O)N3CCN(c4cccc(C(=O)N5CCCCC5)c4Cl)CC3)C2=O)cc1] | (S)-4-(4-methoxybenzyl)-2,5-dioxoimidazolidin-1-yl 4-(2-chloro-3-(piperidine-1-carbonyl)phenyl)piperazine-1-carboxylate |

In some embodiments, the compound disclosed herein, or a pharmaceutically acceptable salt or solvate thereof, has the structure:

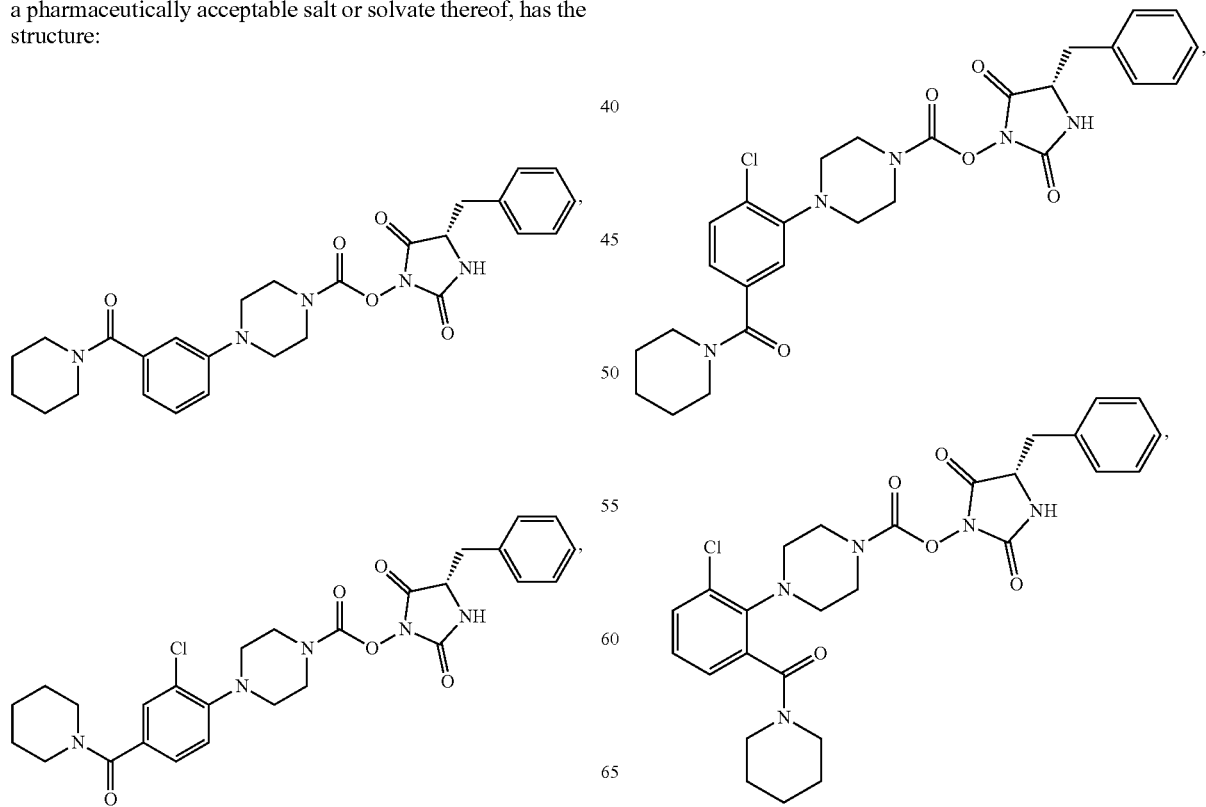

-continued

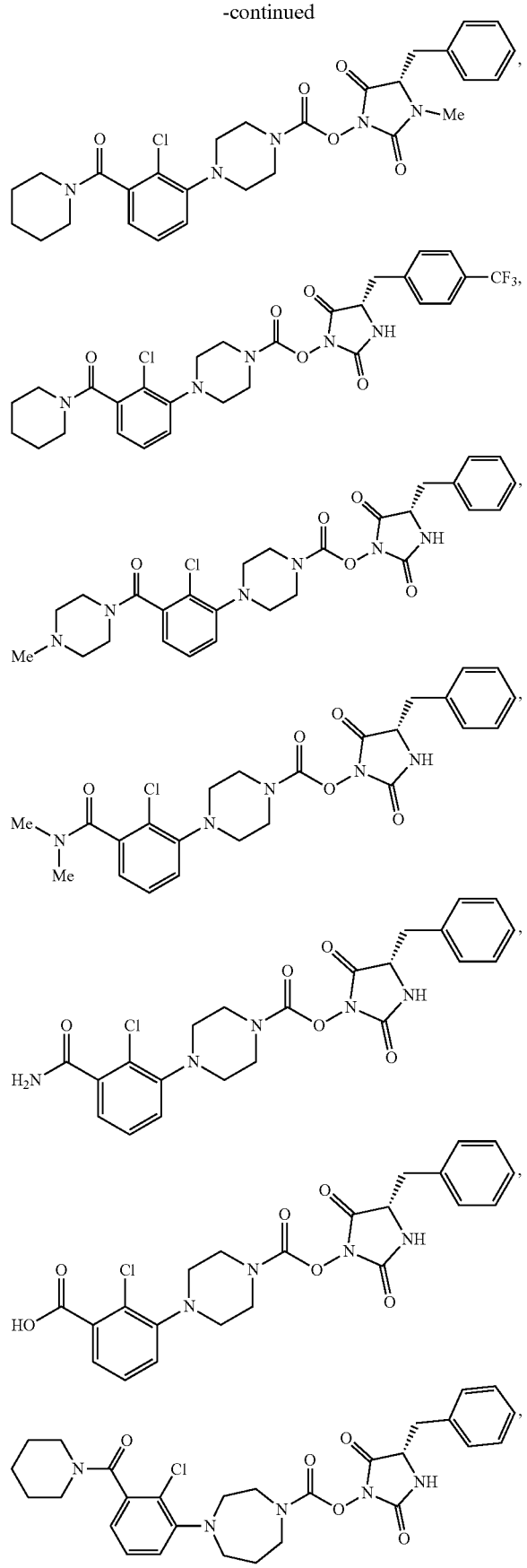

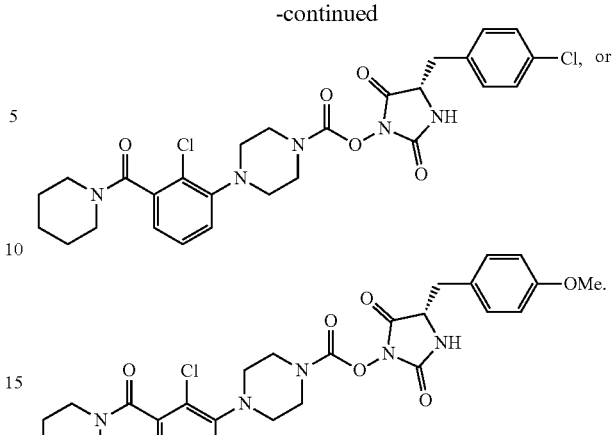

Preparation of the Compounds

The compound of Formula (I), (II), (IIa), (IIb), (IIc), or (IId) described herein are prepared by the methods described herein or other known chemical reactions. The compounds used in the reactions described herein are made according to known organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech, (Shanghai, China), TCI America (Portland, Oreg.), Trans World Chemicals, Inc. (Rockville, Md.), and WuXi (Shanghai, China).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Further Forms of Compounds Disclosed Herein
Isomers

Furthermore, in some embodiments, the compounds of Formula (I), (II), (IIa), (IIb), (IIc), or (IId) described herein exist as geometric isomers. In some embodiments, the compounds of Formula (I), (II), (IIa), (IIb), (IIc), or (IId) described herein possess one or more double bonds. The compounds of Formula (I), (II), (IIa), (IIb), (IIc), or (IId) presented herein include all cis, trans, syn, anti, entgegen (E), and zusammen (Z) isomers as well as the corresponding mixtures thereof. In some situations, compounds of Formula (I), (II), (IIa), (IIb), (IIc), or (IId) exist as tautomers. The compounds of Formula (I), (II), (IIa), (IIb), (IIc), or (IId) described herein include all possible tautomers within the formulas described herein. In some situations, the compounds of Formula (I), (II), (IIa), (IIb), (IIc), or (IId) described herein possess one or more chiral centers and each center exists in the R configuration, or S configuration. The compounds of Formula (I), (II), (IIa), (IIb), (IIc), or (IId) described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds of Formula (I), (II), (IIa), (IIb), (IIc), or (IId) described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds of Formula (I), (II), (IIa), (IIb), (IIc), or (IId) described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compound of Formula (I), (II), (IIa), (IIb), (IIc), or (IId) disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds of the invention include isotopes of hydrogen, carbon, nitrogen, oxygen, phosphorous, sulfur, fluorine and chloride, such as $^2$H, $^3$H, $^{13}$C, $^{14}$C $^{15}$N, $^{18}$O, $^{17}$O, $^{31}$P, $^{32}$P, $^{35}$S, $^{18}$F, and $^{36}$Cl, respectively. Compounds described herein, and pharmaceutically acceptable salts, esters, solvate, hydrates or derivatives thereof which contain the aforementioned isotopes and/or other isotopes of other atoms are within the scope of this invention. Certain isotopically-labeled compounds, for example those into which radioactive isotopes such as $^3$H and $^{14}$C are incorporated, are useful in drug and/or substrate tissue distribution assays. Tritiated, i.e., $^3$H and carbon-14, i.e., $^{14}$C, isotopes are particularly preferred for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate or derivative thereof is prepared by any suitable method.

In some embodiments, the compounds of Formula (I), (II), (IIa), (IIb), (IIc), or (IId) described herein are labeled by other means, including, but not limited to, the use of chromophores or fluorescent moieties, bioluminescent labels, or chemiluminescent labels.

Pharmaceutically Acceptable Salts

In some embodiments, the compounds of Formula (I), (II), (IIa), (IIb), (IIc), or (IId) described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds of Formula (I), (II), (IIa), (IIb), (IIc), or (IId) described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compound of Formula (I), (II), (IIa), (IIb), (IIc), or (IId) described herein, or by separately reacting a purified compound in its free form with a suitable acid or base, and isolating the salt thus formed.

Solvates

In some embodiments, the compounds of Formula (I), (II), (IIa), (IIb), (IIc), or (IId) described herein exist as a solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or methanol. In addition, the compounds provided herein exist in unsolvated as well as solvated forms. In general, the solvated forms are considered equivalent to the unsolvated forms for the purposes of the compounds and methods provided herein.

Pharmaceutical Compositions

In certain embodiments, the compound of Formula (I), (II), (IIa), (IIb), (IIc), or (IId) as described herein is administered as a pure chemical. In other embodiments, the compound of Formula (I), (II), (IIa), (IIb), (IIc), or (IId) described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Accordingly, provided herein is a pharmaceutical composition comprising at least one compound of Formula (I), (II), (IIa), (IIb), (IIc), or (IId) described herein, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound of Formula (I), or a pharmaceutically acceptable salt thereof.

One embodiment provides a pharmaceutical composition comprising a pharmaceutically acceptable carrier and a compound of Formula (II), or a pharmaceutically acceptable salt thereof.

One embodiment provides a pharmaceutical composition comprising a pharmaceutically acceptable carrier and a compound of Formula (IIa), or a pharmaceutically acceptable salt thereof.

One embodiment provides a pharmaceutical composition comprising a pharmaceutically acceptable carrier and a compound of Formula (IIb), or a pharmaceutically acceptable salt thereof.

One embodiment provides a pharmaceutical composition comprising a pharmaceutically acceptable carrier and a compound of Formula (IIc), or a pharmaceutically acceptable salt thereof.

One embodiment provides a pharmaceutical composition comprising a pharmaceutically acceptable carrier and a compound of Formula (IId), or a pharmaceutically acceptable salt thereof.

Another embodiment provides a pharmaceutical composition consisting essentially of a pharmaceutically acceptable carrier and a compound of Formula (I), or a pharmaceutically acceptable salt thereof. Another embodiment provides a pharmaceutical composition consisting essentially of a pharmaceutically acceptable carrier and a compound of Formula (II), or a pharmaceutically acceptable salt thereof. Another embodiment provides a pharmaceutical composition consisting essentially of a pharmaceutically acceptable carrier and a compound of Formula (IIa), or a pharmaceutically acceptable salt thereof. Another embodiment provides a pharmaceutical composition consisting essentially of a pharmaceutically acceptable carrier and a compound of Formula (IIb), or a pharmaceutically acceptable salt thereof. Another embodiment provides a pharmaceutical composition consisting essentially of a pharmaceutically acceptable carrier and a compound of Formula (IIc), or a pharmaceutically acceptable salt thereof. Another embodiment provides a pharmaceutical composition consisting essentially of a pharmaceutically acceptable carrier and a compound of Formula (IId), or a pharmaceutically acceptable salt thereof.

In certain embodiments, the compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, rectal, topical, buccal, parenteral (e.g., subcutaneous, intramuscular, intradermal, or intravenous), vaginal, or aerosol administration.

Methods

Disclosed herein are methods of modulating the activity of Lp-PLA2. Contemplated methods, for example, comprise exposing said enzyme to a compound described herein. In some embodiments, the compound utilized by one or more of the foregoing methods is one of the generic, subgeneric, or specific compounds described herein, such as a compound of Formula (I), (II), (IIa), (IIb), (IIc), or (IId). The ability of compounds described herein to modulate or inhibit Lp-PLA2 is evaluated by procedures known in the art and/or described herein. Another aspect of this disclosure provides methods of treating a disease associated with expression or activity of Lp-PLA2 in a patient. In some embodiments, provided herein are compounds that are selective in inhibiting Lp-PLA2, as compared to inhibition of other serine hydrolases e.g., FAAH, e.g., 10, 100, 1000 or more fold inhibition of Lp-PLA2 over FAAH. In other embodiments, disclosed compounds are more selective in inhibition of Lp-PLA2 as compared to ABHD6.

Also disclosed herein is a method of treating a disease, disorder or condition in a mammal that would benefit from lipoprotein-associated phospholipase A2 (Lp-PLA2) inhibition comprising administering to the mammal a therapeutically effective amount of a compound of Formula (I), (II), (IIa), (IIb), (IIc), or (IId), or a pharmaceutically acceptable salt, or solvate thereof. In some embodiments, disclosed herein is a method of treating a disease, disorder or condition in a mammal that would benefit from lipoprotein-associated phospholipase A2 (Lp-PLA2) inhibition comprising administering to the mammal a therapeutically effective amount of a compound of Formula (I), or a pharmaceutically acceptable salt, or solvate thereof. In some embodiments, disclosed herein is a method of treating a disease, disorder or condition in a mammal that would benefit from lipoprotein-associated phospholipase A2 (Lp-PLA2) inhibition comprising administering to the mammal a therapeutically effective amount of a compound of Formula (II), or a pharmaceutically acceptable salt, or solvate thereof. In some embodiments, disclosed herein is a method of treating a disease, disorder or condition in a mammal that would benefit from lipoprotein-associated phospholipase A2 (Lp-PLA2) inhibition comprising administering to the mammal a therapeutically effective amount of a compound of Formula (IIa), or a pharmaceutically acceptable salt, or solvate thereof. In some embodiments, disclosed herein is a method of treating a disease, disorder or condition in a mammal that would benefit from lipoprotein-associated phospholipase A2 (Lp-PLA2) inhibition comprising administering to the mammal a therapeutically effective amount of a compound of Formula (IIb), or a pharmaceutically acceptable salt, or solvate thereof. In some embodiments, disclosed herein is a method of treating a disease, disorder or condition in a mammal that would benefit from lipoprotein-associated phospholipase A2 (Lp-PLA2) inhibition comprising administering to the mammal a therapeutically effective amount of a compound of Formula (IIc), or a pharmaceutically acceptable salt, or solvate thereof. In some embodiments, disclosed herein is a method of treating a disease, disorder or condition in a mammal that would benefit from lipoprotein-associated phospholipase A2 (Lp-PLA2) inhibition comprising administering to the mammal a therapeutically effective amount of a compound of Formula (IId), or a pharmaceutically acceptable salt, or solvate thereof.

In some embodiments, disclosed herein is a method of treating ischemia, traumatic brain injury, multiple sclerosis, diabetes, Alzheimer's disease, Parkinson's disease, amyotrophic lateral sclerosis (ALS), or cancer in a mammal comprising administering to the mammal in need thereof, a therapeutically effective amount of a compound of Formula (I), (II), (IIa), (IIb), (IIc), or (IId), or a pharmaceutically acceptable salt, or solvate thereof. In some embodiments, disclosed herein is a method of treating ischemia, traumatic brain injury, multiple sclerosis, diabetes, Alzheimer's disease, Parkinson's disease, amyotrophic lateral sclerosis (ALS), or cancer in a mammal comprising administering to the mammal in need thereof, a therapeutically effective amount of a compound of Formula (I), or a pharmaceutically acceptable salt, or solvate thereof. In some embodiments, disclosed herein is a method of treating ischemia, traumatic brain injury, multiple sclerosis, diabetes, Alzheimer's disease, Parkinson's disease, amyotrophic lateral sclerosis (ALS), or cancer in a mammal comprising administering to the mammal in need thereof, a therapeutically effective amount of a compound of Formula (II), or a pharmaceutically acceptable salt, or solvate thereof. In some embodiments, disclosed herein is a method of treating ischemia, traumatic brain injury, multiple sclerosis, diabetes, Alzheimer's disease, Parkinson's disease, amyotrophic lateral sclerosis (ALS), or cancer in a mammal comprising administering to the mammal in need thereof, a therapeutically effective amount of a compound of Formula (IIa), or a pharmaceutically acceptable salt, or solvate thereof. In some embodiments, disclosed herein is a method of treating ischemia, traumatic brain injury, multiple sclerosis, diabetes, Alzheimer's disease, Parkinson's disease, amyotrophic lateral sclerosis (ALS), or cancer in a mammal comprising administering to the mammal in need thereof, a therapeutically effective amount of a compound of Formula (IIb), or a pharmaceutically acceptable salt, or solvate thereof. In some embodiments, disclosed herein is a method of treating ischemia, traumatic brain injury, multiple sclerosis, diabetes, Alzheimer's disease, Parkinson's disease, amyotrophic lateral sclerosis (ALS), or cancer in a mammal comprising administering to the mammal in need thereof, a therapeutically effective amount of a compound of Formula (IIc), or a pharmaceutically acceptable salt, or solvate thereof. In some embodiments, disclosed herein is a method of treating ischemia, traumatic brain injury, multiple sclerosis, diabetes, Alzheimer's disease, Parkinson's disease, amyotrophic lateral sclerosis (ALS), or cancer in a mammal comprising administering to the mammal in need thereof, a therapeutically effective amount of a compound of Formula (IId), or a pharmaceutically acceptable salt, or solvate thereof.

In some embodiments, disclosed herein is the use of a compound of Formula (I), (II), (IIa), (IIb), (IIc), or (IId), or a pharmaceutically acceptable salt, or solvate thereof for treating a disease, disorder or condition in a mammal that would benefit from lipoprotein-associated phospholipase A2 (Lp-PLA2) inhibition. In some embodiments, disclosed herein is the use of a compound of Formula (I), or a pharmaceutically acceptable salt, or solvate thereof, for treating a disease, disorder or condition in a mammal that would benefit from lipoprotein-associated phospholipase A2 (Lp-PLA2) inhibition. In some embodiments, disclosed herein is the use of a compound of Formula (II), or a pharmaceutically acceptable salt, or solvate thereof, for treating a disease, disorder or condition in a mammal that would benefit from lipoprotein-associated phospholipase A2 (Lp-PLA2) inhibition. In some embodiments, disclosed herein is the use of a compound of Formula (IIa), or a pharmaceutically acceptable salt, or solvate thereof, for treating a disease, disorder or condition in a mammal that would benefit from lipoprotein-associated phospholipase A2 (Lp-PLA2) inhibition. In some embodiments, disclosed herein is the use of a compound of Formula (IIb), or a pharmaceutically acceptable salt, or solvate thereof, for treating a disease, disorder or condition in a mammal that would benefit from lipoprotein-associated phospholipase A2 (Lp-PLA2) inhibition. In some embodiments, disclosed herein is the use of a compound of Formula (IIc), or a pharmaceutically acceptable salt, or solvate thereof, for treating a disease, disorder or condition in a mammal that would benefit from lipoprotein-associated phospholipase A2 (Lp-PLA2) inhibition. In some embodiments, disclosed herein is the use of a compound of Formula (IId), or a pharmaceutically acceptable salt, or solvate thereof, for treating a disease, disorder or condition in a mammal that would benefit from lipoprotein-associated phospholipase A2 (Lp-PLA2) inhibition.

In some embodiments, disclosed herein is the use of a compound of Formula (I), (II), (IIa), (IIb), (IIc), or (IId), or a pharmaceutically acceptable salt, or solvate thereof, in the manufacture of a medicament for the treatment of a disease, disorder or condition in a mammal that would benefit from lipoprotein-associated phospholipase A2 (Lp-PLA2) inhibition. In some embodiments, disclosed herein is the use of a compound of Formula (I), (II), (IIa), (IIb), (IIc), or (IId), or a pharmaceutically acceptable salt, or solvate thereof, in the manufacture of a medicament for the treatment of a disease, disorder or condition in a mammal that would benefit from lipoprotein-associated phospholipase A2 (Lp-PLA2) inhibition.

In some embodiments, disclosed herein is the use of a compound of Formula (I), (II), (IIa), (IIb), (IIc), or (IId), or a pharmaceutically acceptable salt, or solvate thereof, in the manufacture of a medicament for the treatment of a disease, disorder or condition in a mammal that would benefit from lipoprotein-associated phospholipase A2 (Lp-PLA2) inhibition. In some embodiments, disclosed herein is the use of a compound of Formula (I), or a pharmaceutically acceptable salt, or solvate thereof, in the manufacture of a medicament for the treatment of a disease, disorder or condition in a mammal that would benefit from lipoprotein-associated phospholipase A2 (Lp-PLA2) inhibition. In some embodiments, disclosed herein is the use of a compound of Formula (II), or a pharmaceutically acceptable salt, or solvate thereof, in the manufacture of a medicament for the treatment of a disease, disorder or condition in a mammal that would benefit from lipoprotein-associated phospholipase A2 (Lp-PLA2) inhibition. In some embodiments, disclosed herein is the use of a compound of Formula (IIa), or a pharmaceutically acceptable salt, or solvate thereof, in the manufacture of a medicament for the treatment of a disease, disorder or condition in a mammal that would benefit from lipoprotein-associated phospholipase A2 (Lp-PLA2) inhibition. In some embodiments, disclosed herein is the use of a compound of Formula (IIb), or a pharmaceutically acceptable salt, or solvate thereof, in the manufacture of a medicament for the treatment of a disease, disorder or condition in a mammal that would benefit from lipoprotein-associated phospholipase A2 (Lp-PLA2) inhibition. In some embodiments, disclosed herein is the use of a compound of Formula (IIc), or a pharmaceutically acceptable salt, or solvate thereof, in the manufacture of a medicament for the treatment of a disease, disorder or condition in a mammal that would benefit from lipoprotein-associated phospholipase A2 (Lp-PLA2) inhibition. In some embodiments, disclosed herein is the use of a compound of Formula (IId), or a pharmaceutically acceptable salt, or solvate thereof, in the manufacture of a medicament for the treatment of a disease, disorder or condition in a mammal that would benefit from lipoprotein-associated phospholipase A2 (Lp-PLA2) inhibition.

In certain embodiments, a disclosed compound utilized by one or more of the foregoing methods is one of the generic, subgeneric, or specific compounds described herein, such as a compound of Formula (I), (II), (IIa), (IIb), (IIc), or (IId).

Disclosed compounds are administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray or rectally in dosage unit formulations containing conventional non-toxic pharmaceutically acceptable carriers, adjuvants and vehicles. Parenteral administration include subcutaneous injections, intravenous or intramuscular injections or infusion techniques.

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as, conventional oral dosage forms, that are administered either simultaneously or sequentially.

The following examples are provided merely as illustrative of various embodiments and shall not be construed to limit the invention in any way.

EXAMPLES

List of Abbreviations

As used above, and throughout the description of the invention, the following abbreviations, unless otherwise indicated, shall be understood to have the following meanings:

ACN or MeCN acetonitrile
Bn benzyl
BOC or Boc tert-butyl carbamate
CDI 1,1'-carbonyldiimidazole
Cy cyclohexyl
DCE dichloroethane (ClCH$_2$CH$_2$Cl)
DCM dichloromethane (CH$_2$Cl$_2$)
DIPEA or DIEA diisopropylethylamine
DMAP 4-(N,N-dimethylamino)pyridine
DMF dimethylformamide
DMA N,N-dimethylacetamide
DMSO dimethylsulfoxide
equiv equivalent(s)
Et ethyl
EtOH ethanol
EtOAc ethyl acetate
HATU 1-[bis(dimethylamino)methylene]-1H-1,2,3-triazolo[4,5-b]pyridinium 3-oxid hexafluorophosphate
HFIP 1,1,1,3,3,3-hexafluoropropan-2-ol
HPLC high performance liquid chromatography
LAH lithium aluminum hydride
Me methyl
MeOH methanol
MS mass spectroscopy
NMM N-methylmorpholine
NMR nuclear magnetic resonance
PMB para-methoxybenzyl
TEA triethylamine
TFA trifluoroacetic acid
THF tetrahydrofuran
TLC thin layer chromatography I. Chemical Synthesis Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

Example 1: (S)-4-isopropyl-2,5-dioxoimidazolidin-1-yl 4-(2-chloro-3-(pyrrolidine-1-carbonyl)phenyl)piperazine-1-carboxylate

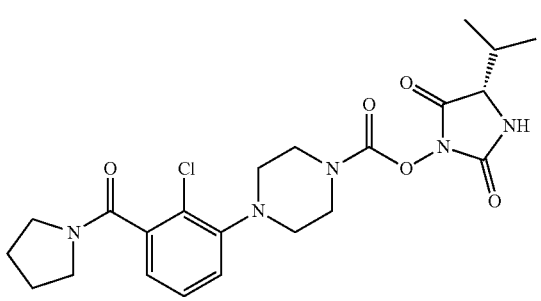 [SMILES: CC(C)[C@@H]1NC(=O)N(OC(=O)N2CCN(c3cccc(C(=O)N4CCCC4)c3Cl)CC2)C1=O]

Step 1: Preparation of (S)-tert-butyl 1-(benzyloxyamino)-3-methyl-1-oxobutan-2-ylcarbamate

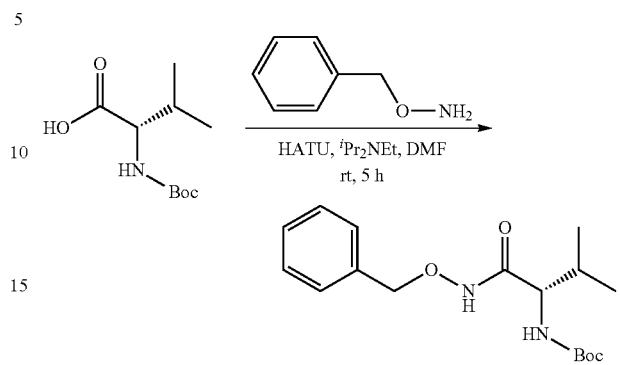

A 100-mL round-bottom flask was charged with (S)-2-(tert-butoxycarbonylamino)-3-methylbutanoic acid (8.68 g, 40.1 mmol, 1.00 equiv), and DMF (50 mL). N,N,N',N'-Tetramethyl-O-(7-azabenzotriazol-1-yl)uronium hexafluorophosphate (22.8 g, 60.3 mmol, 1.50 equiv) was added at 0° C., followed by dropwise addition of DIEA (20.6 g, 158 mmol, 4.00 equiv). The resulting solution was allowed to stir for 0.5 h at 0° C. O-Benzylhydroxylamine hydrochloride (9.54 g, 60.0 mmol, 1.50 equiv) was added, and the resulting solution was allowed to stir for 5 h at room temperature and quenched with H$_2$O (250 mL). The mixture was extracted with DCM (4×150 mL) and the organic layers were combined, washed with brine (3×100 mL), dried over anhydrous sodium sulfate, filtered, and concentrated under reduced pressure. The residue was chromatographed on a silica gel column with EtOAc/petroleum ether (1/1) to provide 11.9 g (92% yield) of (S)-tert-butyl 1-(benzyloxyamino)-3-methyl-1-oxobutan-2-ylcarbamate as a white solid. LCMS (ESI, m/z): 323 [M+H]$^+$.

Step 2: Preparation of (S)-2-amino-N-(benzyloxy)-3-methylbutanamide hydrochloride

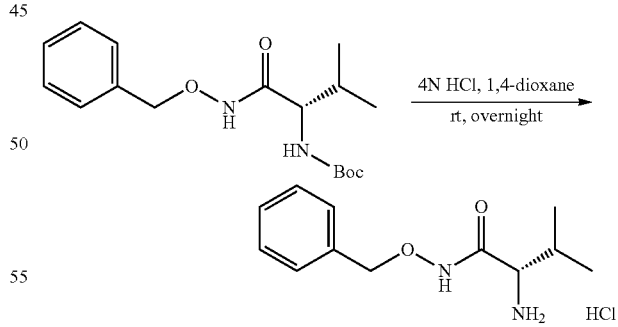

A 250-mL round-bottom flask was charged with (S)-tert-butyl 1-(benzyloxyamino)-3-methyl-1-oxobutan-2-ylcarbamate (11.9 g, 36.9 mmol, 1.00 equiv), hydrochloric acid (4 mol/L, 18 mL), and dioxane (130 mL). The resulting solution was allowed to stir overnight at room temperature and concentrated under reduced pressure to provide 7.91 g (83% yield) of (S)-2-amino-N-(benzyloxy)-3-methylbutanamide hydrochloride as a brown oil. LCMS (ESI, m/z): 223 [M+H]$^+$.

Step 3: Preparation (S)-3-(benzyloxy)-5-isopropylimidazolidine-2,4-dione

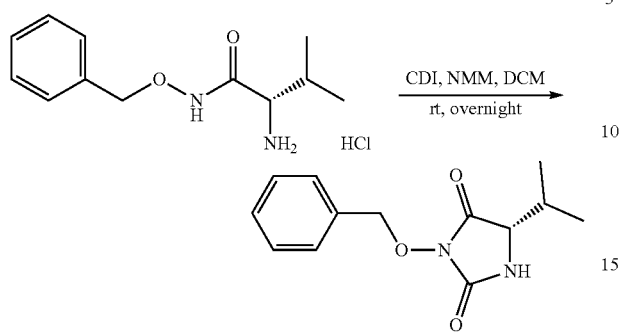

A 100-mL round-bottom flask was charged with (S)-2-amino-N-(benzyloxy)-3-methylbutanamide hydrochloride (9.31 g, 35.9 mmol, 1.00 equiv), DCM (50 mL), and NMM (18.2 g, 178 mmol, 5.00 equiv). CDI (8.75 g, 53.9 mmol, 1.50 equiv) was added, and the resulting solution was allowed to stir overnight at room temperature and quenched with H₂O (250 mL). The mixture was extracted with DCM (4×150 mL) and the organic layers were combined, washed with brine (3×100 mL), dried over anhydrous sodium sulfate, filtered and concentrated under reduced pressure. The residue was chromatographed on a silica gel column with EtOAc/petroleum ether (1/1) to provide 6.22 g (69% yield) of (S)-3-(benzyloxy)-5-isopropylimidazolidine-2,4-dione as a white solid. LCMS (ESI, m/z): 249 [M+H]⁺.

Step 4: Preparation of (S)-3-hydroxy-5-isopropylimidazolidine-2,4-dione

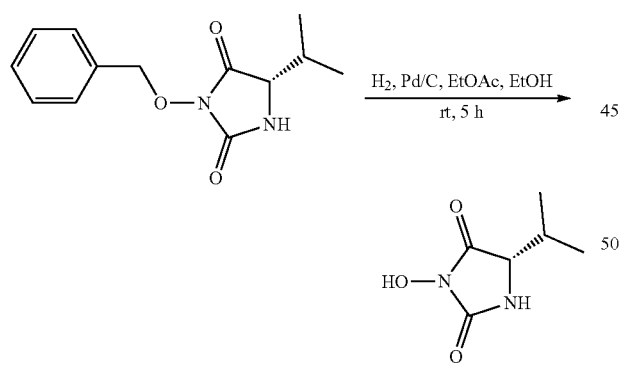

A 250-mL round-bottom flask was charged with (S)-3-(benzyloxy)-5-isopropylimidazolidine-2,4-dione (6.21 g, 25.1 mmol, 1.00 equiv), Pd/C (3.02 g), EtOH (60 mL), and EtOAc (15 mL). The resulting solution was maintained under a hydrogen atmosphere while stirring for 5 h at room temperature. The solids were removed by filtration and the resulting solution was concentrated under reduced pressure to provide 2.21 g (56% yield) of (S)-3-hydroxy-5-isopropylimidazolidine-2,4-dione as a white solid. LCMS (ESI, m/z): 159 [M+H]⁺.

Step 5: Preparation of 3-bromo-2-chlorobenzoyl chloride

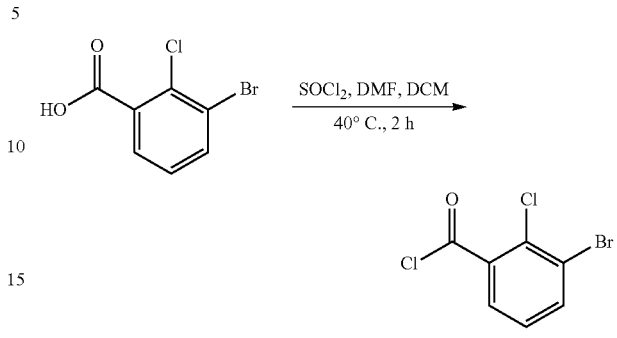

A 100-mL round-bottom flask was charged with 3-bromo-2-chlorobenzoic acid (4.51 g, 19.1 mmol, 1.00 equiv), DCM (150 mL), DMF (2.5 mL, 32 mmol, 1.7 equiv), and thionyl chloride (4.52 g, 38.0 mmol, 2.00 equiv). The resulting solution was allowed to stir for 2 h at 40° C. and concentrated under reduced pressure to provide 4.86 g (100% yield) of 3-bromo-2-chlorobenzoyl chloride as a light yellow oil.

Step 6: Preparation of (3-bromo-2-chlorophenyl)(pyrrolidin-1-yl)methanone

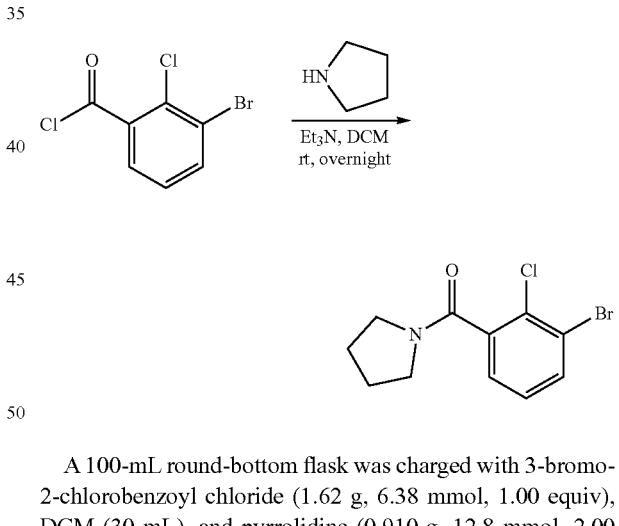

A 100-mL round-bottom flask was charged with 3-bromo-2-chlorobenzoyl chloride (1.62 g, 6.38 mmol, 1.00 equiv), DCM (30 mL), and pyrrolidine (0.910 g, 12.8 mmol, 2.00 equiv). TEA (1.93 g, 19.1 mmol, 3.00 equiv) was added dropwise, and the resulting solution was allowed to stir overnight at room temperature and quenched with H₂O (50 mL). The mixture was extracted with DCM (3×100 mL) and the organic layers were combined, washed with brine (3×100 mL), dried over anhydrous sodium sulfate, filtered and concentrated under reduced pressure. The residue was chromatographed on a silica gel column with EtOAc/petroleum ether (2/8) to provide 1.26 g (68% yield) of (3-bromo-2-chlorophenyl)(pyrrolidin-1-yl)methanone as a light yellow oil. LCMS (ESI, m/z): 290 [M+H]⁺.

Step 7: Preparation of tert-butyl 4-(2-chloro-3-(pyrrolidine-1-carbonyl)phenyl)piperazine-1-carboxylate

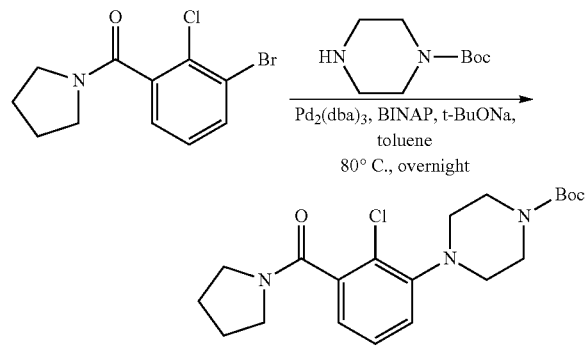

A 100-mL round-bottom flask was charged with (3-bromo-2-chlorophenyl)(pyrrolidin-1-yl)methanone (1.26 g, 2.88 mmol, 1.00 equiv), tert-butyl piperazine-1-carboxylate (0.803 g, 4.31 mmol, 1.50 equiv), tris(dibenzylideneacetone)dipalladium (0.132 g, 0.144 mmol, 0.05 equiv), bis(diphenylphosphino)-1,1'-binaphthyl (0.268 g, 0.431 mmol, 0.15 equiv), sodium tert-butoxide (0.414 g, 4.31 mmol, 1.50 equiv), and toluene (20 mL) under nitrogen. The resulting solution was allowed to stir overnight at 80° C. and quenched with H$_2$O (50 mL). The mixture was extracted with DCM (3×50 mL) and the organic layers were combined, dried over anhydrous sodium sulfate, filtered and concentrated under reduced pressure. The residue was chromatographed on a silica gel column with EtOAc/petroleum ether (1/1) to provide 0.926 g (54% yield) of tert-butyl 4-(2-chloro-3-(pyrrolidine-1-carbonyl)phenyl)piperazine-1-carboxylate as a yellow oil. LCMS (ESI, m/z): 394 [M+H]$^+$.

Step 8: Preparation of (2-chloro-3-(piperazin-1-yl)phenyl)(pyrrolidin-1-yl)methanone

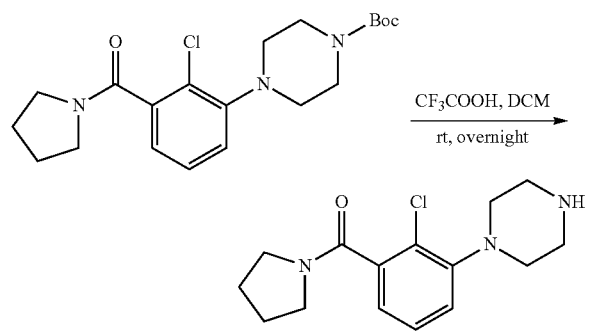

A 100-mL round-bottom flask was charged with tert-butyl 4-(2-chloro-3-(pyrrolidine-1-carbonyl)phenyl)piperazine-1-carboxylate (926 mg, 2.35 mmol, 1.00 equiv), TFA (2 mL), and DCM (14 mL). The resulting solution was allowed to stir overnight at room temperature and concentrated under reduced pressure. The crude product was dissolved in 1M NaOH solution (10 mL) and extracted with DCM (3×20 mL). The organic layers were combined, washed with brine (10 mL), dried over anhydrous sodium sulfate, filtered and concentrated under reduced pressure to provide 0.681 g (98% yield) of 4-(2-chloro-3-(pyrrolidine-1-carbonyl)phenyl)piperazine as a yellow oil. LCMS (ESI, m/z): 294 [M+H]$^+$.

Step 9: Preparation of 4-(2-chloro-3-(pyrrolidine-1-carbonyl)phenyl)piperazine-1-carbonyl chloride

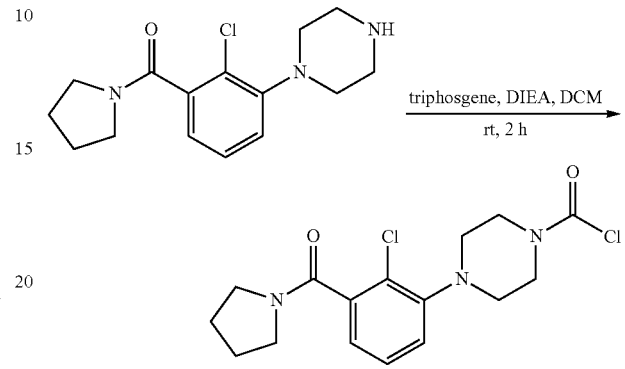

A 40-mL round-bottom flask was charged with triphosgene (76.5 mg, 0.261 mmol, 0.50 equiv) and DCM (5 mL). (2-Chloro-3-(piperazin-1-yl)phenyl)(pyrrolidin-1-yl)methanone (150 mg, 0.511 mmol, 1.00 equiv) was added at 0° C., followed by dropwise addition of DIEA (395 mg, 3.06 mmol, 6.00 equiv). The resulting solution was allowed to stir for 2 h at room temperature and quenched with H$_2$O (50 mL). The mixture was extracted with DCM (3×30 mL) and the organic layers were combined, washed with brine (3×100 mL), dried over anhydrous sodium sulfate, filtered and concentrated under reduced pressure to provide 180 mg (99% yield) of 4-(2-chloro-3-(pyrrolidine-1-carbonyl)phenyl)piperazine-1-carbonyl chloride as a yellow oil. LCMS (ESI, m/z): 356 [M+H]$^+$.

Step 10: Preparation of (S)-4-isopropyl-2,5-dioxoimidazolidin-1-yl 4-(2-chloro-3-(pyrrolidine-1-carbonyl)phenyl)piperazine-1-carboxylate

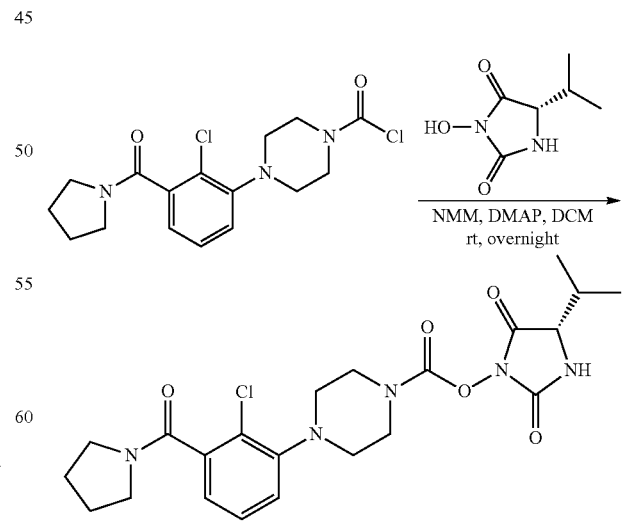

A 100-mL round-bottom flask was charged with 4-(2-chloro-3-(pyrrolidine-1-carbonyl)phenyl)piperazine-1-carbonyl chloride (180 mg, 0.511 mmol, 1.00 equiv), (S)-3-hydroxy-5-isopropylimidazolidine-2,4-dione (96.6 mg, 0.612 mmol, 1.20 equiv), NMM (152 mg, 1.50 mmol, 3.00 equiv), DMAP (6.12 mg, 0.0511 mmol, 0.10 equiv), and DCM (5 mL). The resulting solution was allowed to stir overnight at room temperature and concentrated under reduced pressure. The crude product (260 mg) was purified by preparative HPLC to afford 63.9 mg (26% yield) of (S)-4-isopropyl-2,5-dioxoimidazolidin-1-yl 4-(2-chloro-3-(pyrrolidine-1-carbonyl)phenyl)piperazine-1-carboxylate as a white solid. $^1$H NMR (300 MHz, Chloroform-d) δ 7.26-7.32 (m, 1H), 7.04 (d, J=7.8 Hz, 2H), 6.03 (br, 1H), 4.03-4.04 (m, 1H), 3.65-3.84 (m, 6H), 2.88-3.18 (m, 6H), 2.24-2.35 (m, 1H), 1.87-2.01 (m, 4H), 1.24 (d, J=8.1 Hz, 3H), 1.09 (d, J=8.1 Hz, 3H). LCMS (ESI, m/z): 478 [M+H]$^+$.

Example 2: (S)-4-isopropyl-2,5-dioxoimidazolidin-1-yl 4-(2-chloro-3-(piperidine-1-carbonyl)phenyl)piperazine-1-carboxylate

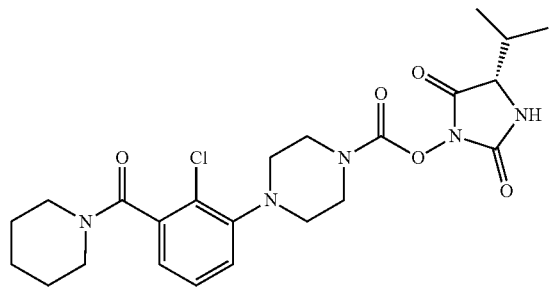 [SMILES: CC(C)[C@@H]1NC(=O)N(OC(=O)N2CCN(c3cccc(C(=O)N4CCCCC4)c3Cl)CC2)C1=O]

The title compound was synthesized as described in Example 1 using piperidine in Step 6. Purification resulted in 20.8 mg (10% yield) of (S)-4-isopropyl-2,5-dioxoimidazolidin-1-yl 4-(2-chloro-3-(piperidine-1-carbonyl)phenyl)piperazine-1-carboxylate as a white solid. $^1$H NMR (300 MHz, Chloroform-d) δ 7.26-7.31 (m, 1H), 6.98-7.07 (m, 2H), 5.76-5.92 (m, 1H), 4.04 (br, 1H), 3.72-3.84 (m, 6H), 3.12-3.20 (m, 4H), 3.00-3.04 (m, 2H), 2.74-2.31 (m, 1H), 1.67 (br, 4H), 1.47 (br, 2H), 1.09 (d, J=6.9 Hz, 3H), 1.03 (d, J=6.9 Hz, 3H). LCMS (ESI, m/z): 492 [M+H]$^+$.

Example 3: (S)-4-isopropyl-2,5-dioxoimidazolidin-1-yl 4-(2-chloro-3-(morpholine-4-carbonyl)phenyl)piperazine-1-carboxylate

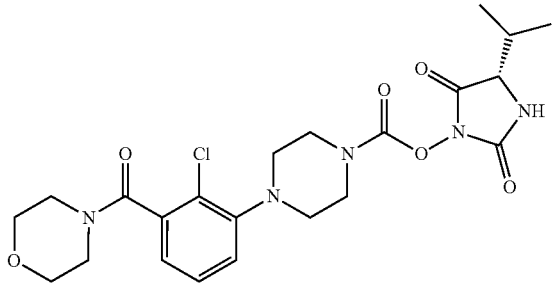 [SMILES: CC(C)[C@@H]1NC(=O)N(OC(=O)N2CCN(c3cccc(C(=O)N4CCOCC4)c3Cl)CC2)C1=O]

The title compound was synthesized as described in Example 1 using morpholine in Step 6. Purification resulted in 27.9 mg (14% yield) of (S)-4-isopropyl-2,5-dioxoimidazolidin-1-yl 4-(2-chloro-3-(morpholine-4-carbonyl)phenyl)piperazine-1-carboxylate as a white solid. $^1$H NMR (300 MHz, Chloroform-d) δ 7.26-7.31 (m, 1H), 7.07 (d, J=6.9 Hz, 1H), 7.00 (d, J=8.7 Hz, 1H), 5.56 (br, 1H), 4.05-4.06 (m, 1H), 3.68-3.91 (m, 9H), 3.59-3.67 (m, 1H), 3.19-3.27 (m, 4H), 2.97-3.05 (m, 2H), 2.59-2.32 (m, 1H), 1.09 (d, J=6.9 Hz, 3H), 1.04 (d, J=6.9 Hz, 3H). LCMS (ESI, m/z): 494 [M+H]$^+$.

Example 4: (R)-4-isopropyl-2,5-dioxoimidazolidin-1-yl 4-(2-chloro-3-(pyrrolidine-1-carbonyl)phenyl)piperazine-1-carboxylate

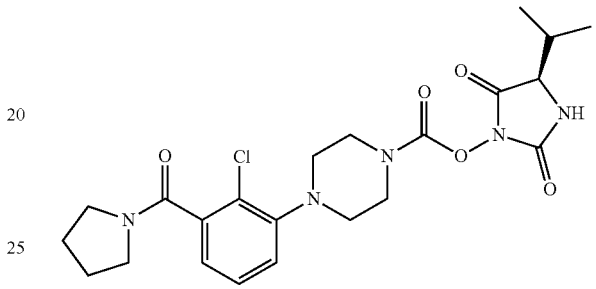

The title compound was synthesized as described in Example 1 using (R)-2-(tert-butoxycarbonylamino)-3-methylbutanoic acid in Step 1. Purification resulted in 31.5 mg (20% yield) of (R)-4-isopropyl-2,5-dioxoimidazolidin-1-yl 4-(2-chloro-3-(pyrrolidine-1-carbonyl)phenyl)piperazine-1-carboxylate as a white solid. $^1$H NMR (300 MHz, Chloroform-d) δ 7.26-7.32 (m, 1H), 7.01-7.05 (m, 2H), 6.31 (br, 1H), 4.02-4.03 (m, 1H), 3.64-3.84 (m, 6H), 3.10-3.18 (m, 6H), 2.24-2.34 (m, 1H), 1.85-2.02 (m, 4H), 1.29 (d, J=6.9 Hz, 3H), 1.25 (d, J=3.9 Hz, 3H). LCMS (ESI, m/z): 478 [M+H]$^+$.

Example 5: (R)-4-isopropyl-2,5-dioxoimidazolidin-1-yl 4-(2-chloro-3-(piperidine-1-carbonyl)phenyl)piperazine-1-carboxylate

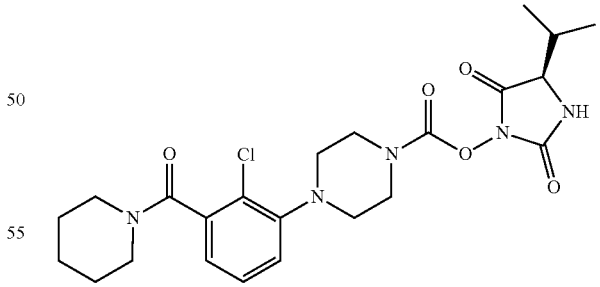

The title compound was synthesized as described in Example 2 using (R)-2-(tert-butoxycarbonylamino)-3-methylbutanoic acid in Step 1. Purification resulted in 51.0 mg (27% yield) of (R)-4-isopropyl-2,5-dioxoimidazolidin-1-yl 4-(2-chloro-3-(piperidine-1-carbonyl)phenyl)piperazine-1-carboxylate as a white solid. $^1$H NMR (300 MHz, Chloroform-d) δ 7.25-7.31 (m, 1H), 6.97-7.05 (m, 2H), 6.04 (br, 1H), 4.02-4.03 (m, 1H), 3.72-3.83 (m, 6H), 3.10-3.22 (m, 4H), 2.99-3.03 (m, 2H), 2.24-2.35 (m, 1H), 1.67-1.86 (m, 4H), 1.45-1.47 (m, 2H), 1.29 (d, J=6.9 Hz, 3H), 1.25 (d, J=3.9 Hz, 3H). LCMS (ESI, m/z): 492 [M+H]+.

Example 6: (R)-4-isopropyl-2,5-dioxoimidazolidin-1-yl 4-(2-chloro-3-(morpholine-4-carbonyl)phenyl)piperazine-1-carboxylate

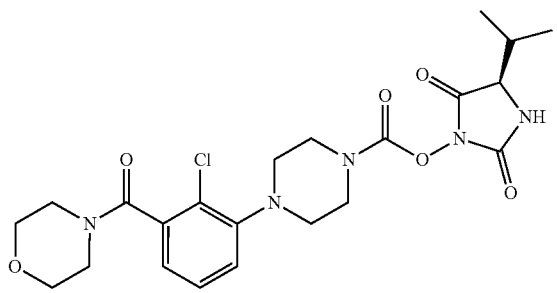 [SMILES: CC(C)[C@H]1NC(=O)N(OC(=O)N2CCN(c3cccc(C(=O)N4CCOCC4)c3Cl)CC2)C1=O]

The title compound was synthesized as described in Example 3 using (R)-2-(tert-butoxycarbonylamino)-3-methylbutanoic acid in Step 1. Purification resulted in 17.8 mg (11% yield) of (R)-4-isopropyl-2,5-dioxoimidazolidin-1-yl 4-(2-chloro-3-(morpholine-4-carbonyl)phenyl)piperazine-1-carboxylate as a white solid. $^1$H NMR (300 MHz, Chloroform-d) δ 7.26-7.30 (m, 1H), 7.01-7.08 (m, 1H), 6.99-7.00 (m, 1H), 5.49 (br, 1H), 4.05-4.06 (m, 1H), 3.59-3.91 (m, 10H), 3.20-3.27 (m, 4H), 2.97-3.04 (m, 2H), 2.30-2.32 (m, 1H), 1.09 (d, J=6.9 Hz, 3H), 1.04 (d, J=6.6 Hz, 3H). LCMS (ESI, m/z): 494 [M+H]+.

Example 7: (S)-4-benzyl-2,5-dioxoimidazolidin-1-yl 4-(2-chloro-3-(pyrrolidine-1-carbonyl)phenyl)piperazine-1-carboxylate

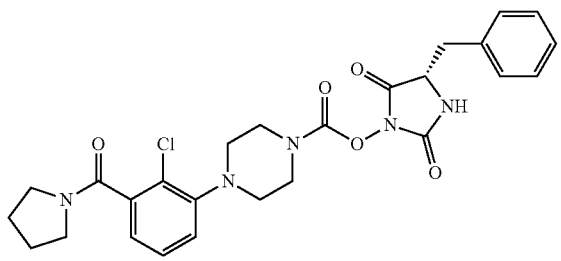 [SMILES: O=C(ON1C(=O)N[C@@H](Cc2ccccc2)C1=O)N1CCN(c2cccc(C(=O)N3CCCC3)c2Cl)CC1]

Step 1: Preparation of (S)-tert-butyl 1-(benzyloxyamino)-1-oxo-3-phenylpropan-2-ylcarbamate

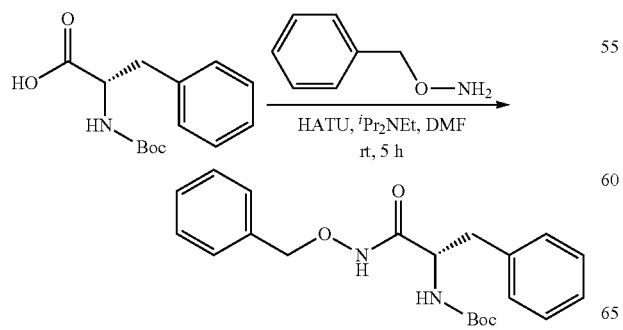

A 250-mL round-bottom flask was charged with (S)-2-(tert-butoxycarbonylamino)-3-phenylpropanoic acid (10.6 g, 42.4 mmol, 1.00 equiv), and DMF (100 mL). HATU (22.8 g, 59.9 mmol, 1.50 equiv) was added at 0° C., followed by dropwise addition of DIEA (20.6 g, 159 mmol, 4.00 equiv). The resulting solution was allowed to stir for 0.5 h at 0° C. O-Benzylhydroxylamine hydrochloride (9.54 g, 59.8 mmol, 1.50 equiv) was added, and the resulting solution was allowed to stir for 5 h at room temperature and quenched with H$_2$O (250 mL). The mixture was extracted with DCM (4×150 mL) and the organic layers were combined, washed with brine (3×100 mL), dried over anhydrous sodium sulfate, filtered and concentrated under reduced pressure. The residue was chromatographed on a silica gel column with EtOAc/petroleum ether (1/1) to provide 12.9 g (82% yield) of (S)-tert-butyl 1-(benzyloxyamino)-1-oxo-3-phenylpropan-2-ylcarbamate as a white solid.
LCMS (ESI, m/z): 371 [M+H]+.

Step 2: Preparation of (S)-2-amino-N-(benzyloxy)-3-phenylpropanamide hydrochloride

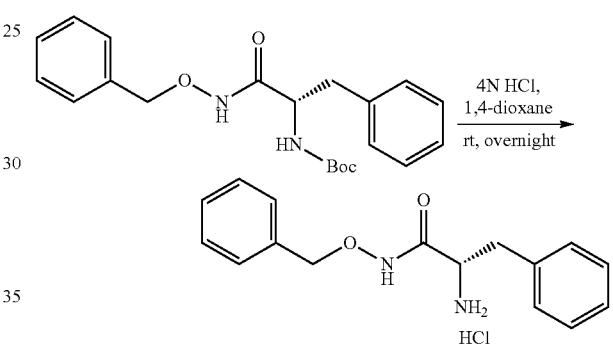

A 250-mL round-bottom flask was charged with (S)-tert-butyl 1-(benzyloxyamino)-1-oxo-3-phenylpropan-2-ylcarbamate (12.9 g, 34.8 mmol, 1.00 equiv), hydrochloric acid (4 mol/L, 5 mL), and dioxane (35 mL). The resulting solution was allowed to stir overnight at room temperature and concentrated under reduced pressure to provide 7.43 g (69% yield) of (S)-2-amino-N-(benzyloxy)-3-phenylpropanamide hydrochloride as a pink solid. LCMS (ESI, m/z): 271 [M+H]+.

Step 3: Preparation of (S)-5-benzyl-3-(benzyloxy)imidazolidine-2,4-dione

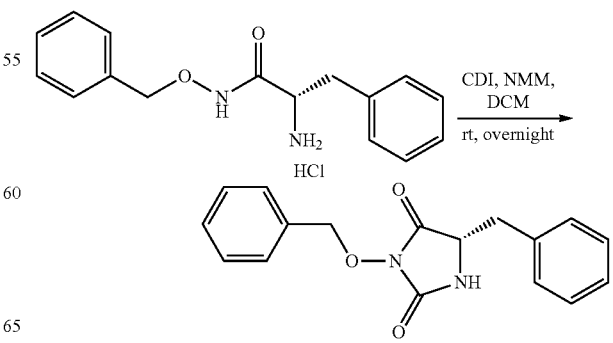

A 250-mL round-bottom flask was charged with (S)-2-amino-N-(benzyloxy)-3-phenylpropanamide hydrochloride (6.56 g, 21.4 mmol, 1.00 equiv), DCM (60 mL), and NMM (12.2 g, 121 mmol, 5.7 equiv). CDI (5.88 g, 36.3 mmol, 1.70 equiv) was added. The resulting solution was allowed to stir for 5 h at room temperature and quenched with H₂O (250 mL). The mixture was extracted with DCM (4×150 mL) and the organic layers were combined, washed with brine (3×100 mL), dried over anhydrous sodium sulfate, filtered and concentrated under reduced pressure. The residue was chromatographed on a silica gel column with EtOAc/petroleum ether (1/1) to provide 4.02 g (63% yield) of (S)-5-benzyl-3-(benzyloxy)imidazolidine-2,4-dione as a light yellow solid. LCMS (ESI, m/z): 297 [M+H]⁺.

Step 4: Preparation of (S)-5-benzyl-3-hydroxyimidazolidine-2,4-dione

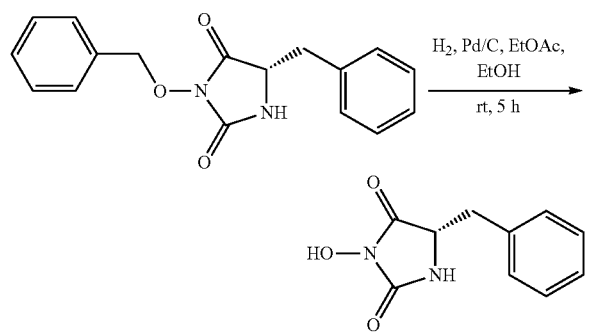

A 250-mL round-bottom flask was charged with (S)-5-benzyl-3-(benzyloxy)imidazolidine-2,4-dione (4.02 g, 13.5 mmol, 1.00 equiv), Pd/C (2 g), EtOH (60 mL), and EtOAc (15 mL). The resulting solution was maintained under a hydrogen atmosphere while stirring for 5 h at room temperature. The solids were filtered out and the resulting mixture was concentrated under reduced pressure to provide 2.17 g (78% yield) of (S)-5-benzyl-3-hydroxyimidazolidine-2,4-dione as a white solid. LCMS (ESI, m/z): 207 [M+H]⁺.

Step 5: Preparation of (S)-4-benzyl-2,5-dioxoimidazolidin-1-yl 4-(2-chloro-3-(pyrrolidine-1-carbonyl)phenyl)piperazine-1-carboxylate

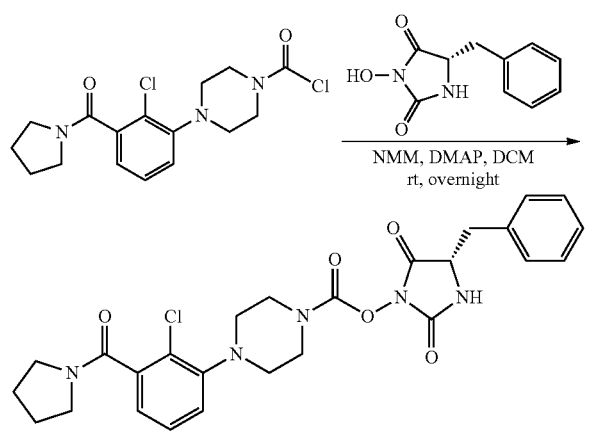

A 100-mL round-bottom flask was charged with 4-(2-chloro-3-(pyrrolidine-1-carbonyl)phenyl)piperazine-1-carbonyl chloride (Example 1, Step 9, 155 mg, 0.435 mmol, 1.00 equiv), (S)-5-benzyl-3-hydroxyimidazolidine-2,4-dione (107 mg, 0.522 mmol, 1.20 equiv), NMM (131 mg, 1.30 mmol, 3.00 equiv), DMAP (6.00 mg, 0.0511 mmol, 0.10 equiv), and DCM (5 mL). The resulting solution was allowed to stir overnight at room temperature and concentrated under reduced pressure. The crude product (260 mg) was purified by preparative HPLC to afford 30.1 mg (13% yield) of (S)-4-benzyl-2,5-dioxoimidazolidin-1-yl 4-(2-chloro-3-(pyrrolidine-1-carbonyl)phenyl)piperazine-1-carboxylate as a white solid. ¹H NMR (300 MHz, Chloroform-d) δ 7.29-7.39 (m, 4H), 7.17-7.25 (m, 2H), 7.02-7.07 (m, 2H), 5.43 (br, 1H), 4.32-4.35 (m, 1H), 3.50-3.84 (m, 6H), 3.30-3.39 (m, 1H), 3.12-3.18 (m, 6H), 2.85-3.93 (m, 1H), 1.87-2.08 (m, 4H). LCMS (ESI, m/z): 526 [M+H]⁺.

Example 8: (S)-4-benzyl-2,5-dioxoimidazolidin-1-yl 4-(2-chloro-3-(piperidine-1-carbonyl)phenyl)piperazine-1-carboxylate

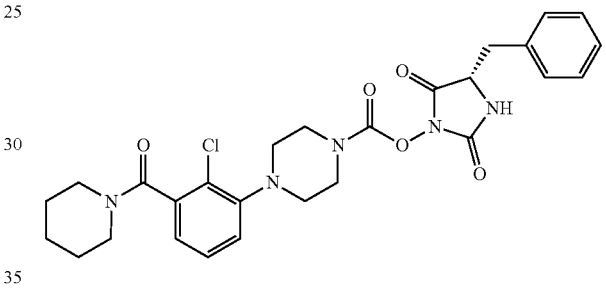

The title compound was synthesized as described in Example 7 using 4-(2-chloro-4-(piperidine-1-carbonyl)phenyl)piperazine-1-carbonyl chloride (Example 1, Steps 5-9, using piperidine in Step 6) in Step 5. Purification resulted in 22.2 mg (10% yield) of (S)-4-benzyl-2,5-dioxoimidazolidin-1-yl 4-(2-chloro-3-(piperidine-1-carbonyl)phenyl)piperazine-1-carboxylate as a white solid. ¹H NMR (300 MHz, Chloroform-d) δ 7.28-7.38 (m, 4H), 7.22-7.25 (m, 2H), 6.98-7.07 (m, 2H), 5.48 (br, 1H), 4.32-4.35 (m, 1H), 3.60-3.84 (m, 6H), 3.38-3.42 (m, 1H), 3.06-3.24 (m, 4H), 2.99-3.06 (m, 2H), 2.85-2.93 (m, 1H), 1.57-1.86 (m, 4H), 1.46 (br, 2H). LCMS (ESI, m/z): 540 [M+H]⁺.

Example 9: (S)-4-benzyl-2,5-dioxoimidazolidin-1-yl 4-(2-chloro-3-(morpholine-4-carbonyl)phenyl)piperazine-1-carboxylate

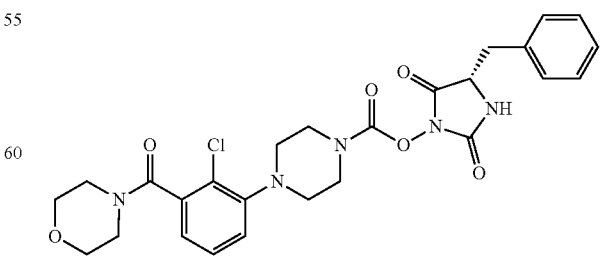

The title compound was synthesized as described in Example 7 using 4-(2-chloro-4-(morpholine-1-carbonyl)

phenyl)piperazine-1-carbonyl chloride (Example 1, Steps 5-9, using piperidine in Step 6) in Step 5. Purification resulted in 26.0 mg (12% yield) of (S)-4-benzyl-2,5-dioxoimidazolidin-1-yl 4-(2-chloro-3-(morpholine-4-carbonyl)phenyl)piperazine-1-carboxylate as a white solid. $^1$H NMR (300 MHz, Chloroform-d) δ 7.28-7.39 (m, 4H), 7.22-7.26 (m, 2H), 7.08 (d, J=6.9 Hz, 1H), 7.01 (d, J=7.5 Hz, 1H), 5.38 (br, 1H), 4.33-4.35 (m, 1H), 3.65-3.91 (m, 10H), 3.40 (m, 1H), 3.20-3.27 (m, 4H), 3.00-3.06 (m, 2H), 2.84-2.93 (m, 1H). LCMS (ESI, m/z): 542 [M+H]$^+$.

Example 10: (R)-4-benzyl-2,5-dioxoimidazolidin-1-yl 4-(2-chloro-3-(pyrrolidine-1-carbonyl)phenyl)piperazine-1-carboxylate

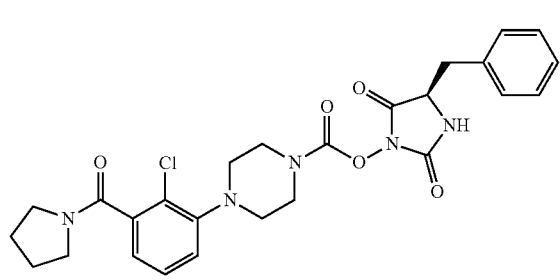 [SMILES: O=C(ON1C(=O)N[C@H](Cc2ccccc2)C1=O)N1CCN(c2cccc(C(=O)N3CCCC3)c2Cl)CC1]

The title compound was synthesized as described in Example 7 using (R)-2-(tert-butoxycarbonylamino)-3-phenylpropanoic acid in Step 1. Purification resulted in 88.2 mg (50% yield) of (R)-4-benzyl-2,5-dioxoimidazolidin-1-yl 4-(2-chloro-3-(pyrrolidine-1-carbonyl)phenyl)piperazine-1-carboxylate as a white solid. $^1$H NMR (300 MHz, Chloroform-d) δ 7.26-7.56 (m, 4H), 7.22-7.25 (m, 2H), 7.01-7.06 (m, 2H), 5.56 (br, 1H), 4.31-4.35 (m, 1H), 3.64-3.83 (m, 6H), 3.37-3.56 (m, 1H), 2.94-3.29 (m, 6H), 2.86-2.91 (m, 1H), 1.85-2.09 (m, 4H). LCMS (ESI, m/z): 526 [M+H]$^+$.

Example 11: (R)-4-benzyl-2,5-dioxoimidazolidin-1-yl 4-(2-chloro-3-(piperidine-1-carbonyl)phenyl)piperazine-1-carboxylate

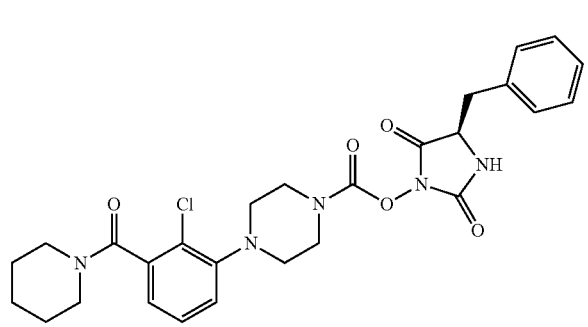 [SMILES: O=C(ON1C(=O)N[C@H](Cc2ccccc2)C1=O)N1CCN(c2cccc(C(=O)N3CCCCC3)c2Cl)CC1]

The title compound was synthesized as described in Example 8 using (R)-2-(tert-butoxycarbonylamino)-3-phenylpropanoic acid in Step 1. Purification resulted in 51.2 mg (30% yield) of (R)-4-benzyl-2,5-dioxoimidazolidin-1-yl 4-(2-chloro-3-(piperidine-1-carbonyl)phenyl)piperazine-1-carboxylate as a white solid. $^1$H NMR (300 MHz, Chloroform-d) δ 7.26-7.48 (m, 4H), 7.22-7.25 (m, 2H), 6.97-7.05 (m, 2H), 5.49 (br, 1H), 4.32-4.34 (m, 1H), 3.60-3.82 (m, 6H), 3.37-3.49 (m, 1H), 3.09-3.20 (m, 4H), 2.99-3.09 (m, 2H), 2.85-2.93 (m, 1H), 1.47-1.79 (m, 6H). LCMS (ESI, m/z): 540 [M+H]$^+$.

Example 12: (R)-4-benzyl-2,5-dioxoimidazolidin-1-yl 4-(2-chloro-3-(morpholine-4-carbonyl)phenyl)piperazine-1-carboxylate

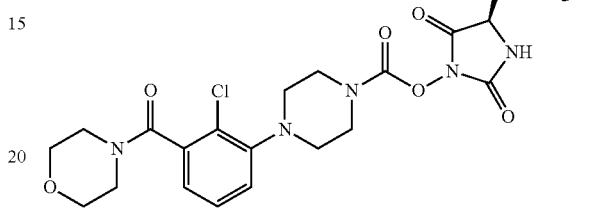

The title compound was synthesized as described in Example 9 using (R)-2-(tert-butoxycarbonylamino)-3-phenylpropanoic acid in Step 1. Purification resulted in 55.9 mg (32% yield) of (R)-4-benzyl-2,5-dioxoimidazolidin-1-yl 4-(2-chloro-3-(morpholine-4-carbonyl)phenyl)piperazine-1-carboxylate as a white solid. $^1$H NMR (300 MHz, Chloroform-d) δ 7.26-7.36 (m, 4H), 7.22-7.25 (m, 2H), 6.99-7.08 (m, 2H), 5.51 (br, 1H), 4.32-4.35 (m, 1H), 3.59-3.90 (m, 10H), 3.30-3.48 (m, 1H), 3.19-3.27 (m, 4H), 2.85-3.05 (m, 3H). LCMS (ESI, m/z): 542 [M+H]$^+$.

Example 13: (S)-4-benzyl-2,5-dioxoimidazolidin-1-yl 4-(3-(piperidine-1-carbonyl)phenyl)piperazine-1-carboxylate

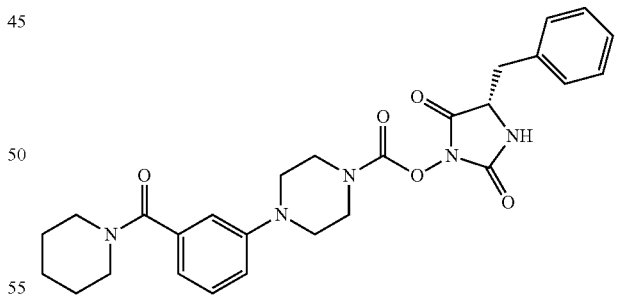

The title compound was synthesized as described in Example 8 using 4-(3-(pyrrolidine-1-carbonyl)phenyl)piperazine-1-carbonyl chloride in Step 5. Purification resulted in 68.0 mg (27% yield) of (S)-4-benzyl-2,5-dioxoimidazolidin-1-yl 4-(3-(piperidine-1-carbonyl)phenyl)piperazine-1-carboxylate as a white solid. $^1$H NMR (400 MHz, DMSO-d$_6$) δ 8.70 (s, 1H), 7.22-5.33 (m, 6H), 6.99-7.02 (m, 1H), 6.89 (br, 1H), 6.74-6.78 (m, 1H), 4.61-4.62 (m, 1H), 3.43-3.63 (m, 6H), 3.22 (br, 6H), 3.04-3.09 (m, 1H), 2.97 (br, 1H), 1.44-1.60 (m, 6H). LCMS (ESI, m/z): 506 [M+H]$^+$.

Example 14: (S)-4-benzyl-2,5-dioxoimidazolidin-1-yl 4-(2-chloro-3-(4-methylpiperazine-1-carbonyl)phenyl)piperazine-1-carboxylate

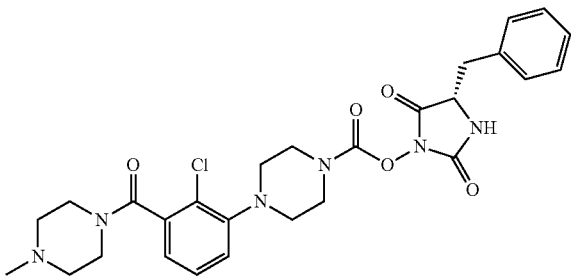 [SMILES: CN1CCN(C(=O)c2cccc(N3CCN(C(=O)ON4C(=O)N[C@@H](Cc5ccccc5)C4=O)CC3)c2Cl)CC1]

The title compound was synthesized as described in Example 7 using 4-(2-chloro-4-(1-methylpiperazine-1-carbonyl)phenyl)piperazine-1-carbonyl chloride (Example 1, Steps 5-9, using piperidine in Step 6) in Step 5. Purification resulted in 61.9 mg (22% yield) of (S)-4-benzyl-2,5-dioxoimidazolidin-1-yl 4-(2-chloro-3-(4-methylpiperazine-1-carbonyl)phenyl)piperazine-1-carboxylate as a white solid. $^1$H NMR (400 MHz, Chloroform-d) δ 7.27-7.38 (m, 4H), 7.23-7.25 (m, 2H), 7.04-7.06 (m, 1H), 6.98-7.00 (m, 1H), 5.41 (br, 1H), 4.33-4.35 (m, 1H), 3.72-4.01 (m, 6H), 3.32-3.43 (m, 1H), 3.12-3.31 (m, 4H), 2.98-3.11 (m, 2H), 2.81-2.91 (m, 1H), 2.51 (br, 2H), 2.42 (br, 1H), 2.31 (br, 4H). LCMS (ESI, m/z): 555 [M+H]$^+$.

Example 15: (S)-4-benzyl-2,5-dioxoimidazolidin-1-yl 4-(2-chloro-4-(piperidine-1-carbonyl)phenyl)piperazine-1-carboxylate

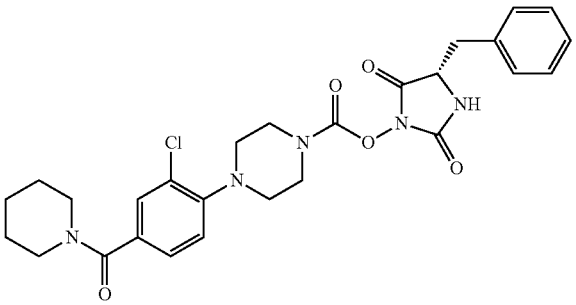 [SMILES: O=C(ON1C(=O)N[C@@H](Cc2ccccc2)C1=O)N1CCN(c2ccc(C(=O)N3CCCCC3)cc2Cl)CC1]

Step 1: Preparation of tert-butyl 4-(2-chloro-4-(ethoxycarbonyl)phenyl)piperazine-1-carboxylate

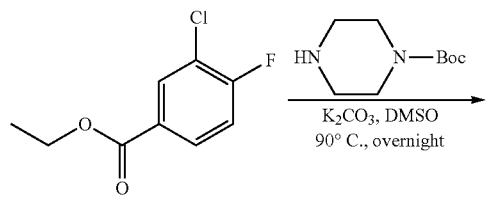

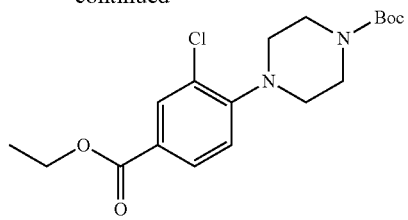

A 250-mL round-bottom flask was charged with ethyl 3-chloro-4-fluorobenzoate (2.03 g, 10.0 mmol, 1.00 equiv), potassium carbonate (4.14 g, 29.9 mmol, 3.00 equiv), DMSO (40 mL), and tert-butyl piperazine-1-carboxylate (2.23 g, 11.9 mmol, 1.20 equiv) under nitrogen. The resulting solution was allowed to stir overnight at 90° C. and quenched with water (20 mL). The mixture was extracted with EtOAc (3×30 mL) and the organic layers were combined, washed with brine (3×30 mL), dried over anhydrous sodium sulfate, filtered and concentrated under reduced pressure. The residue was chromatographed on a silica gel column with EtOAc/petroleum ether (1/2) to provide 2.21 g (60% yield) of tert-butyl 4-(2-chloro-4-(ethoxycarbonyl)phenyl)piperazine-1-carboxylate as a white solid. LCMS (ESI, m/z): 369 [M+H]$^+$.

Step 2: Preparation of 4-(4-(tert-butoxycarbonyl)piperazin-1-yl)-3-chlorobenzoic acid

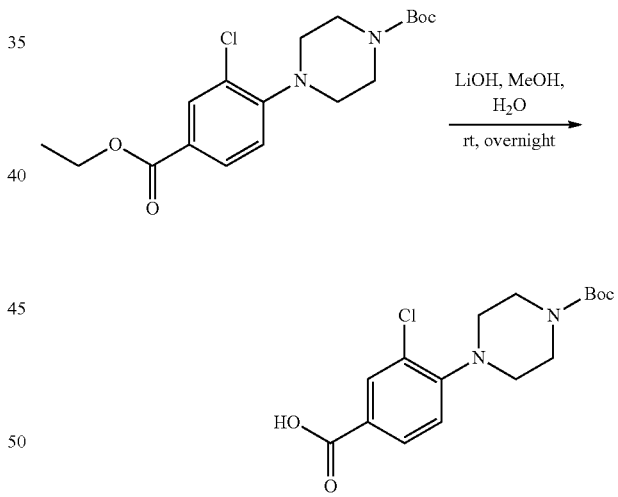

A 250-mL round-bottom flask was charged with tert-butyl 4-(2-chloro-4-(ethoxycarbonyl)phenyl)piperazine-1-carboxylate (2.21 g, 5.99 mmol, 1.00 equiv), MeOH (10 mL), water (10 mL), and lithium hydroxide (1.26 g, 53.9 mmol, 9.00 equiv). The resulting solution was allowed to stir overnight at room temperature. The pH of the solution was adjusted to 5 with hydrochloric acid (1M, 5 mL). The mixture was extracted with DCM (3×30 mL) and the organic layers were combined, washed with brine (3×30 mL), dried over anhydrous sodium sulfate, filtered and concentrated under reduced pressure to provide 2.03 g (99% yield) of 4-(4-(tert-butoxycarbonyl)piperazin-1-yl)-3-chlorobenzoic acid as a white solid. LCMS (ESI, m/z): 341 [M+H]$^+$.

Step 3: Preparation of tert-butyl 4-(2-chloro-4-(chlorocarbonyl)phenyl)piperazine-1-carboxylate

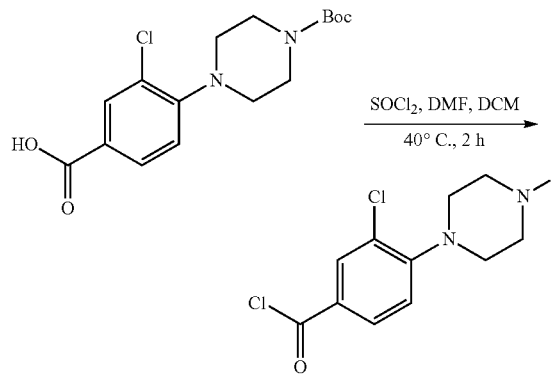

A 100-mL round-bottom flask was charged with 4-(4-(tert-butoxycarbonyl)piperazin-1-yl)-3-chlorobenzoic acid (682 mg, 2.00 mmol, 1.00 equiv), DCM (10 mL), and DMF (0.1 mL). The resulting solution was allowed to stir for 1 h at room temperature. Thionyl chloride (472 mg, 4.00 mmol, 2.00 equiv) was added. The resulting solution was allowed to stir for 2 h at 40° C. and concentrated under reduced pressure to provide 718 mg (crude) of tert-butyl 4-(2-chloro-4-(chlorocarbonyl)phenyl)piperazine-1-carboxylate as a yellow oil.

Step 4: Preparation of tert-butyl 4-(2-chloro-4-(piperidine-1-carbonyl)phenyl)piperazine-1-carboxylate

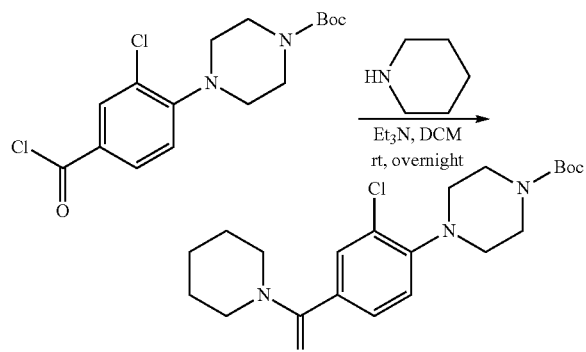

A 100-mL round-bottom flask was charged with tert-butyl 4-(2-chloro-4-(chlorocarbonyl)phenyl)piperazine-1-carboxylate (718 mg, 2.00 mmol, 1.00 equiv), DCM (5 mL), piperidine (340 mg, 3.99 mmol, 2.00 equiv), and TEA (606 mg, 5.99 mmol, 3.00 equiv). The resulting solution was allowed to stir overnight at room temperature and quenched with water (20 mL). The mixture was extracted with DCM (3×30 mL) and the organic layers were combined, washed with brine (3×30 mL), dried over anhydrous sodium sulfate, filtered and concentrated under reduced pressure. The residue was chromatographed on a silica gel column with EtOAc/petroleum ether (1/4) to provide 442 mg (54% yield) of tert-butyl 4-(2-chloro-4-(piperidine-1-carbonyl)phenyl)piperazine-1-carboxylate as a colorless oil. LCMS (ESI, m/z): 408 [M+H]$^+$.

Step 5: Preparation of (3-chloro-4-(piperazin-1-yl)phenyl)(piperidin-1-yl)methanone

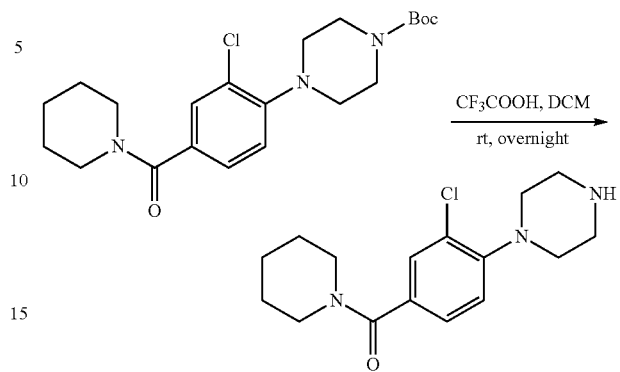

A 50-mL round-bottom flask was charged with tert-butyl 4-(2-chloro-4-(piperidine-1-carbonyl)phenyl)piperazine-1-carboxylate (442 mg, 1.08 mmol, 1.00 equiv), DCM (5 mL), and TFA (2 mL). The resulting solution was allowed to stir overnight at room temperature and concentrated under reduced pressure. The crude product was dissolved in 1M NaOH solution (10 mL) and extracted with DCM (3×20 mL). The organic layers were combined, washed with brine (10 mL), dried over anhydrous sodium sulfate, filtered and concentrated under reduced pressure to provide 332 mg (99% yield) of (3-chloro-4-(piperazin-1-yl)phenyl)(piperidin-1-yl)methanone as a light yellow oil. LCMS (ESI, m z): 308 [M+H]$^+$.

Step 6: Preparation of 4-(2-chloro-4-(piperidine-1-carbonyl)phenyl)piperazine-1-carbonyl chloride

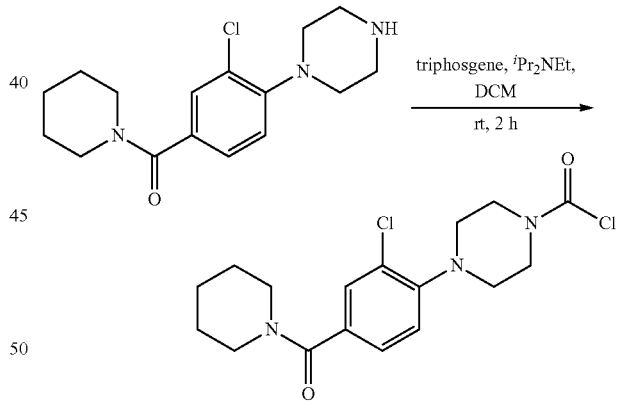

A 40-mL round-bottom flask was charged with triphosgene (127 mg, 0.431 mmol, 0.40 equiv), DCM (5 mL), and (3-chloro-4-(piperazin-1-yl)phenyl)(piperidin-1-yl)methanone (332 mg, 1.08 mmol, 1.00 equiv). DIPEA (414 mg, 3.20 mmol, 3.00 equiv) was added at 0° C. The resulting solution was allowed to stir for 2 h at room temperature and quenched with water (20 mL). The mixture was extracted with DCM (3×30 mL) and the organic layers were combined, washed with brine (3×30 mL), dried over anhydrous sodium sulfate, filtered and concentrated under reduced pressure to provide 396 mg (99% yield) of 4-(2-chloro-4-(piperidine-1-carbonyl)phenyl)piperazine-1-carbonyl chloride as a yellow oil. LCMS (ESI, m/z): 370 [M+H]$^+$.

Step 7: Preparation of (S)-4-benzyl-2,5-dioxoimidazolidin-1-yl 4-(2-chloro-4-(piperidine-1-carbonyl)phenyl)piperazine-1-carboxylate

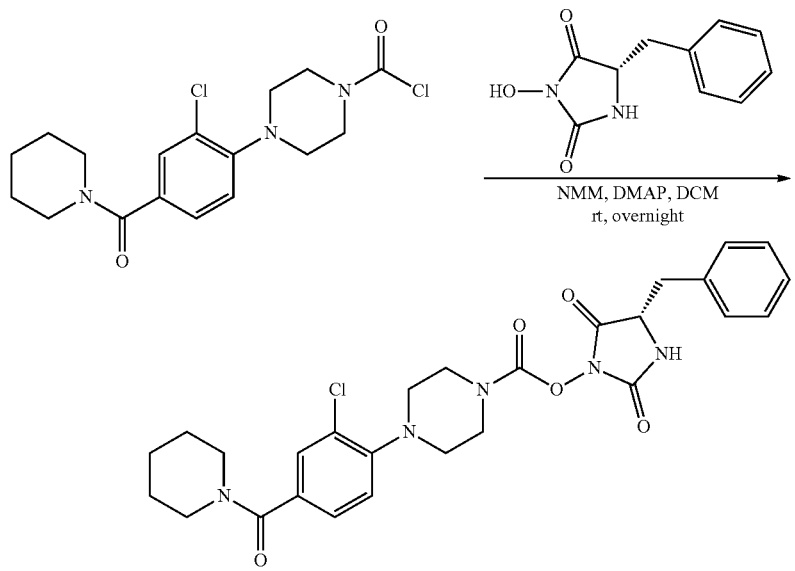

A 40-mL round-bottom flask was charged with (S)-5-benzyl-3-hydroxyimidazolidine-2,4-dione (prepared as described in Example 7, Steps 1-4; 243 mg, 1.18 mmol, 1.10 equiv), 4-[2-chloro-4-[(piperidin-1-yl)carbonyl]phenyl]piperazine-1-carbonyl chloride (396 mg, 1.07 mmol, 1.00 equiv), NMM (324 mg, 3.20 mmol, 3.00 equiv), DMAP (13.0 mg, 0.110 mmol, 0.10 equiv), and DCM (5 mL). The resulting solution was allowed to stir overnight at room temperature and quenched with water (20 mL). The mixture was extracted with DCM (3×30 mL) and the organic layers were combined, washed with brine (3×30 mL), dried over anhydrous sodium sulfate, filtered and concentrated under reduced pressure. The crude product (169 mg) was purified by preparative HPLC to afford 145.8 mg (25% yield) of (S)-4-benzyl-2,5-dioxoimidazolidin-1-yl 4-(2-chloro-4-(piperidine-1-carbonyl)phenyl)piperazine-1-carboxylate as a white solid. $^1$H NMR (400 MHz, Chloroform-d) δ 7.52 (s, 1H), 7.27-7.44 (m, 4H), 7.22-7.25 (m, 2H), 7.00-7.05 (m, 1H), 5.46 (br, 1H), 4.32-4.35 (m, 1H), 3.25-3.84 (m, 9H), 3.14 (br, 4H), 2.86-2.92 (m, 1H), 1.48-1.79 (m, 6H). LCMS (ESI, m/z): 540 [M+H]$^+$.

Example 16: (S)-4-benzyl-2,5-dioxoimidazolidin-1-yl 4-(2-chloro-3-(dimethylcarbamoyl)phenyl)piperazine-1-carboxylate The title compound was synthesized as described in Example 7 using 4-(2-chloro-4-(dimethylamine-1-carbonyl)phenyl)piperazine-1-carbonyl chloride (Example 1, Steps 5-9, using piperidine in Step 6) in Step 5. Purification resulted in 57.5 mg (23% yield) of (S)-4-benzyl-2,5-dioxoimidazolidin-1-yl 4-(2-chloro-3-(dimethylcarbamoyl)phenyl)piperazine-1-carboxylate as a white solid. $^1$H NMR (400 MHz, Chloroform-d) δ 7.36-7.39 (m, 2H), 7.29-7.34 (m, 2H), 7.23-7.26 (m, 2H), 6.99-7.06 (m, 2H), 5.33 (br, 1H), 4.32-4.35 (m, 1H), 3.73-4.84 (m, 4H), 3.40-3.43 (m, 1H), 3.14-3.19 (m, 5H), 3.01-3.04 (m, 2H), 2.85-2.91 (m, 4H). LCMS (ESI, m/z): 500 [M+H]$^+$.

Example 17: (S)-4-benzyl-2,5-dioxoimidazolidin-1-yl 4-(2-chloro-5-(piperidine-1-carbonyl)phenyl)piperazine-1-carboxylate

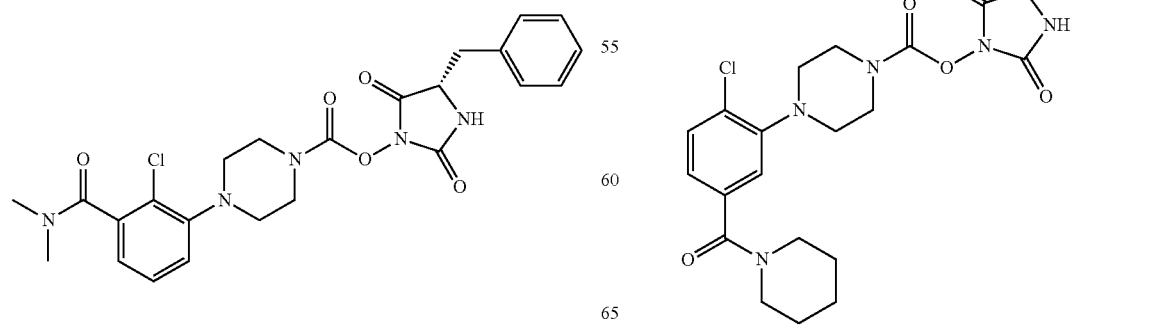

Step 1: Preparation of 3-bromo-4-chlorobenzoyl chloride

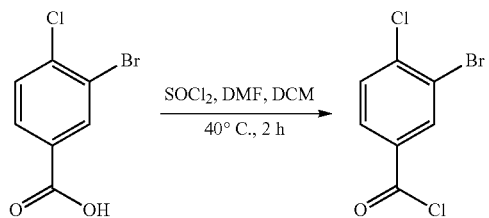

A 250-mL round-bottom flask was charged with 3-bromo-4-chlorobenzoic acid (2.35 g, 9.98 mmol, 1.00 equiv), DCM (40 mL), and DMF (1 mL). The resulting solution was allowed to stir for 1 h at room temperature. Thionyl chloride (2.36 g, 20.0 mmol, 2.00 equiv) was added. The resulting solution was allowed to stir for 2 h at 40° C. and concentrated under reduced pressure to provide 3.50 g (crude) of 3-bromo-4-chlorobenzoyl chloride as a light yellow oil.

Step 2: Preparation of (3-bromo-4-chlorophenyl)(piperidin-1-yl)methanone

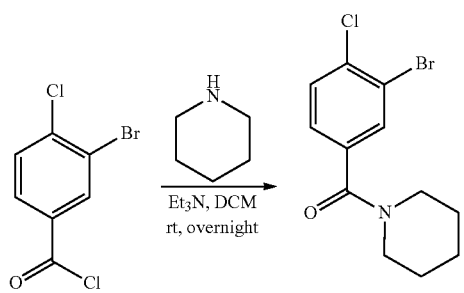

A 250-mL round-bottom flask was charged with 3-bromo-4-chlorobenzoyl chloride (2.54 g, 10.0 mmol, 1.00 equiv), DCM (40 mL), piperidine (1.70 g, 19.9 mmol, 2.00 equiv), and TEA (3.03 g, 29.9 mmol, 3.00 equiv). The resulting solution was allowed to stir overnight at room temperature and quenched with water (20 mL). The mixture was extracted with DCM (3×30 mL) and the organic layers were combined, washed with brine (3×30 mL), dried over anhydrous sodium sulfate, filtered and concentrated under reduced pressure. The residue was chromatographed on a silica gel column with EtOAc/petroleum ether (1/5) to provide 2.27 g (75% yield) of (3-bromo-4-chlorophenyl)(piperidin-1-yl)methanone as a light yellow oil. LCMS (ESI, m/z): 302 [M+H]$^+$.

Step 3: Preparation of tert-butyl 4-(2-chloro-5-(piperidine-1-carbonyl)phenyl)piperazine-1-carboxylate

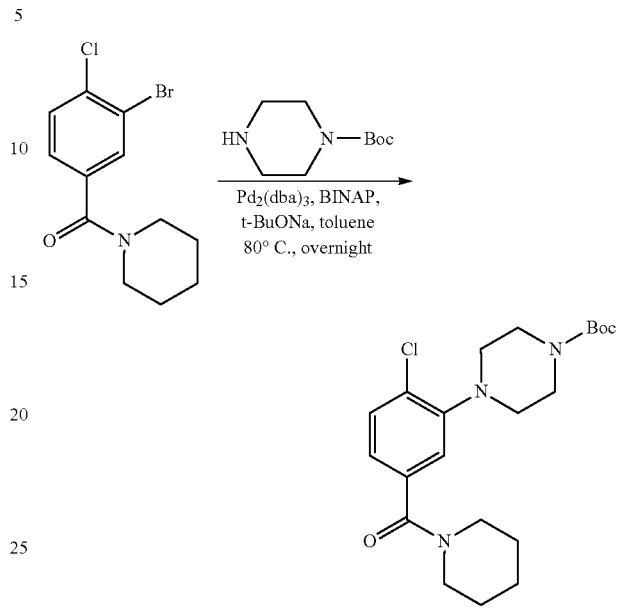

A 40-mL round-bottom flask was charged with tert-butyl piperazine-1-carboxylate (558 mg, 3.00 mmol, 1.50 equiv), (3-bromo-4-chlorophenyl)(piperidin-1-yl)methanone (606 mg, 2.00 mmol, 1.00 equiv), tris(dibenzylideneacetone)dipalladium (91.5 mg, 0.100 mmol, 0.05 equiv), 2,2'-bis(diphenylphosphino)-1,1'-binaphthyl (187 mg, 0.300 mmol, 0.15 equiv), sodium tert-butoxide (288 mg, 3.00 mmol, 1.50 equiv), and toluene (15 mL) under nitrogen. The resulting solution was allowed to stir overnight at 80° C. and quenched with water (20 mL). The mixture was extracted with EtOAc (3×30 mL) and the organic layers were combined, washed with brine (3×30 mL), dried over anhydrous sodium sulfate, filtered and concentrated under reduced pressure. The residue was chromatographed on a silica gel column with EtOAc/petroleum ether (1/1) to provide 722 mg (91% yield) of tert-butyl 4-(2-chloro-5-(piperidine-1-carbonyl)phenyl)piperazine-1-carboxylate as a yellow oil. LCMS (ESI, m/z): 408 [M+H]$^+$.

Step 4: Preparation of (4-chloro-3-(piperazin-1-yl)phenyl)(piperidin-1-yl)methanone

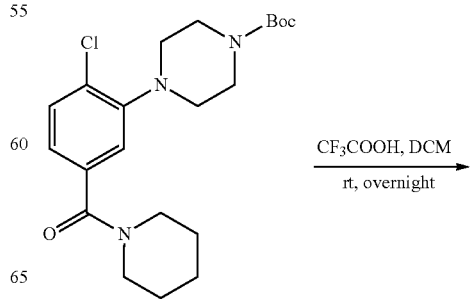

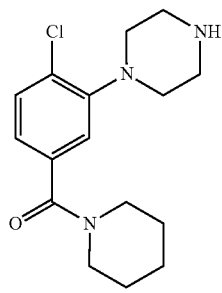

A 100-mL round-bottom flask was charged with tert-butyl 4-(2-chloro-5-(piperidine-1-carbonyl)phenyl)piperazine-1-carboxylate (722 mg, 1.77 mmol, 1.00 equiv), DCM (25 mL), and TFA (5 mL). The resulting solution was allowed to stir overnight at room temperature and concentrated under reduced pressure to provide 532 mg (98% yield) of (4-chloro-3-(piperazin-1-yl)phenyl)(piperidin-1-yl)methanone as a yellow oil. LCMS (ESI, m/z): 308 [M+H]+.

Step 5: Preparation of 4-(2-chloro-5-(piperidine-1-carbonyl)phenyl)piperazine-1-carbonyl chloride

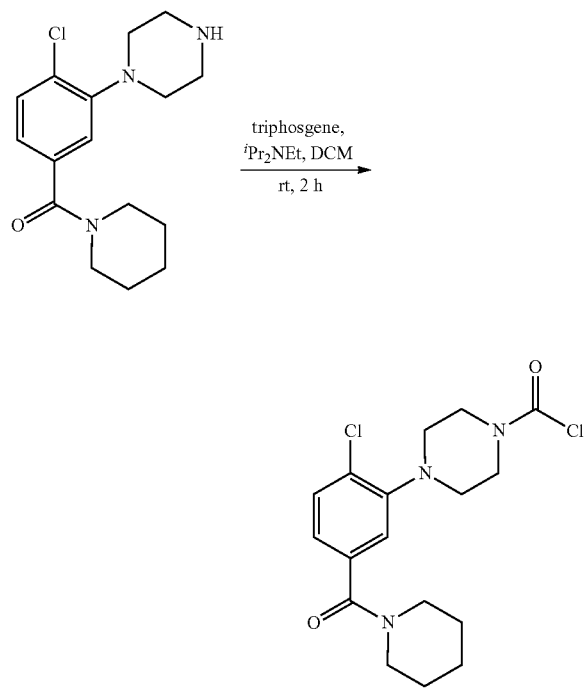

A 40-mL round-bottom flask was charged with triphosgene (59.4 mg, 0.201 mmol, 0.40 equiv), DCM (5 mL), and (4-chloro-3-(piperazin-1-yl)phenyl)(piperidin-1-yl)methanone (154 mg, 0.501 mmol, 1.00 equiv). DIPEA (194 mg, 1.50 mmol, 3.00 equiv) was added at 0° C. The resulting solution was allowed to stir for 2 h at room temperature and quenched with water (20 mL). The mixture was extracted with DCM (3×30 mL) and the organic layers were combined, washed with brine (3×30 mL), dried over anhydrous sodium sulfate, filtered and concentrated under reduced pressure to provide 250 mg (crude) of 4-(2-chloro-5-(piperidine-1-carbonyl)phenyl)piperazine-1-carbonyl chloride as a yellow oil. LCMS (ESI, m/z): 370 [M+H]+.

Step 6: Preparation of (S)-4-benzyl-2,5-dioxoimidazolidin-1-yl 4-(2-chloro-5-(piperidine-1-carbonyl)phenyl)piperazine-1-carboxylate

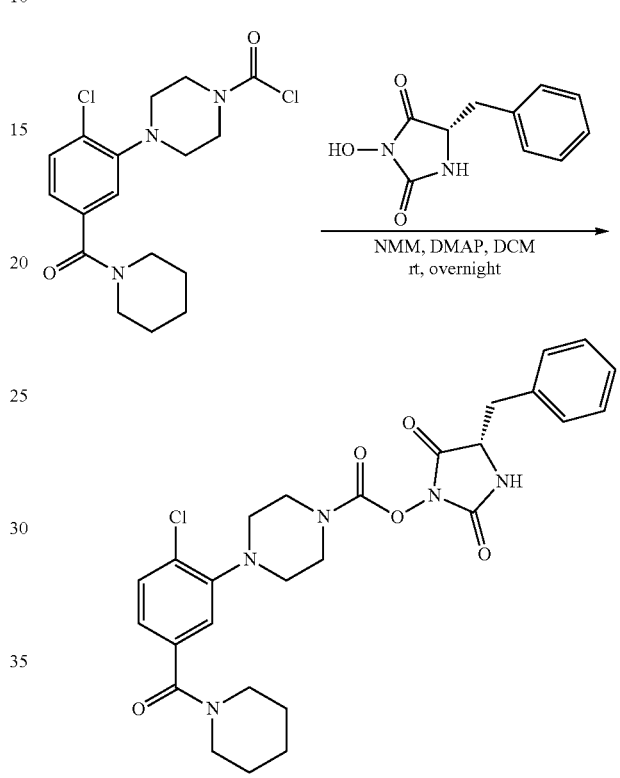

A 40-mL round-bottom flask was charged with 4-(2-chloro-5-(piperidine-1-carbonyl)phenyl)piperazine-1-carbonyl chloride (185 mg, 0.501 mmol, 1.00 equiv), DMAP (6.00 mg, 0.050 mmol, 0.10 equiv), DCM (10 mL), (S)-5-benzyl-3-hydroxyimidazolidine-2,4-dione (prepared as described in Example 7, Steps 1-4; 124 mg, 0.601 mmol, 1.20 equiv), and NMM (151 mg, 1.49 mmol, 3.00 equiv). The resulting solution was allowed to stir overnight at room temperature and quenched with water (20 mL). The mixture was extracted with DCM (3×30 mL) and the organic layers were combined, washed with brine (3×30 mL), dried over anhydrous sodium sulfate, filtered and concentrated under reduced pressure. The crude product (196 mg) was purified by preparative HPLC to afford 57.8 mg (21% yield) of (S)-4-benzyl-2,5-dioxoimidazolidin-1-yl 4-(2-chloro-5-(piperidine-1-carbonyl)phenyl)piperazine-1-carboxylate as a white solid. $^1$H NMR (400 MHz, Chloroform-d) δ 7.52-7.53 (m, 1H), 7.27-7.40 (m, 3H), 7.13-7.23 (m, 2H), 7.08 (s, 1H), 7.00-7.07 (m, 1H), 5.31-5.91 (m, 1H), 4.32-4.34 (m, 1H), 3.53-3.94 (m, 6H), 3.27-3.49 (m, 3H), 3.17 (br, 4H), 2.86-2.91 (m, 1H), 1.52-1.82 (m, 6H). LCMS (ESI, m/z): 540 [M+H]+.

Example 18: (S)-4-benzyl-2,5-dioxoimidazolidin-1-yl 4-(3-carbamoyl-2-chlorophenyl)piperazine-1-carboxylate

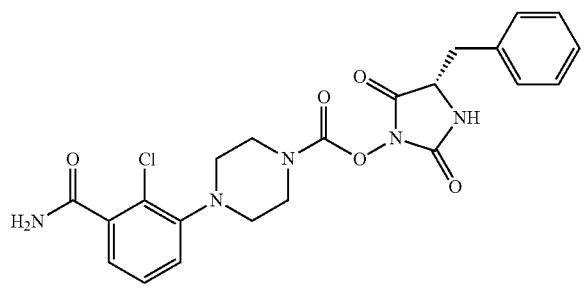 [SMILES: NC(=O)c1cccc(N2CCN(C(=O)ON3C(=O)N[C@@H](Cc4ccccc4)C3=O)CC2)c1Cl]

Step 1: Preparation of methyl 3-bromo-2-chlorobenzoate

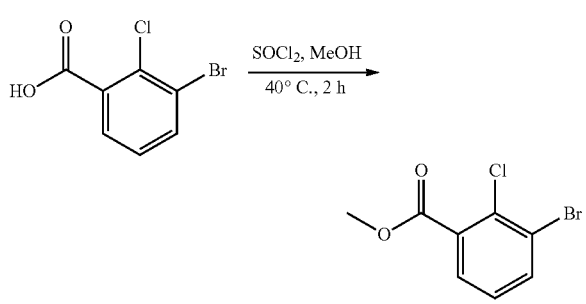

A 250-mL round-bottom flask was placed 3-bromo-2-chlorobenzoic acid (4.70 g, 19.9 mmol, 1.00 equiv), MeOH (80 mL), and thionyl chloride (4.72 g, 40.0 mmol, 2.00 equiv). The resulting solution was allowed to stir for 2 h at 40° C. and quenched with water (20 mL). The mixture was extracted with DCM (3×30 mL) and the organic layers were combined, washed with brine (3×30 mL), dried over anhydrous sodium sulfate, filtered and concentrated under reduced pressure to provide 3.01 g (60% yield) of methyl 3-bromo-2-chlorobenzoate as a light yellow oil. LCMS (ESI, m/z): 249 [M+H]$^+$.

Step 2: Preparation of tert-butyl 4-(2-chloro-3-(methoxycarbonyl)phenyl)piperazine-1-carboxylate

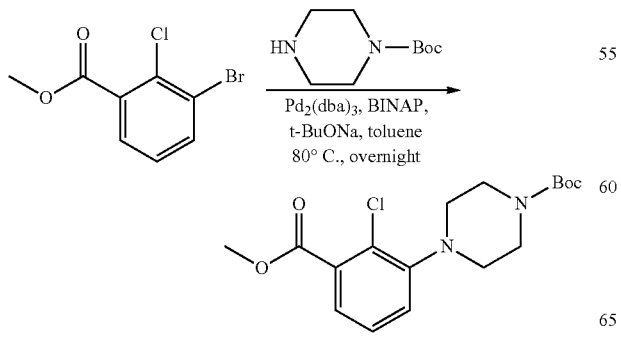

A 40-mL round-bottom flask was charged with methyl 3-bromo-2-chlorobenzoate (498 mg, 2.00 mmol, 1.00 equiv), tert-butyl piperazine-1-carboxylate (558 mg, 3.00 mmol, 1.50 equiv), tris(dibenzylideneacetone)dipalladium (103 mg, 0.101 mmol, 0.05 equiv), tert-butyl piperazine-1-carboxylate (187 mg, 1.95 mmol, 1.50 equiv), 2,2'-bis(diphenylphosphino)-1,1'-binaphthyl (187 mg, 0.301 mmol, 0.15 equiv), and toluene (5 mL). The resulting solution was allowed to stir overnight at 80° C. and quenched with water (20 mL). The mixture was extracted with EtOAc (3×30 mL) and the organic layers were combined, washed with brine (3×30 mL), dried over anhydrous sodium sulfate, filtered and concentrated under reduced pressure. The residue was chromatographed on a silica gel column with EtOAc/petroleum ether (9/1) to provide 100 mg (14% yield) of tert-butyl 4-(2-chloro-3-(methoxycarbonyl)phenyl)piperazine-1-carboxylate as a yellow solid. LCMS (ESI, m/z): 355 [M+H]$^+$.

Step 3: Preparation of 3-(4-(tert-butoxycarbonyl)piperazin-1-yl)-2-chlorobenzoic acid

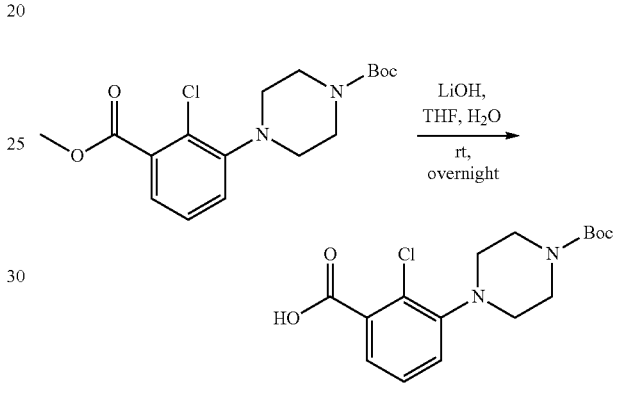

A 100-mL round-bottom flask was charged with tert-butyl 4-(2-chloro-3-(methoxycarbonyl)phenyl)piperazine-1-carboxylate (1.00 g, 2.82 mmol, 1.00 equiv), lithium hydroxide (135 mg, 5.64 mmol, 2.00 equiv), THF (8 mL), and water (4 mL). The resulting solution was allowed to stir overnight at room temperature. The pH of the solution was adjusted to 5 with hydrochloric acid (1 mol/L). The mixture was extracted with DCM (3×30 mL) and the organic layers were combined, washed with brine (3×30 mL), dried over anhydrous sodium sulfate, filtered and concentrated under reduced pressure to provide 600 mg (62% yield) of 3-(4-(tert-butoxycarbonyl)piperazin-1-yl)-2-chlorobenzoic acid as a white solid. LCMS (ESI, m/z): 341 [M+H]$^+$.

Step 4: Preparation of tert-butyl 4-(3-carbamoyl-2-chlorophenyl)piperazine-1-carboxylate

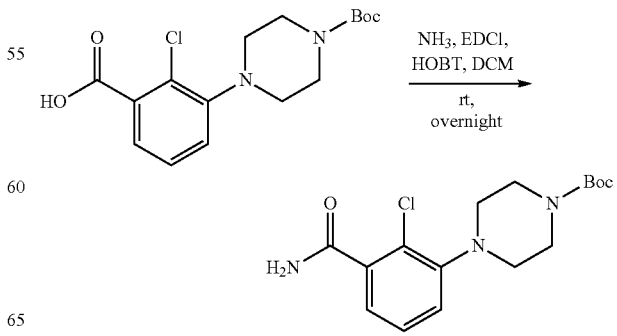

An 8-mL round-bottom flask was charged with 3-(4-(tert-butoxycarbonyl)piperazin-1-yl)-2-chlorobenzoic acid (50.0 mg, 0.151 mmol, 1.00 equiv), N-(3-dimethylaminopropyl)-N'-ethylcarbodiimide hydrochloride (37.5 mg, 0.196 mmol, 1.30 equiv), 1-Hydroxybenzotrizole (25.5 mg, 0.196 mmol, 1.30 equiv), and DCM (2 mL). The resulting solution was allowed to stir for 1 h at room temperature. Ammonia (in DCM, 2 mL) was added at 0° C. The resulting solution was allowed to stir overnight at room temperature quenched with water (20 mL). The mixture was extracted with DCM (3×30 mL) and the organic layers were combined, washed with brine (3×30 mL), dried over anhydrous sodium sulfate, filtered and concentrated under reduced pressure. The residue was chromatographed on a silica gel column with DCM/MeOH (7/93) to provide 30.3 mg (60% yield) of tert-butyl 4-(3-carbamoyl-2-chlorophenyl)piperazine-1-carboxylate as a white solid. LCMS (ESI, m/z): 340 [M+H]$^+$.

Step 5: Preparation of
2-chloro-3-(piperazin-1-yl)benzamide hydrochloride

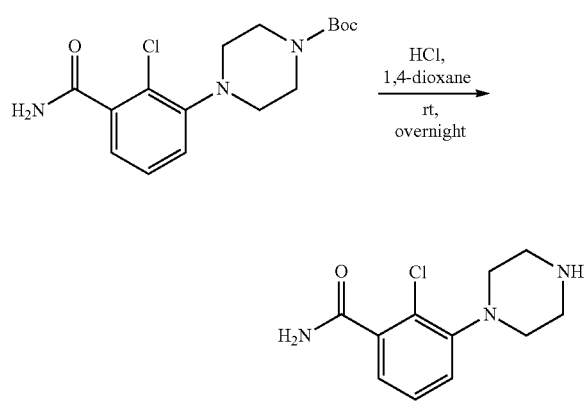

A 100-mL round-bottom flask was charged with tert-butyl 4-(3-carbamoyl-2-chlorophenyl)piperazine-1-carboxylate (340 mg, 1.00 mmol, 1.00 equiv), 1,4-dioxane (14 mL), and hydrogen chloride (2 mL). The resulting solution was allowed to stir overnight at room temperature and concentrated under reduced pressure to provide 239 mg (86% yield) of 2-chloro-3-(piperazin-1-yl)benzamide hydrochloride as a yellow oil. LCMS (ESI, m/z): 240 [M+H]$^+$.

Step 6: Preparation of (S)-4-benzyl-2,5-dioxoimidazolidin-1-yl 4-(3-carbamoyl-2-chlorophenyl)piperazine-1-carboxylate

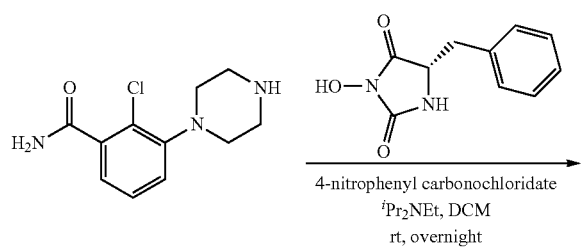

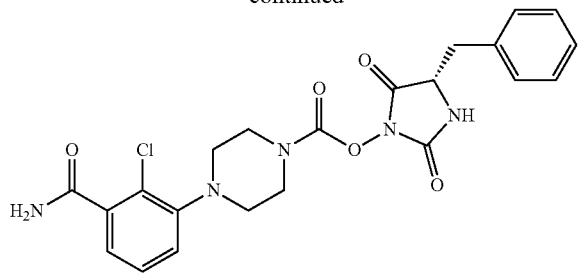

A 40-mL round-bottom flask was charged with (S)-5-benzyl-3-hydroxyimidazolidine-2,4-dione (prepared as described in Example 7, Steps 1-4; 227 mg, 1.10 mmol, 1.10 equiv), 4-nitrophenyl carbonochloridate (222 mg, 1.10 mmol, 1.10 equiv), and DCM (5 mL). DIPEA (387 mg, 3.00 mmol, 3.00 equiv) was added at 0° C. The resulting solution was allowed to stir for 2 h at 0° C. 2-Chloro-3-(piperazin-1-yl)benzamide hydrochloride (276 mg, 1.00 mmol, 1.00 equiv) was added. The resulting solution was allowed to stir overnight at room temperature and quenched with water (20 mL). The mixture was extracted with DCM (3×30 mL) and the organic layers were combined, washed with brine (3×30 mL), dried over anhydrous sodium sulfate, filtered and concentrated under reduced pressure. The crude product (269 mg) was purified by preparative HPLC to afford 106.0 mg (22% yield) of (S)-4-benzyl-2,5-dioxoimidazolidin-1-yl 4-(3-carbamoyl-2-chlorophenyl)piperazine-1-carboxylate as a white solid. $^1$H NMR (400 MHz, MeOH-d$_4$) δ 7.18-7.39 (m, 8H), 5.02-5.05 (m, 1H), 3.60 (br, 2H), 3.45 (br, 2H), 3.17-3.28 (m, 2H), 3.11 (br, 2H), 2.97 (br, 2H). LCMS (ESI, m/z): 472 [M+H]$^+$.

Example 19: (S)-3-(4-((4-benzyl-2,5-dioxoimidazolidin-1-yloxy)carbonyl)piperazin-1-yl)-2-chlorobenzoic acid

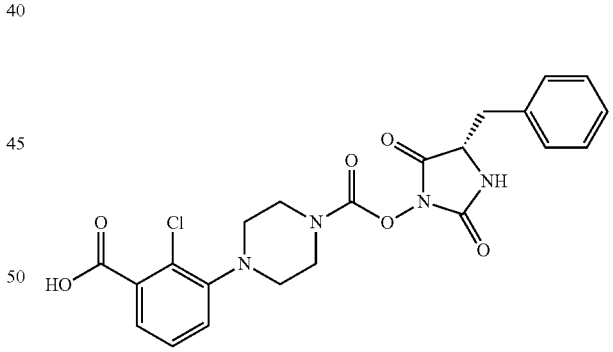

Step 1: Preparation of
2-chloro-3-(piperazin-1-yl)benzoic acid

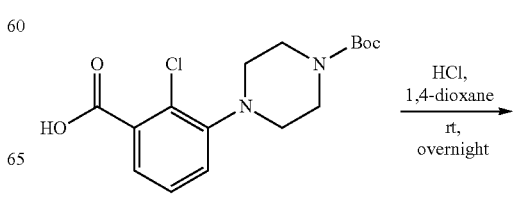

-continued

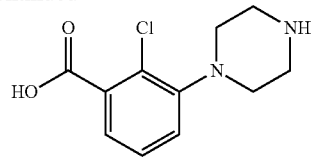

A 100-mL round-bottom flask was charged with 3-(4-(tert-butoxycarbonyl)piperazin-1-yl)-2-chlorobenzoic acid (135 mg, 0.392 mmol, 1.00 equiv), 1,4-dioxane (5 mL), and hydrochloric acid (1 mL). The resulting solution was allowed to stir overnight at room temperature and concentrated under reduced pressure to provide 120 mg (crude) of 2-chloro-3-(piperazin-1-yl)benzoic acid as a yellow oil. LCMS (ESI, m/z): 241 [M+H]+.

Step 2: Preparation of (S)-3-(4-((4-benzyl-2,5-dioxoimidazolidin-1-yloxy)carbonyl)piperazin-1-yl)-2-chlorobenzoic acid

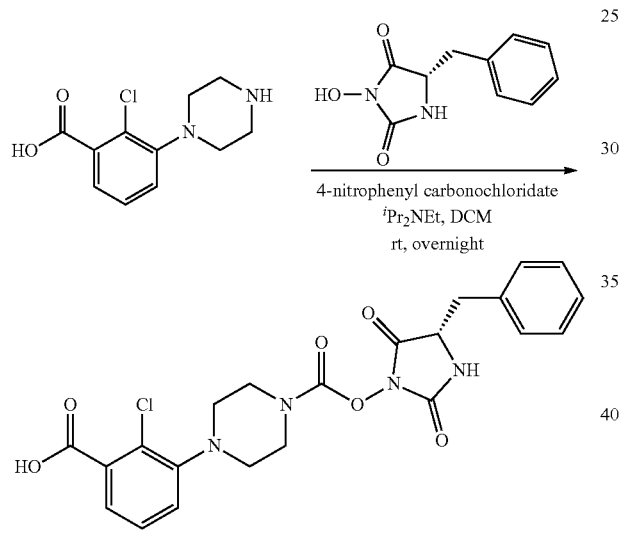

A 40-mL round-bottom flask was charged with 4-nitrophenyl chloroformate (89.0 mg, 0.441 mmol, 1.10 equiv), DCM (5 mL), and (S)-5-benzyl-3-hydroxyimidazolidine-2,4-dione (prepared as described in Example 7, Steps 1-4; 90.3 mg, 0.441 mmol, 1.10 equiv). DIPEA (155 mg, 1.20 mmol, 3.00 equiv) was added at 0° C. The resulting solution was allowed to stir for 2 h at room temperature. 2-Chloro-3-(piperazin-1-yl)benzoic acid (96.3 mg, 0.401 mmol, 1.00 equiv). The resulting solution was allowed to stir overnight at room temperature and quenched with water (20 mL). The mixture was extracted with DCM (3×30 mL) and the organic layers were combined, washed with brine (3×30 mL), dried over anhydrous sodium sulfate, filtered and concentrated under reduced pressure. The crude product (102 mg) was purified by preparative HPLC to afford 11.5 mg (6% yield) of (S)-3-(4-((4-benzyl-2,5-dioxoimidazolidin-1-yloxy)carbonyl)piperazin-1-yl)-2-chlorobenzoic acid as a white solid. 1H NMR (400 MHz, MeOH-d4) δ 7.25-7.34 (m, 4H), 7.15-7.19 (m, 3H), 7.00-7.09 (m, 1H), 5.07-5.09 (m, 1H), 3.60 (br, 4H), 3.20-3.30 (m, 2H), 3.15 (br, 2H), 3.95 (br, 2H). LCMS (ESI, m/z): 473 [M+H]+.

Example 20: (S)-4-benzyl-3-methyl-2,5-dioxoimidazolidin-1-yl 4-(2-chloro-3-(piperidine-1-carbonyl)phenyl)piperazine-1-carboxylate

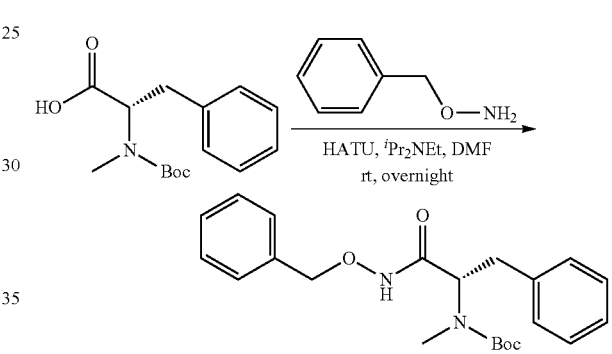

Step 1: Preparation of (S)-tert-butyl 1-(benzyloxyamino)-1-oxo-3-phenylpropan-2-yl(methyl)carbamate

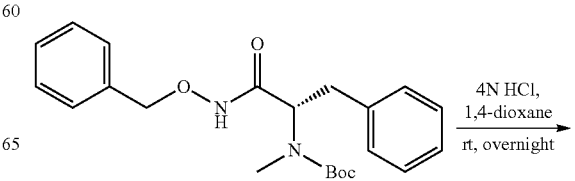

A 500-mL round-bottom flask was charged with (S)-2-(tert-butoxycarbonyl(methyl)amino)-3-phenylpropanoic acid (5.58 g, 19.9 mmol, 1.00 equiv), HATU (11.4 g, 29.9 mmol, 1.50 equiv), DIPEA (7.74 g, 60.0 mmol, 3.00 equiv), and DMF (300 mL). The resulting solution was allowed to stir for 2 h at room temperature. O-Benzylhydroxylamine (2.46 g, 19.9 mmol, 1.00 equiv) was added, and the reaction mixture was allowed to stir overnight at room temperature and quenched with water (100 mL). The mixture was extracted with EtOAc (3×200 mL) and the organic layers were combined, washed with brine (3×200 mL), dried over anhydrous sodium sulfate, filtered and concentrated under reduced pressure. The residue was chromatographed on a silica gel column with EtOAc/petroleum ether (5/1) to provide 5.34 g (70% yield) of (S)-tert-butyl 1-(benzyloxyamino)-1-oxo-3-phenylpropan-2-yl(methyl)carbamate as a yellow oil. LCMS (ESI, m/z): 385 [M+H]+.

Step 2: Preparation of (S)—N-(benzyloxy)-2-(methylamino)-3-phenylpropanamide

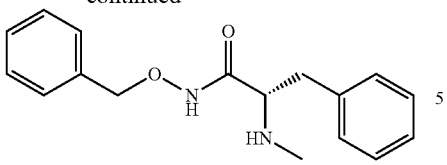

A 250-mL round-bottom flask was charged with (S)-tert-butyl 1-(benzyloxyamino)-1-oxo-3-phenylpropan-2-yl (methyl)carbamate (5.34 g, 13.9 mmol, 1.00 equiv), 1,4-dioxane (50 mL), and hydrochloric acid (4 N, 15 mL). The resulting solution was allowed to stir overnight at room temperature and concentrated under reduced pressure to provide 5.00 g (crude) of (S)—N-(benzyloxy)-2-(methyl-amino)-3-phenylpropanamide as a brown oil. LCMS (ESI, m/z): 285 [M+H]⁺.

Step 3: Preparation of (S)-5-benzyl-3-(benzyloxy)-1-methylimidazolidine-2,4-dione

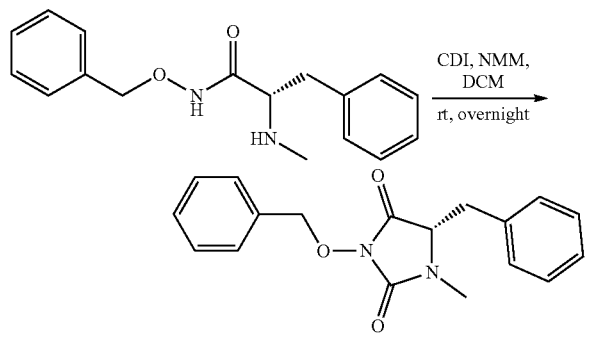

A 500-mL round-bottom flask was charged with (S)—N-(benzyloxy)-2-(methylamino)-3-phenylpropanamide (3.90 g, 13.7 mmol, 1.00 equiv), DCM (200 mL), and NMM (6.92 g, 68.4 mmol, 5.00 equiv). The resulting solution was allowed to stir for 1 h at room temperature. CDI (3.33 g, 20.5 mmol, 1.50 equiv) was added. The reaction mixture was allowed to stir overnight at room temperature and quenched with water (50 mL). The mixture was extracted with DCM (3×100 mL) and the organic layers were combined, washed with brine (3×100 mL), dried over anhydrous sodium sulfate, filtered and concentrated under reduced pressure. The residue was chromatographed on a silica gel column with DCM/MeOH (99/1) to provide 2.89 g (68% yield) of (S)-5-benzyl-3-(benzyloxy)-1-methylimidazolidine-2,4-dione as a yellow oil. LCMS (ESI, m/z): 311 [M+H]⁺.

Step 4: Preparation of (S)-5-benzyl-3-hydroxy-1-methylimidazolidine-2,4-dione

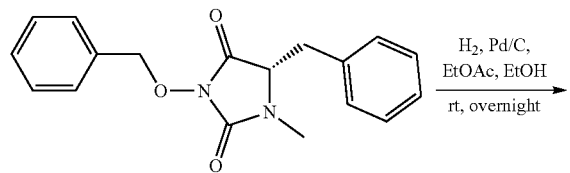

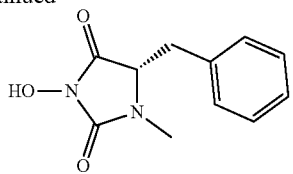

A 50-mL round-bottom flask was charged with (S)-5-benzyl-3-(benzyloxy)-1-methylimidazolidine-2,4-dione (754 mg, 2.43 mmol, 1.00 equiv), EtOAc (1 mL), EtOH (4 mL), and palladium carbon (1.0 g). Hydrogen was introduced in. The resulting solution was allowed to stir overnight at room temperature. The mixture was filtered and concentrated under reduced pressure to provide 428 mg (80% yield) of (S)-5-benzyl-3-hydroxy-1-methylimidazolidine-2,4-dione as a colorless oil. LCMS (ESI, m/z): 221 [M+H]⁺.

Step 5: Preparation of (S)-4-benzyl-3-methyl-2,5-dioxoimidazolidin-1-yl 4-(2-chloro-3-(piperidine-1-carbonyl)phenyl)piperazine-1-carboxylate

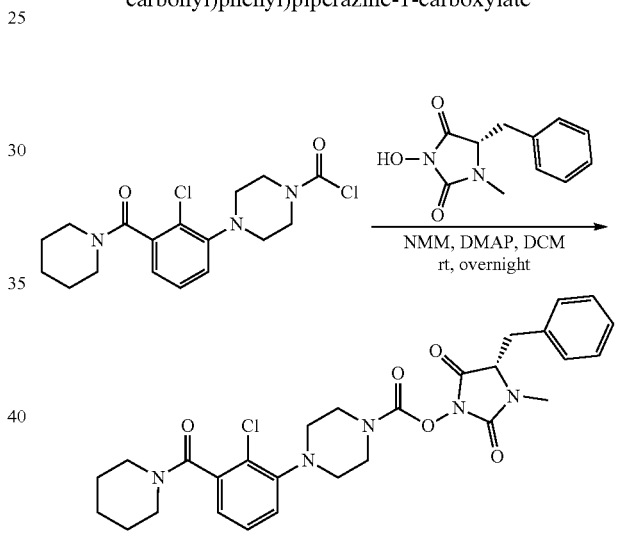

A 40-mL round-bottom flask was charged with (S)-5-benzyl-3-hydroxy-1-methylimidazolidine-2,4-dione (211 mg, 0.961 mmol, 1.20 equiv), 4-[2-chloro-3-[(piperidin-1-yl)carbonyl]phenyl]piperazine-1-carbonyl chloride (296 mg, 0.801 mmol, 1.00 equiv), DMAP (9.60 mg, 0.080 mmol, 0.10 equiv), NMM (242 mg, 2.39 mmol, 3.00 equiv), and DCM (5 mL). The resulting solution was allowed to stir overnight at room temperature and quenched with water (20 mL). The mixture was extracted with DCM (3×30 mL) and the organic layers were combined, washed with brine (3×30 mL), dried over anhydrous sodium sulfate, filtered and concentrated under reduced pressure. The crude product (168 mg) was purified by preparative HPLC to afford 85.2 mg (19% yield) of (S)-4-benzyl-3-methyl-2,5-dioxoimidazolidin-1-yl 4-(2-chloro-3-(piperidine-1-carbonyl)phenyl)piperazine-1-carboxylate as a white solid. ¹H NMR (400 MHz, Chloroform-d) δ 7.27-7.52 (m, 4H), 7.20-7.25 (m, 2H), 6.97-7.12 (m, 2H), 4.24-4.26 (m, 1H), 3.69-3.78 (m, 6H), 3.11-3.31 (m, 6H), 2.97-3.00 (m, 2H), 2.74-2.87 (m, 3H), 1.56-1.67 (m, 5H), 1.46 (br, 1H). LCMS (ESI, m/z): 554 [M+H]⁺.

83

Example 21: (S)-4-benzyl-2,5-dioxoimidazolidin-1-yl 4-(2-chloro-3-(piperidine-1-carbonyl)phenyl)-1,4-diazepane-1-carboxylate

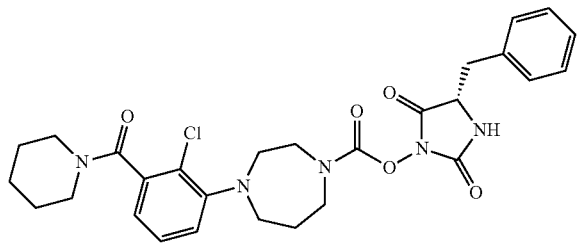 [SMILES: O=C(ON1C(=O)N[C@@H](Cc2ccccc2)C1=O)N1CCCN(c2cccc(C(=O)N3CCCCC3)c2Cl)CC1]

Step 1: Preparation of (3-bromo-2-chlorophenyl)(piperidin-1-yl)methanone

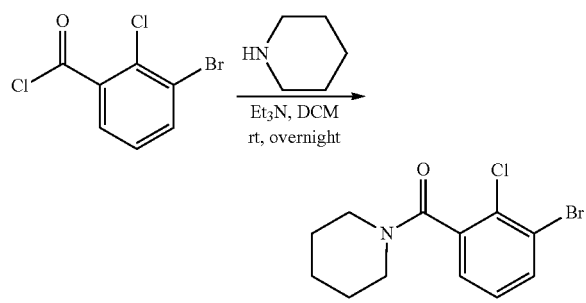

A 100-mL round-bottom flask was charged with 3-bromo-2-chlorobenzoyl chloride (1.62 g, 6.38 mmol, 1.00 equiv), piperidine (1.08 g, 12.7 mmol, 2.00 equiv), TEA (1.93 g, 19.1 mmol, 3.00 equiv), and DCM (30 mL). The resulting solution was allowed to stir overnight at room temperature and quenched with water (20 mL). The mixture was extracted with DCM (3×30 mL) and the organic layers were combined, washed with brine (2×30 mL), dried over anhydrous sodium sulfate, filtered and concentrated under reduced pressure. The residue was chromatographed on a silica gel column with EtOAc/petroleum ether (1/5) to provide 1.86 g (96% yield) of (3-bromo-2-chlorophenyl)(piperidin-1-yl)methanone as a light yellow oil. LCMS (ESI, m/z): 302 [M+H]$^+$.

Step 2: Preparation of tert-butyl 4-(2-chloro-3-(piperidine-1-carbonyl)phenyl)-1,4-diazepane-1-carboxylate

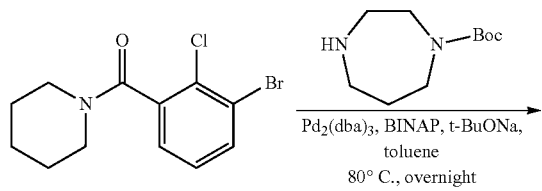

84

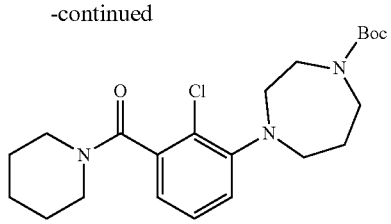

A 100-mL round-bottom flask was charged with (3-bromo-2-chlorophenyl)(piperidin-1-yl)methanone (1.45 g, 4.79 mmol, 1.00 equiv), tris(dibenzylideneacetone)dipalladium (0.248 g, 0.240 mmol, 0.05 equiv), bis(diphenylphosphino)-1,1'-binaphthyl (0.446 g, 0.721 mmol, 0.15 equiv), sodium tert-butoxide (0.688 g, 7.16 mmol, 1.50 equiv), toluene (10 ml), and tert-butyl 1,4-diazepane-1-carboxylate (1.43 g, 7.14 mmol, 1.50 equiv) under nitrogen. The resulting solution was allowed to stir overnight at 80° C. and quenched with water (20 mL). The mixture was extracted with EtOAc (3×30 mL) and the organic layers were combined, washed with brine (2×30 mL), dried over anhydrous sodium sulfate, filtered and concentrated under reduced pressure. The residue was chromatographed on a silica gel column with EtOAc/petroleum ether (1/3) to provide 1.53 g (76% yield) of tert-butyl 4-(2-chloro-3-(piperidine-1-carbonyl)phenyl)-1,4-diazepane-1-carboxylate as a brown oil. LCMS (ESI, m/z): 422 [M+H]$^+$.

Step 3: Preparation of (2-chloro-3-(1,4-diazepan-1-yl)phenyl)(piperidin-1-yl)methanone

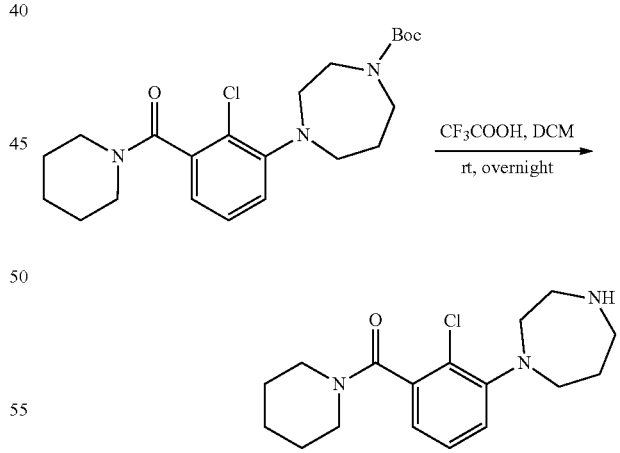

A 100-mL round-bottom flask was charged with tert-butyl 4-(2-chloro-3-(piperidine-1-carbonyl)phenyl)-1,4-diazepane-1-carboxylate (1.53 g, 3.63 mmol, 1.00 equiv), DCM (15 mL), and TFA (3 mL). The resulting solution was allowed to stir overnight at room temperature and concentrated under reduced pressure to provide 1.34 g (crude) of (2-chloro-3-(1,4-diazepan-1-yl)phenyl)(piperidin-1-yl)methanone as a brown oil. LCMS (ESI, m/z): 322 [M+H]$^+$.

Step 4: Preparation of 4-(2-chloro-3-(piperidine-1-carbonyl)phenyl)-1,4-diazepane-1-carbonyl chloride

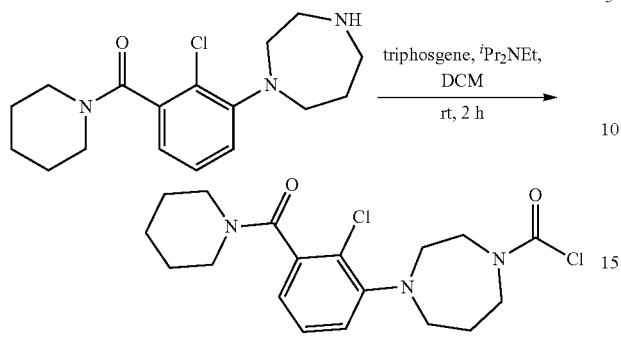

A 40-mL round-bottom flask was charged with triphosgene (59.4 mg, 0.201 mmol, 0.40 equiv), DCM (5 mL), and (2-chloro-3-(1,4-diazepan-1-yl)phenyl)(piperidin-1-yl)methanone (161 mg, 0.500 mmol, 1.00 equiv). DIPEA (194 mg, 1.50 mmol, 3.00 equiv) was added at 0° C. The resulting solution was allowed to stir for 2 h at room temperature and quenched with water (20 mL). The mixture was extracted with DCM (3×30 mL) and the organic layers were combined, washed with brine (2×30 mL), dried over anhydrous sodium sulfate, filtered and concentrated under reduced pressure to provide 192 mg (98% yield) of 4-(2-chloro-3-(piperidine-1-carbonyl)phenyl)-1,4-diazepane-1-carbonyl chloride as a yellow oil. LCMS (ESI, m/z): 384 [M+H]$^+$.

Step 5: Preparation of (S)-4-benzyl-2,5-dioxoimidazolidin-1-yl 4-(2-chloro-3-(piperidine-1-carbonyl)phenyl)-1,4-diazepane-1-carboxylate

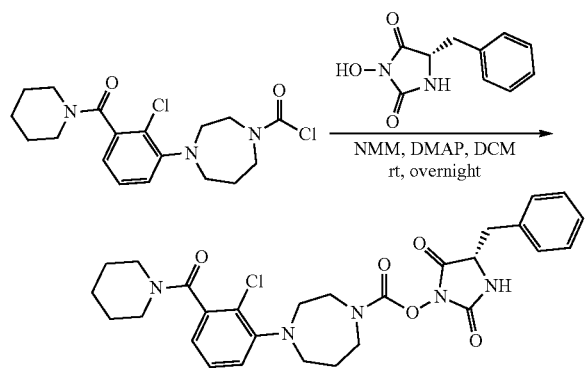

A 40-mL round-bottom flask was charged with 4-(2-chloro-3-(piperidine-1-carbonyl)phenyl)-1,4-diazepane-1-carbonyl chloride (192 mg, 0.501 mmol, 1.00 equiv), DMAP (6.00 mg, 0.0511 mmol, 0.10 equiv), DCM (5 mL), (S)-5-benzyl-3-hydroxyimidazolidine-2,4-dione (prepared as described in Example 7, Steps 1-4; 124 mg, 0.601 mmol, 1.20 equiv), and NMM (151 mg, 1.49 mmol, 3.00 equiv). The resulting solution was allowed to stir overnight at room temperature and quenched with water (20 mL). The mixture was extracted with DCM (3×30 mL) and the organic layers were combined, washed with brine (2×30 mL), dried over anhydrous sodium sulfate, filtered and concentrated under reduced pressure. The crude product (201 mg) was purified by preparative HPLC to afford 24.4 mg (9% yield) of (S)-4-benzyl-2,5-dioxoimidazolidin-1-yl 4-(2-chloro-3-(piperidine-1-carbonyl)phenyl)-1,4-diazepane-1-carboxylate as a white solid. $^1$H NMR (400 MHz, Chloroform-d) δ 7.34-7.38 (m, 3H), 7.26-7.32 (m, 2H), 7.08-7.13 (m, 1H), 6.91-6.94 (m, 1H), 5.35 (br, 1H), 4.34 (br, 1H), 3.69-3.91 (m, 5H), 3.00-3.59 (m, 7H), 2.84-2.90 (m, 1H), 2.05-2.31 (m, 2H), 1.50-1.79 (m, 7H), 1.45 (br, 1H). LCMS (ESI, m/z): 554 [M+H]$^+$.

Example 22: (S)-2,5-dioxo-4-(4-(trifluoromethyl)benzyl)imidazolidin-1-yl 4-(2-chloro-3-(piperidine-1-carbonyl)phenyl)piperazine-1-carboxylate

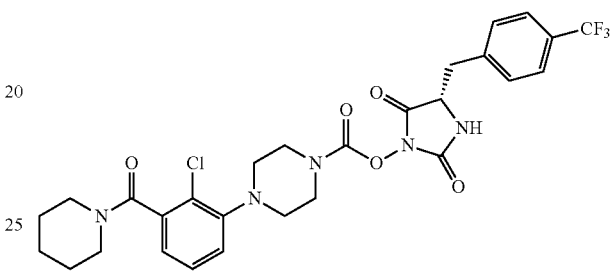

Step 1: Preparation of (S)-tert-butyl 1-(benzyloxyamino)-1-oxo-3-(4-(trifluoromethyl)phenyl)propan-2-ylcarbamate

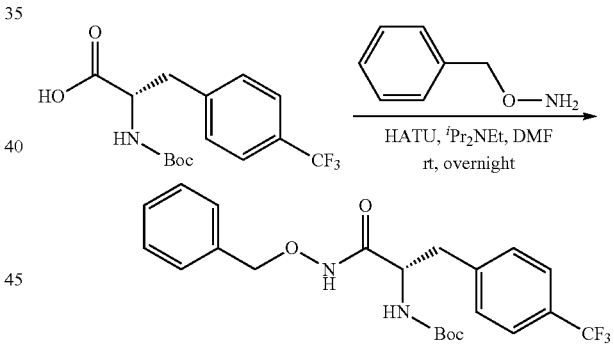

A 500-mL round-bottom flask was charged with (S)-2-(tert-butoxycarbonylamino)-3-(4-(trifluoromethyl)phenyl)propanoic acid (10.0 g, 30.0 mmol, 1.00 equiv), HATU (17.1 g, 44.9 mmol, 1.50 equiv), DMF (100 mL), and DIPEA (15.5 g, 120 mmol, 4.00 equiv). The resulting solution was allowed to stir for 1 h at room temperature. O-Benzylhydroxylamine (5.53 g, 44.9 mmol, 1.50 equiv) was added. The reaction mixture was allowed to stir overnight at room temperature and quenched with water (100 mL). The mixture was extracted with EtOAc (3×200 mL) and the organic layers were combined, washed with brine (2×200 mL), dried over anhydrous sodium sulfate, filtered and concentrated under reduced pressure. The residue was chromatographed on a silica gel column with EtOAc/petroleum ether (5/1) to provide 4.33 g (33% yield) of (S)-tert-butyl 1-(benzyloxyamino)-1-oxo-3-(4-(trifluoromethyl)phenyl)propan-2-ylcarbamate as a white solid. LCMS (ESI, m/z): 439 [M+H]$^+$.

Step 2: Preparation of (S)-2-amino-N-(benzyloxy)-3-(4-(trifluoromethyl)phenyl)propanamide

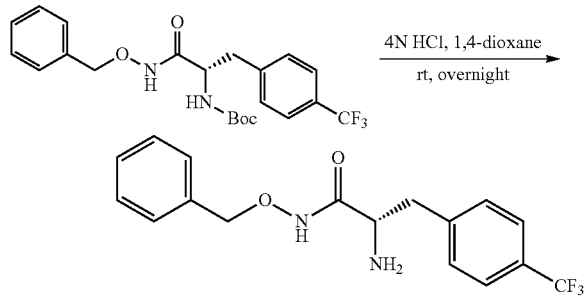

A 250-mL round-bottom flask was charged with (S)-tert-butyl 1-(benzyloxyamino)-1-oxo-3-(4-(trifluoromethyl)phenyl)propan-2-ylcarbamate (4.33 g, 9.88 mmol, 1.00 equiv), 1,4-dioxane (70 mL), and hydrochloric acid (4 N, 10 mL). The resulting solution was allowed to stir overnight at room temperature and concentrated under reduced pressure to provide 4.30 g (crude) of (S)-2-amino-N-(benzyloxy)-3-(4-(trifluoromethyl)phenyl)propanamide as a white solid. LCMS (ESI, m/z): 339 [M+H]$^+$.

Step 3: Preparation of (S)-3-(benzyloxy)-5-(4-(trifluoromethyl)benzyl)imidazolidine-2,4-dione

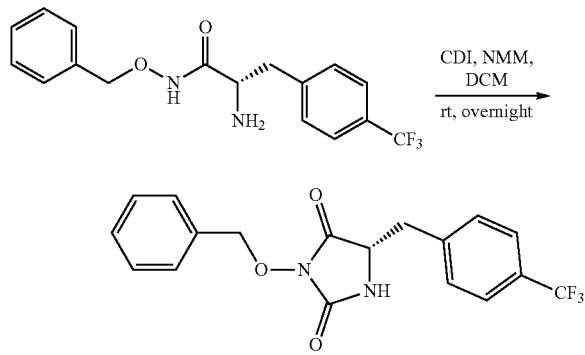

A 250-mL round-bottom flask was charged with (S)-2-amino-N-(benzyloxy)-3-[4-(trifluoromethyl)phenyl]propanamide (3.30 g, 9.75 mmol, 1.00 equiv), DCM (100 mL), and NMM (4.93 g, 48.7 mmol, 5.00 equiv). The resulting solution was allowed to stir for 1 h at room temperature. CDI (2.36 g, 14.5 mmol, 1.50 equiv) was added. The reaction mixture was allowed to stir overnight at room temperature and quenched with water (50 mL). The mixture was extracted with DCM (3×100 mL) and the organic layers were combined, washed with brine (2×100 mL), dried over anhydrous sodium sulfate, filtered and concentrated under reduced pressure. The residue was chromatographed on a silica gel column with EtOAc/petroleum ether (1/1) to provide 1.68 g (47% yield) of (S)-3-(benzyloxy)-5-(4-(trifluoromethyl)benzyl)imidazolidine-2,4-dione as a light yellow solid. LCMS (ESI, m/z): 365 [M+H]$^+$.

Step 4: Preparation of (S)-3-hydroxy-5-(4-(trifluoromethyl)benzyl)imidazolidine-2,4-dione

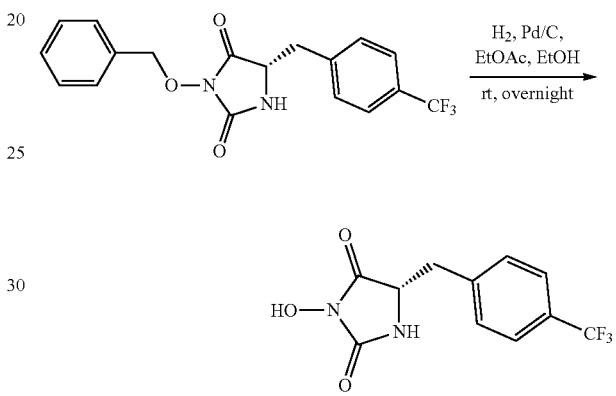

A 250-mL round-bottom flask was charged with (S)-3-(benzyloxy)-5-(4-(trifluoromethyl)benzyl)imidazolidine-2,4-dione (1.68 g, 4.61 mmol, 1.00 equiv), EtOAc (3 mL), EtOH (12 mL), and palladium carbon (1.00 g). Hydrogen was introduced in. The resulting solution was allowed to stir overnight at room temperature. The solids were filtered out. The resulting mixture was concentrated under reduced pressure to provide 0.602 g (48% yield) of (S)-3-hydroxy-5-(4-(trifluoromethyl)benzyl)imidazolidine-2,4-dione as a white solid. LCMS (ESI, m/z): 275 [M+H]$^+$.

Step 5: Preparation of (S)-2,5-dioxo-4-(4-(trifluoromethyl)benzyl)imidazolidin-1-yl 4-(2-chloro-3-(piperidine-1-carbonyl)phenyl)piperazine-1-carboxylate

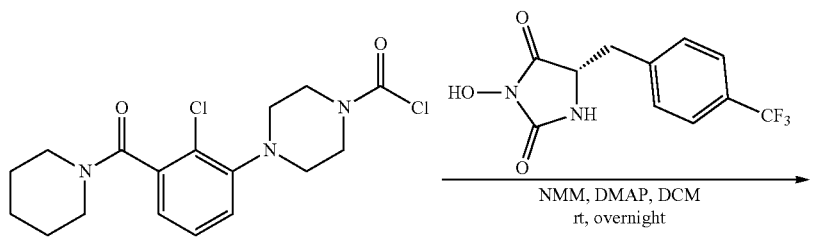

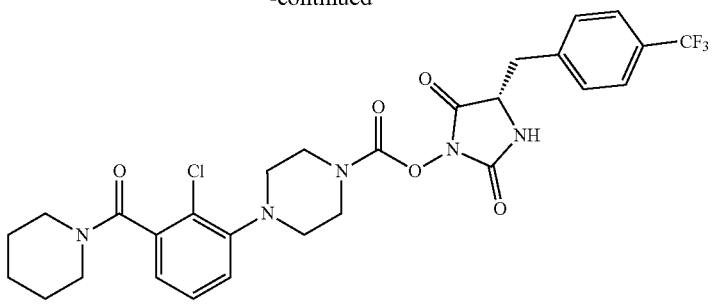

A 40-mL round-bottom flask was charged with 4-(2-chloro-3-(piperidine-1-carbonyl)phenyl)piperazine-1-carbonyl chloride (prepared as described in Example 1, Steps 5-9, using piperidine in Step 6; 185 mg, 0.501 mmol, 1.00 equiv), DMAP (6.00 mg, 0.0511 mmol, 0.10 equiv), DCM (5 mL), (S)-3-hydroxy-5-(4-(trifluoromethyl)benzyl)imidazolidine-2,4-dione (151 mg, 0.551 mmol, 1.10 equiv), and NMM (151 mg, 1.49 mmol, 3.00 equiv). The resulting solution was allowed to stir overnight at room temperature and quenched with water (20 mL). The mixture was extracted with DCM (3×30 mL) and the organic layers were combined, washed with brine (2×30 mL), dried over anhydrous sodium sulfate, filtered and concentrated under reduced pressure. The crude product (236 mg) was purified by preparative HPLC to afford (23% yield) of (S)-2,5-dioxo-4-(4-(trifluoromethyl)benzyl)imidazolidin-1-yl 4-(2-chloro-3-(piperidine-1-carbonyl)phenyl)piperazine-1-carboxylate as a white solid. $^1$H NMR (400 MHz, Chloroform-d) δ 7.61-7.63 (m, 2H), 7.33-7.38 (m, 2H), 7.26-7.30 (m, 1H), 7.02-7.05 (m, 1H), 6.97-6.99 (m, 1H), 5.68 (br, 1H), 4.37 (br, 1H), 3.71-3.91 (m, 6H), 3.40 (br, 1H), 3.11-3.29 (m, 4H), 2.95-3.05 (m, 3H), 1.67-1.77 (m, 5H), 1.45 (br, 1H). LCMS (ESI, m/z): 608 [M+H]$^+$.

Example 23: (S)-4-(4-chlorobenzyl)-2,5-dioxoimidazolidin-1-yl 4-(2-chloro-3-(piperidine-1-carbonyl)phenyl)piperazine-1-carboxylate

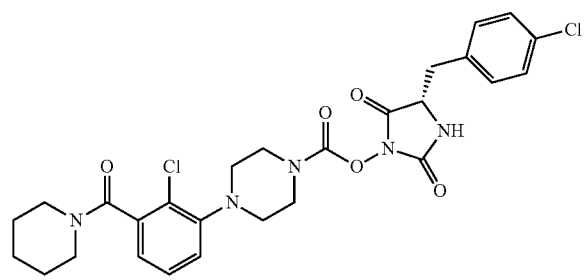

The title compound was synthesized as described in Example 22 using (S)-2-(tert-butoxycarbonylamino)-3-(4-chlorophenyl)propanoic acid in Step 1. Purification resulted in 15.0 mg (5% yield) of (S)-4-(4-chlorobenzyl)-2,5-dioxoimidazolidin-1-yl 4-(2-chloro-3-(piperidine-1-carbonyl)phenyl)piperazine-1-carboxylate as a white solid. $^1$H NMR (300 MHz, Chloroform-d) δ 7.15-7.24 (m, 3H), 6.70-7.02 (m, 4H), 4.70-4.84 (m, 1H), 3.76-4.18 (m, 3H), 3.35-3.64 (m, 3H), 3.01-3.24 (m, 7H), 2.60-2.99 (m, 2H), 1.58-1.68 (m, 5H), 1.47 (br, 1H). LCMS (ESI, m/z): 574 [M+H]$^+$.

Example 24: (S)-4-(4-methoxybenzyl)-2,5-dioxoimidazolidin-1-yl 4-(2-chloro-3-(piperidine-1-carbonyl)phenyl)piperazine-1-carboxylate

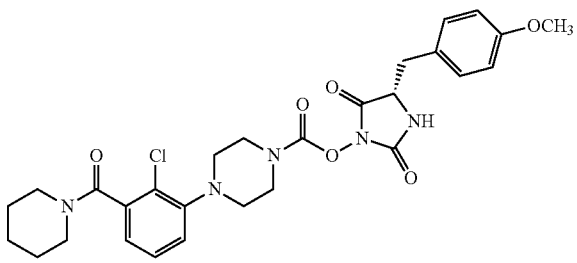 [SMILES: COc1ccc(C[C@@H]2NC(=O)N(OC(=O)N3CCN(c4cccc(C(=O)N5CCCCC5)c4Cl)CC3)C2=O)cc1]

The title compound was synthesized as described in Example 22 using (S)-2-(tert-butoxycarbonylamino)-3-(4-methoxyphenyl)propanoic acid in Step 1. Purification resulted in 73.7 mg (26% yield) of (S)-4-(4-methoxybenzyl)-2,5-dioxoimidazolidin-1-yl 4-(2-chloro-3-(piperidine-1-carbonyl)phenyl)piperazine-1-carboxylate as a white solid. $^1$H NMR (400 MHz, Chloroform-d) δ 7.28-7.30 (m, 1H), 7.14-7.16 (m, 2H), 6.97-7.04 (m, 2H), 6.87-6.97 (m, 2H), 5.36 (br, 1H), 4.28-4.30 (m, 1H), 3.69-4.83 (m, 9H), 3.32-3.36 (m, 1H), 3.16-3.23 (m, 4H), 2.94-3.09 (m, 2H), 2.74-2.87 (m, 1H), 1.57-1.68 (m, 5H), 1.47 (br, 1H). LCMS (ESI, m/z): 570 [M+H]$^+$.

II. Biological Evaluation

Compounds are tested to assess their Lp-PLA2 and serine hydrolase activity using the following in vitro assays.

In Vitro Competitive Activity-Based Protein Profiling

Mouse brain membrane proteomes (50 μL, 1.0 mg/mL total protein concentration) were preincubated with varying concentrations of inhibitors at 37° C. After 30 min, HT-01 probe (1.0 μL, 50 μM in DMSO) was added and the mixture was incubated for another 30 min at room temperature. Reactions were quenched with SDS loading buffer (15 μL-4×) and run on SDS-PAGE gels. Following gel imaging, serine hydrolase activity was determined by measuring fluorescent intensity of gel bands corresponding to PLA2G7 and ABHD6 using ImageJ 1.49 k software. IC50 data from this assay is shown in Table 2.

TABLE 2

| | ($IC_{50}$ value) | |
|---|---|---|
| Example | Lp-PLA2 | ABHD6 |
| 1 | ** | *** |
| 2 | ** | ** |
| 3 | ** | ** |

TABLE 2-continued

| Example | Lp-PLA2 (IC$_{50}$ value) | ABHD6 |
|---|---|---|
| 4 | 75% inhibition at 10 µM | ** |
| 5 | 75% inhibition at 10 µM | ** |
| 6 | 75% inhibition at 10 µM | ** |
| 7 | *** | *** |
| 8 | *** | ** |
| 9 | *** | ** |
| 10 | *** | *** |
| 11 | *** | *** |
| 12 | *** | *** |
| 13 | *** | *** |
| 14 | *** | *** |
| 15 | *** | *** |
| 16 | *** | *** |
| 17 | *** | *** |
| 18 | 25% at 100 µM | 25% at 100 µM |
| 19 | * | * |
| 20 | *** | *** |
| 21 | 100% inhibition at 10 µM | 100% inhibition at 10 µM |
| 22 | *** | *** |
| 23 | 50% at 100 µM | 50% at 100 µM |
| 24 | *** | *** |

*** is IC$_{50}$ less than 100 nM;
** is IC$_{50}$ between 100 nM and 1 µM;
* is IC$_{50}$ greater than 1 µM

We claim:

1. A compound having the structure of Formula (I), or a pharmaceutically acceptable salt or solvate thereof:

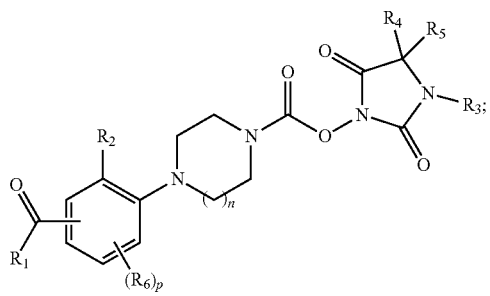

Formula (I)

wherein:
R$_1$ is selected from the group consisting of —N(R$_{10}$)R$_{11}$, —OH, C$_1$-C$_6$alkyl, and C$_1$-C$_6$alkoxy;
R$_2$ is selected from the group consisting of hydrogen, halogen, —N(R$_{12}$)R$_{13}$, —CF$_3$, C$_1$-C$_6$alkyl, and C$_1$-C$_6$alkoxy;
R$_3$ is hydrogen or C$_1$-C$_3$alkyl;
R$_4$ and R$_5$ are each independently selected from the group consisting of hydrogen, C$_1$-C$_6$alkyl optionally substituted by one, two, or three groups independently selected from halogen, cyano, and hydroxyl, and —(C$_1$-C$_6$alkylene)-(phenyl) optionally substituted by one, two, or three groups independently selected from halogen, cyano, —CF$_3$, —OH, C$_1$-C$_6$alkyl, and C$_1$-C$_6$alkoxy;
each R$_6$ is independently selected from the group consisting of halogen, —N(R$_{12}$)R$_{13}$, —CF$_3$, C$_1$-C$_6$alkyl, and C$_1$-C$_6$alkoxy;
R$_{10}$ and R$_{11}$ are each independently selected from the group consisting of hydrogen, and C$_1$-C$_3$alkyl; or R$_{10}$ and R$_{11}$ together with the nitrogen atom to which they are attached, form a 4-6 membered heterocyclic ring optionally substituted by C$_1$-C$_6$alkyl or —CO$_2$H;
each R$_{12}$ and R$_{13}$ are each independently selected from the group consisting of hydrogen, and C$_1$-C$_3$alkyl;
n is 1 or 2; and
p is 0, 1, or 2.

2. The compound of claim 1, or a pharmaceutically acceptable salt or solvate thereof, wherein R$_2$ is hydrogen or halogen.

3. The compound of claim 2, or a pharmaceutically acceptable salt or solvate thereof, wherein R$_1$ is —N(R$_{10}$)R$_{11}$.

4. The compound of claim 3, or a pharmaceutically acceptable salt or solvate thereof, wherein R$_{10}$ and R$_{11}$ together with the nitrogen atom to which they are attached, form a 4-6 membered heterocyclic ring optionally substituted by C$_1$-C$_6$alkyl or —CO$_2$H.

5. The compound of claim 4, or a pharmaceutically acceptable salt or solvate thereof, wherein R$_{10}$ and R$_{11}$ together with the nitrogen atom to which they are attached, form an unsubstituted pyrrolidine ring.

6. The compound of claim 4, or a pharmaceutically acceptable salt or solvate thereof, wherein R$_{10}$ and R$_{11}$ together with the nitrogen atom to which they are attached, form an unsubstituted piperidine ring.

7. The compound of claim 4, or a pharmaceutically acceptable salt or solvate thereof, wherein R$_{10}$ and R$_{11}$ together with the nitrogen atom to which they are attached, form a piperazine ring optionally substituted by C$_1$-C$_6$alkyl.

8. The compound of claim 4, or a pharmaceutically acceptable salt or solvate thereof, wherein R$_{10}$ and R$_{11}$ together with the nitrogen atom to which they are attached, form a morpholine ring.

9. The compound of claim 4, or a pharmaceutically acceptable salt or solvate thereof, wherein R$_4$ is hydrogen.

10. The compound of claim 9, or a pharmaceutically acceptable salt or solvate thereof, wherein R$_5$ is unsubstituted —CH$_2$-phenyl.

11. The compound of claim 9, or a pharmaceutically acceptable salt or solvate thereof, wherein R$_3$ is hydrogen.

12. The compound of claim 11, or a pharmaceutically acceptable salt or solvate thereof, wherein n is 1.

13. The compound of claim 12, or a pharmaceutically acceptable salt or solvate thereof, wherein p is 0.

14. The compound of claim 13, or a pharmaceutically acceptable salt or solvate thereof, wherein R$_2$ is hydrogen.

15. The compound of claim 13, or a pharmaceutically acceptable salt or solvate thereof, wherein R$_2$ is halogen.

16. The compound of claim 15, or a pharmaceutically acceptable salt or solvate thereof, wherein R$_2$ is Cl.

17. A compound, or a pharmaceutically acceptable salt or solvate thereof, selected from:
(S)-4-isopropyl-2,5-dioxoimidazolidin-1-yl 4-(2-chloro-3-(pyrrolidine-1-carbonyl)phenyl)piperazine-1-carboxylate;
(S)-4-isopropyl-2,5-dioxoimidazolidin-1-yl 4-(2-chloro-3-(piperidine-1-carbonyl)phenyl)piperazine-1-carboxylate;
(S)-4-isopropyl-2,5-dioxoimidazolidin-1-yl 4-(2-chloro-3-(morpholine-4-carbonyl)phenyl)piperazine-1-carboxylate;
(R)-4-isopropyl-2,5-dioxoimidazolidin-1-yl 4-(2-chloro-3-(pyrrolidine-1-carbonyl)phenyl)piperazine-1-carboxylate;

(R)-4-isopropyl-2,5-dioxoimidazolidin-1-yl 4-(2-chloro-3-(piperidine-1-carbonyl)phenyl)piperazine-1-carboxylate;

(R)-4-isopropyl-2,5-dioxoimidazolidin-1-yl 4-(2-chloro-3-(morpholine-4-carbonyl)phenyl)piperazine-1-carboxylate;

(S)-4-benzyl-2,5-dioxoimidazolidin-1-yl 4-(2-chloro-3-(pyrrolidine-1-carbonyl)phenyl)piperazine-1-carboxylate;

(S)-4-benzyl-2,5-dioxoimidazolidin-1-yl 4-(2-chloro-3-(piperidine-1-carbonyl)phenyl)piperazine-1-carboxylate;

(S)-4-benzyl-2,5-dioxoimidazolidin-1-yl 4-(2-chloro-3-(morpholine-4-carbonyl)phenyl)piperazine-1-carboxylate;

(R)-4-benzyl-2,5-dioxoimidazolidin-1-yl 4-(2-chloro-3-(pyrrolidine-1-carbonyl)phenyl)piperazine-1-carboxylate;

(R)-4-benzyl-2,5-dioxoimidazolidin-1-yl 4-(2-chloro-3-(piperidine-1-carbonyl)phenyl)piperazine-1-carboxylate;

(R)-4-benzyl-2,5-dioxoimidazolidin-1-yl 4-(2-chloro-3-(morpholine-4-carbonyl)phenyl)piperazine-1-carboxylate;

(S)-4-benzyl-2,5-dioxoimidazolidin-1-yl 4-(3-(piperidine-1-carbonyl)phenyl)piperazine-1-carboxylate;

(S)-4-benzyl-2,5-dioxoimidazolidin-1-yl 4-(2-chloro-3-(4-methylpiperazine-1-carbonyl)phenyl)piperazine-1-carboxylate;

(S)-4-benzyl-2,5-dioxoimidazolidin-1-yl 4-(2-chloro-4-(piperidine-1-carbonyl)phenyl)piperazine-1-carboxylate;

(S)-4-benzyl-2,5-dioxoimidazolidin-1-yl 4-(2-chloro-3-(dimethylcarbamoyl)phenyl)piperazine-1-carboxylate;

(S)-4-benzyl-2,5-dioxoimidazolidin-1-yl 4-(2-chloro-5-(piperidine-1-carbonyl)phenyl)piperazine-1-carboxylate;

(S)-4-benzyl-2,5-dioxoimidazolidin-1-yl 4-(3-carbamoyl-2-chlorophenyl)piperazine-1-carboxylate;

(S)-4-benzyl-3-methyl-2,5-dioxoimidazolidin-1-yl 4-(2-chloro-3-(piperidine-1-carbonyl)phenyl)piperazine-1-carboxylate;

(S)-4-benzyl-2,5-dioxoimidazolidin-1-yl 4-(2-chloro-3-(piperidine-1-carbonyl)phenyl)-1,4-diazepane-1-carboxylate;

(S)-2,5-dioxo-4-(4-(trifluoromethyl)benzyl)imidazolidin-1-yl 4-(2-chloro-3-(piperidine-1-carbonyl)phenyl)piperazine-1-carboxylate;

(S)-4-(4-chlorobenzyl)-2,5-dioxoimidazolidin-1-yl 4-(2-chloro-3-(piperidine-1-carbonyl)phenyl)piperazine-1-carboxylate; and (S)-4-(4-methoxybenzyl)-2,5-dioxoimidazolidin-1-yl 4-(2-chloro-3-(piperidine-1-carbonyl)phenyl)piperazine-1-carboxylate.

18. A pharmaceutical composition comprising a pharmaceutically acceptable diluent, excipient or binder, and a compound of claim 1; or a pharmaceutically acceptable salt or solvate thereof.

19. A method of therapeutically treating a disease, disorder or condition in a mammal that would benefit from lipoprotein-associated phospholipase A2 (Lp-PLA2) inhibition comprising administering to the mammal a therapeutically effective amount of a compound, or a pharmaceutically acceptable salt, or solvate thereof, according to claim 1.

20. The method of claim 19, wherein the disease, disorder or condition in a mammal is ischemia, traumatic brain injury, multiple sclerosis, diabetes, Alzheimer's disease, Parkinson's disease, amyotrophic lateral sclerosis (ALS), and cancer.

* * * * *